US010034674B2

(12) United States Patent
Chudik

(10) Patent No.: US 10,034,674 B2
(45) Date of Patent: Jul. 31, 2018

(54) UNIVERSAL ANTERIOR CRUCIATE LIGAMENT REPAIR AND RECONSTRUCTION SYSTEM

(76) Inventor: Steven C Chudik, Western Springs, IL (US)

( * ) Notice: Subject to any disclaimer, the term of this patent is extended or adjusted under 35 U.S.C. 154(b) by 1362 days.

(21) Appl. No.: 11/701,902

(22) Filed: Feb. 2, 2007

(65) Prior Publication Data

US 2007/0233151 A1    Oct. 4, 2007

Related U.S. Application Data

(60) Provisional application No. 60/764,026, filed on Feb. 2, 2006.

(51) Int. Cl.
| | |
|---|---|
| *A61B 17/32* | (2006.01) |
| *A61B 17/17* | (2006.01) |
| *A61B 17/3211* | (2006.01) |
| *A61B 17/88* | (2006.01) |
| *A61F 2/08* | (2006.01) |
| *A61B 17/16* | (2006.01) |
| *A61B 17/34* | (2006.01) |
| *A61B 17/00* | (2006.01) |

(52) U.S. Cl.
CPC ...... *A61B 17/1714* (2013.01); *A61B 17/1764* (2013.01); *A61B 17/3211* (2013.01); *A61B 17/8869* (2013.01); *A61F 2/0805* (2013.01); *A61F 2/0811* (2013.01); *A61B 17/1604* (2013.01); *A61B 17/1608* (2013.01); *A61B 17/1631* (2013.01); *A61B 17/1675* (2013.01); *A61B 17/3421* (2013.01); *A61B 17/8875* (2013.01); *A61B 2017/0023* (2013.01); *A61B 2017/3443* (2013.01); *A61F 2002/0852* (2013.01); *A61F 2002/0858* (2013.01)

(58) Field of Classification Search
CPC ...... A61B 17/3211; A61B 2017/32113; A61B 2017/32116; A61B 17/3213; A61B 17/3217
USPC .............................. 606/79–85, 86 R, 167–170
See application file for complete search history.

(56) References Cited

U.S. PATENT DOCUMENTS

| | | | | |
|---|---|---|---|---|
| 4,642,090 A | * | 2/1987 | Utrata | 604/22 |
| 4,719,915 A | * | 1/1988 | Porat et al. | 606/167 |
| 5,071,426 A | * | 12/1991 | Dolgin et al. | 606/167 |
| 5,843,108 A | * | 12/1998 | Samuels | 606/167 |

(Continued)

OTHER PUBLICATIONS

Magnus et al. Tendon Thickness and Depth from Skin for Supraspinatus, Common Wrist and Finger Extensors, Patellar and Achilles Tendons, Physiotherapy, Jun. 2003, vol. 89 No. 6, pp. 376-383.*

(Continued)

*Primary Examiner* — Matthew Lawson
(74) *Attorney, Agent, or Firm* — Gregory B. Beggs

(57) ABSTRACT

A system is disclosed for repairing and reconstructing an injured anterior cruciate ligament (ACL). This system may be used irrespective of the type of patient or the ACL graft selected. Means for performing single or multiple bundle reconstruction, primary ACL repair and physeal-sparing ACL reconstruction are disclosed. A guide for inside-out creation of a femoral tunnel independent of the tibial tunnel is also disclosed, as well as a series of implant options for tibial and femoral fixation of any bone-soft-tissue composite or soft-tissue-only graft.

1 Claim, 51 Drawing Sheets

(56) References Cited

U.S. PATENT DOCUMENTS

| | | | | |
|---|---|---|---|---|
| 6,048,354 | A * | 4/2000 | Lawrence | A61B 17/3211 |
| | | | | 606/167 |
| 6,110,175 | A * | 8/2000 | Scholl | A61B 17/1604 |
| | | | | 606/79 |
| 6,224,574 | B1 * | 5/2001 | Al-Labban | A61M 5/178 |
| | | | | 604/187 |
| 6,270,501 | B1 * | 8/2001 | Freiberg | A61B 17/1735 |
| | | | | 606/79 |
| 6,346,115 | B1 * | 2/2002 | Lawrence | A61B 17/3211 |
| | | | | 606/167 |
| 6,383,179 | B1 * | 5/2002 | Neuberger | A61B 18/22 |
| | | | | 606/13 |
| 6,761,726 | B1 * | 7/2004 | Findlay | A61B 10/025 |
| | | | | 604/506 |
| 7,097,642 | B1 * | 8/2006 | Sprague et al. | 606/27 |
| 2004/0220497 | A1 * | 11/2004 | Findlay | A61B 10/025 |
| | | | | 600/562 |
| 2006/0015066 | A1 * | 1/2006 | Turieo | A61B 17/3403 |
| | | | | 604/136 |
| 2008/0045965 | A1 * | 2/2008 | Miller | A61B 10/025 |
| | | | | 606/80 |
| 2008/0262318 | A1 * | 10/2008 | Gorek et al. | 600/235 |

OTHER PUBLICATIONS

Shankar et al. Influence of skin-to-muscle and muscle-to-bone thickness on depth of needle penetration in adults at the deltoid intramuscular injection site, Medical Journal Armed Forces India, 2014, vol. 70, pp. 338-343.*

Hohendorff et al. Length, girths, and diameter of children's fingers from 3 to 10 years of age, Annals of Anatomy, 2010, vol. 192, pp. 156-161.*

* cited by examiner

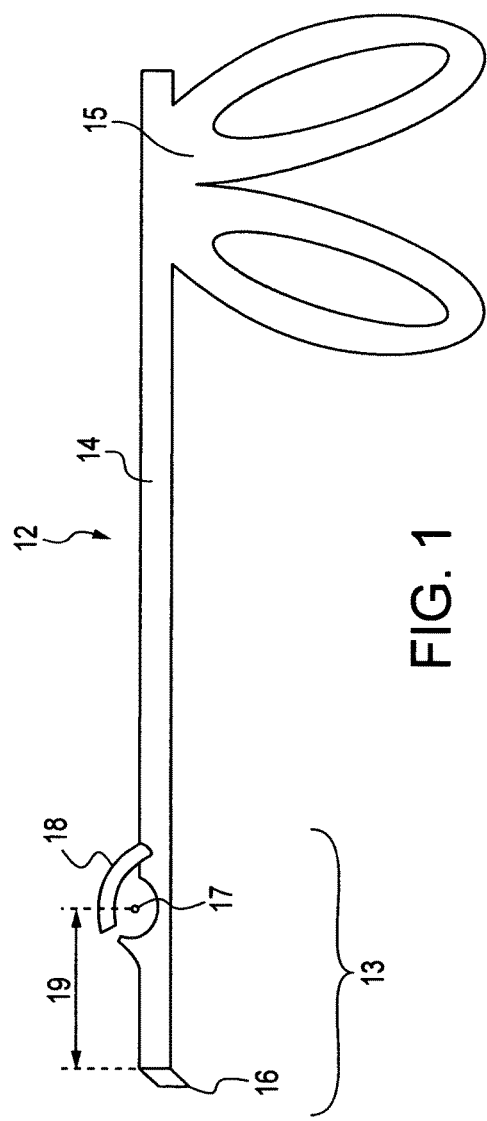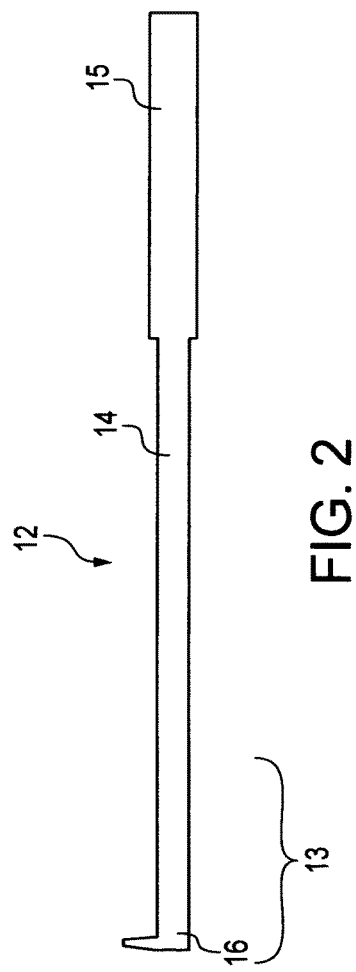

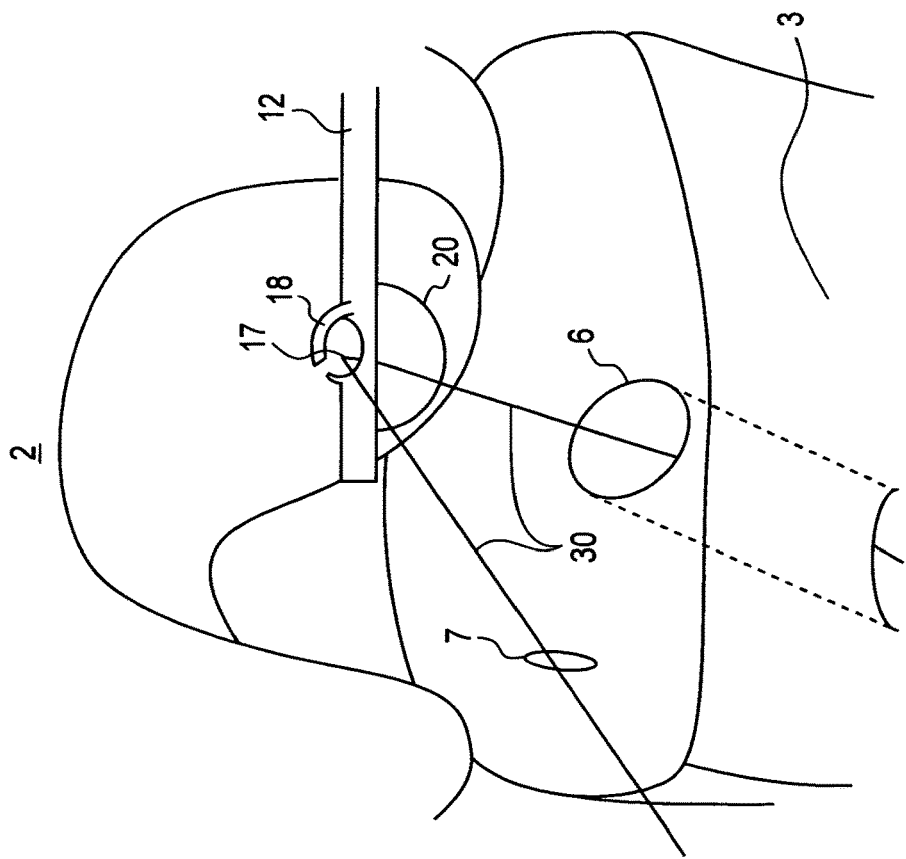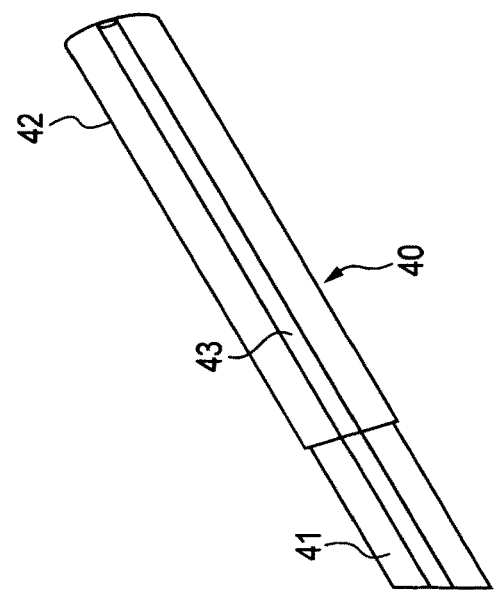

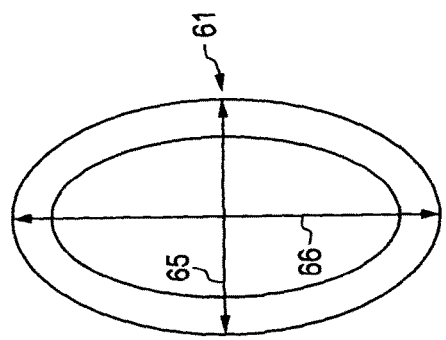
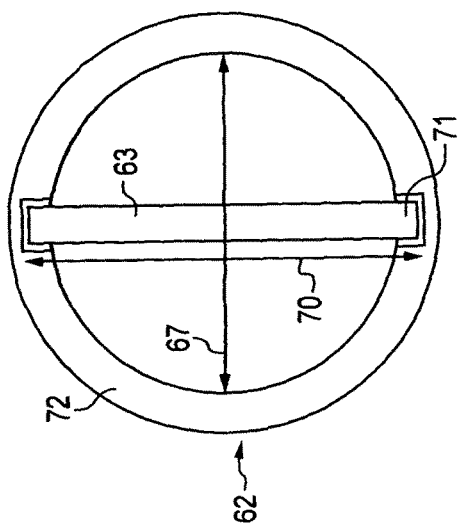
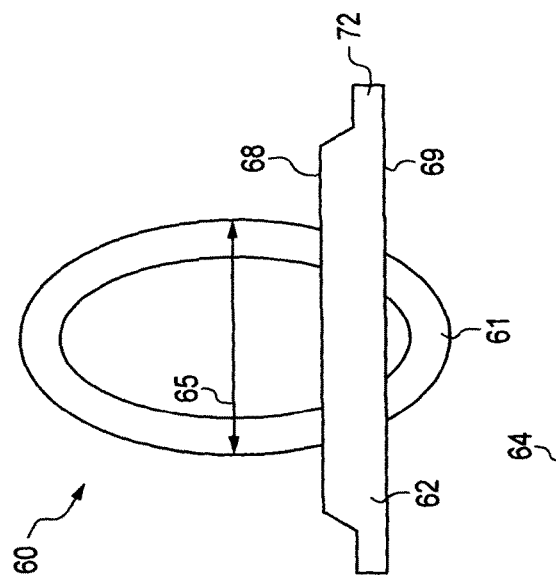

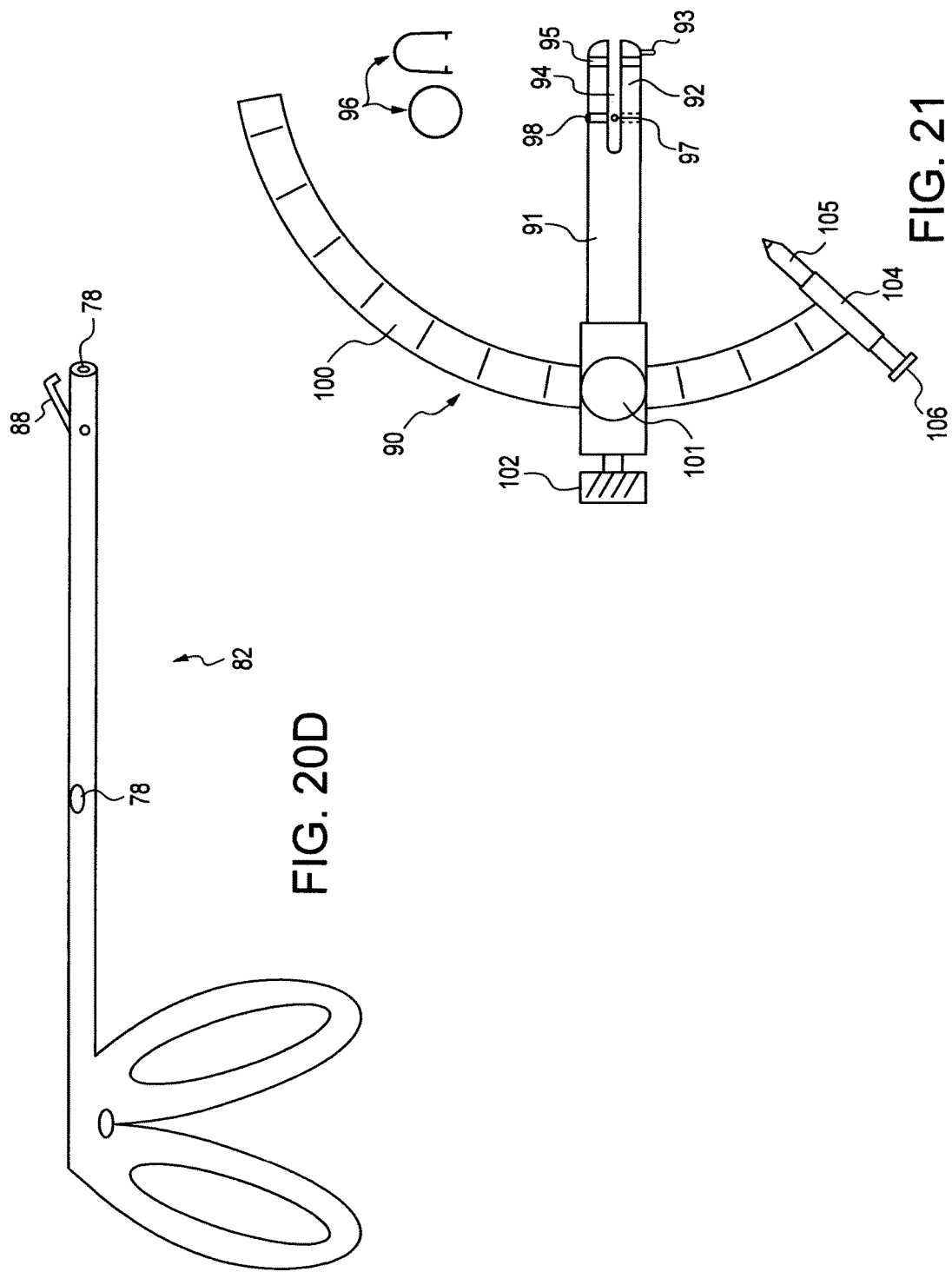

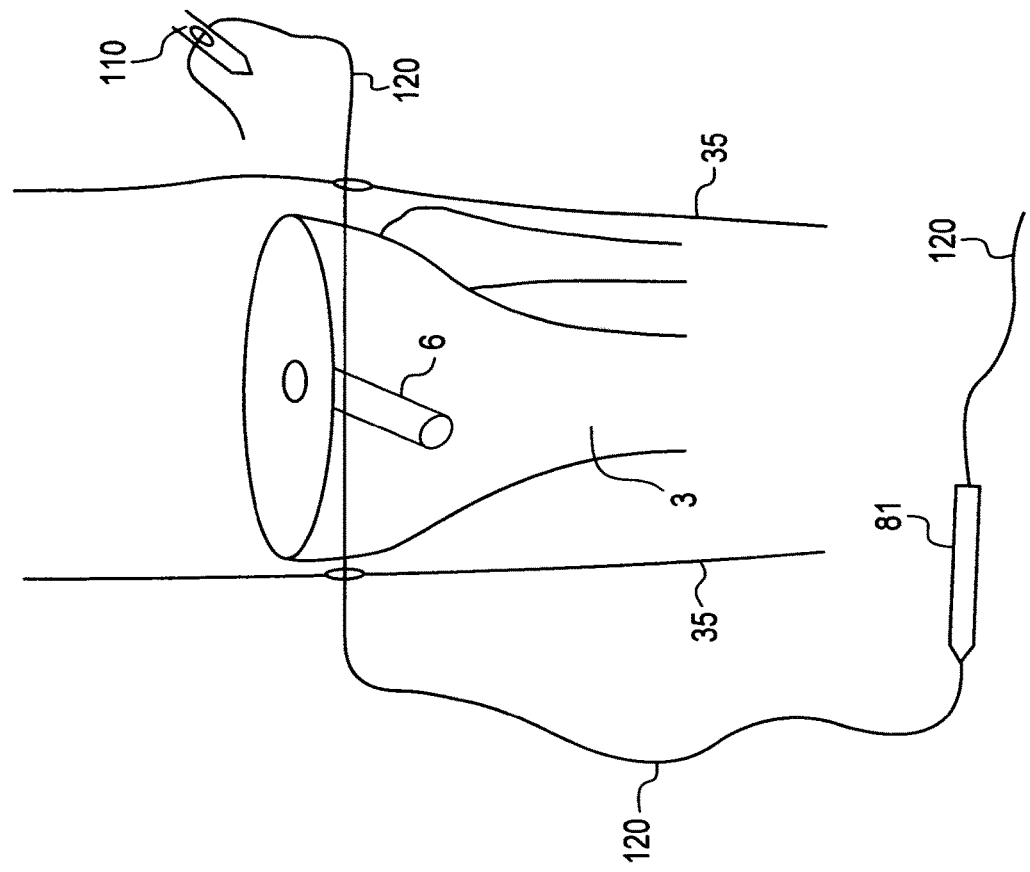
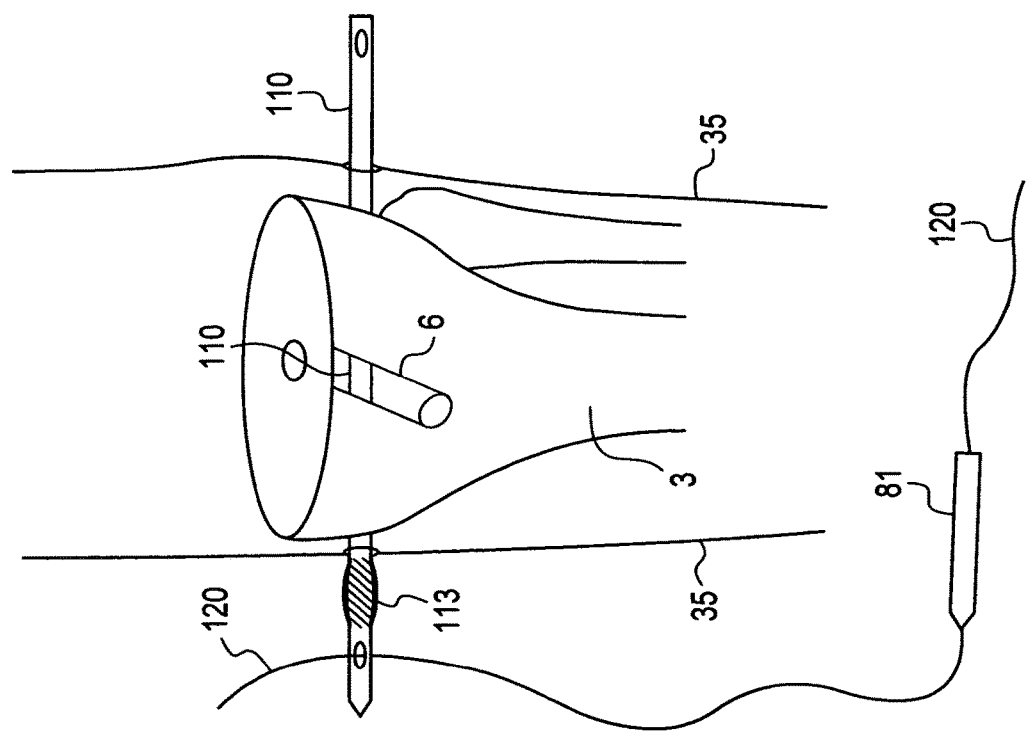
FIG. 24D
FIG. 24E

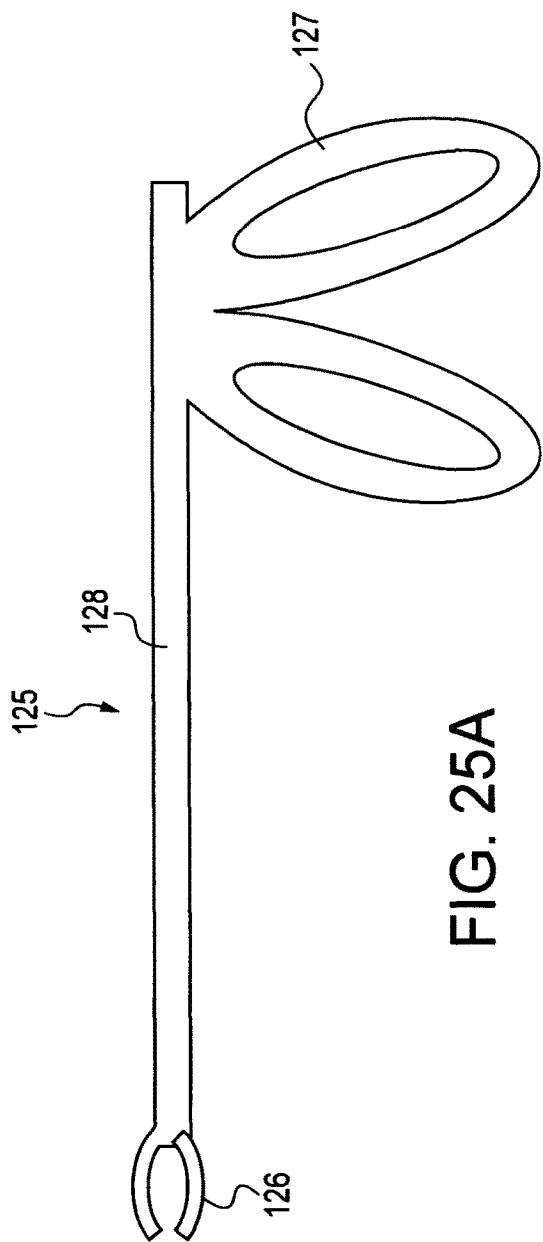
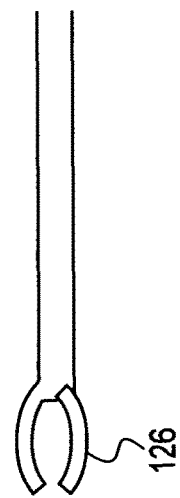
FIG. 25A
FIG. 25B

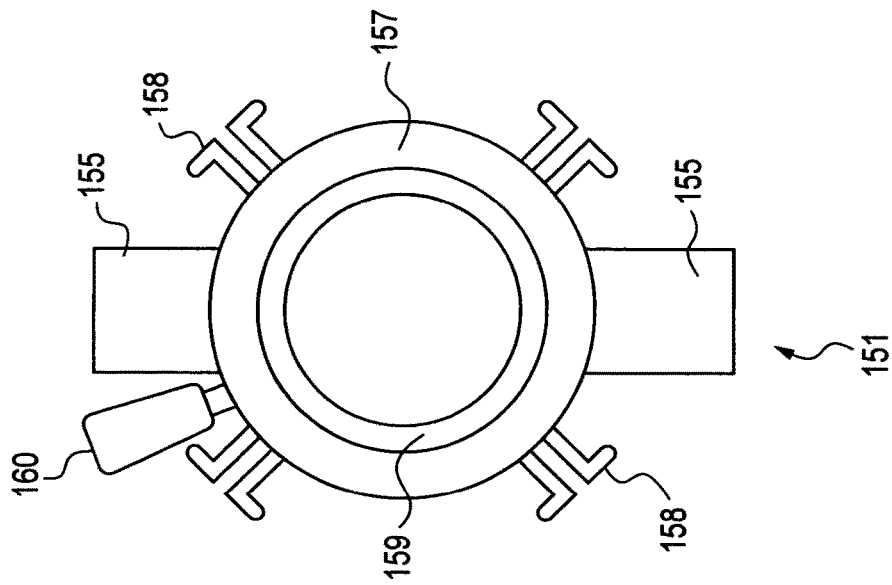
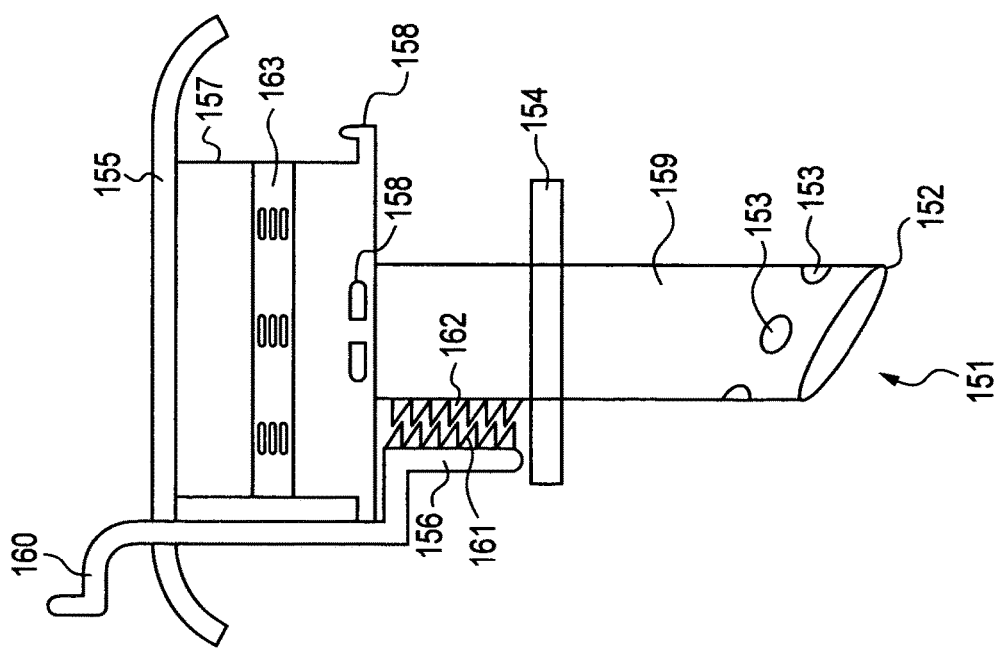

UNIVERSAL ANTERIOR CRUCIATE LIGAMENT REPAIR AND RECONSTRUCTION SYSTEM

This is a nonprovisional application which claims the filing date of the same applicant's provisional application Ser. No. 60/764,026 filed in the United States Patent and Trademark Office on Feb. 2, 2006.

This invention relates to systems for repairing and reconstructing injured anterior cruciate ligaments. More particularly it relates to a novel method and related family of methods of orthopaedic surgery for repairing and reconstructing an injured anterior cruciate ligament. It also relates to new and improved instruments and implants used in practicing the new method and family of methods.

Except for the provisional application referred to above, there are no patent applications related to this one. Neither this application nor the provisional application upon which it relies is subject to any federally sponsored research or development or to any joint research agreement.

BACKGROUND OF THE INVENTION

Orthopaedic surgeons perform reconstructive surgery of the anterior cruciate ligament (ACL) on patients who have traumatically injured this ligament. ACL reconstructive surgery restores the function of the ACL in the human knee and provides stability for the knee allowing patients to return to athletic activities. Without ACL reconstructive surgery, patients typically experience instability, "giving way," of the knee and incur further injury to other important anatomic structures of the knee, including meniscal and articular cartilage.

BRIEF SUMMARY OF THE INVENTION

While there are different surgical methods, instruments and implants used to reconstruct an ACL depending upon the patient and the ACL graft selected for the reconstructive procedure, the present invention describes a novel universal system of methods, instruments and implants to repair and reconstruct an ACL irrespective of the type of patient or ACL graft selected. This invention also includes a means to perform single or multiple bundle ACL reconstruction, primary ACL repair, and physeal (growth plate)-sparing ACL reconstruction, in the skeletal immature patient.

This invention includes a novel guide for "inside-out" creation of a femoral tunnel independent of the tibial tunnel, and it also includes a series of implant options providing a complete set for tibial and femoral fixation of any bone-soft-tissue composite or soft-tissue-only ACL graft.

Other benefits include more reliable methods for anatomic positioning of femoral tunnels, a technically facile method of creating femoral and tibial tunnels independent of each other, and a universal method for tunnel creation irrespective of patient or ACL graft selection.

The present invention especially allows a surgeon to become familiar with a single universal system of methods, instruments and implants which allows him or her to treat all patients with any graft and achieve the most reliable and reproducible technical and clinical results.

Accordingly, one object of this invention is to provide a universal system for a single surgeon to use in repairing and reconstructing an ACL in any patient using any graft.

Another object of this invention is to provide a novel guide for simply and easily creating an anatomic femoral tunnel independently of a tibial tunnel by directing a guide pin from a separate portal directly through the anatomic footprint of the ACL.

Another object of this invention is to provide a guide which allows for the passage of a guide wire from multiple directions, through the tibial tunnel and other arthroscopic portals, and also allows for the creation of multiple femoral tunnels, the creation of an epiphyseal (physeal sparing) femoral tunnel, and the repair of the torn stump of the ACL, all using a consistent simple method.

Another object of this invention is to provide a novel cannulated scalpel for improved accuracy in creating a limited passageway through skin and soft-tissue over a guide wire.

Another object of this invention is to provide a method of drilling bone tunnels over a guide wire from any direction.

Another object of this invention is to provide a novel surgical ring fixation tool which includes a ring and a ring capture button for fixing a loop end of a soft-tissue graft in a bone tunnel.

Another object of this invention is to provide a novel surgical ring fixation tool which can be used in conjunction with a tunnel in any bone according to a simple consistent method.

Another object of this invention is to provide a novel suspension pin for fixing a loop end of a soft-tissue graft in a tunnel of any bone.

Another object of this invention is to provide a novel hybrid suspension pin for fixing a loop end of a soft-tissue graft in a bone tunnel.

Another object of this invention is to provide a surgical pin guide capable of being placed in any bone tunnel from any direction for accurately inserting a pin in the bone across the bone tunnel and facilitating both the placement of a graft and the fixation of the graft with the pin.

Another object of this invention is to provide a suspension pin insertion tool having a tip with inverse geometry to the rear end of a suspension pin for inserting the pin into any bone.

Another object of this invention is to provide a wire cutting tool capable of being placed through small percutaneous skin incisions and operable to cut and remove the wire ends of a surgical pin guide wire element.

Another object of this invention is to provide a guide pin having a sharp leading tip, cannulations at its ends, and a body having an enlarged diameter portion with an outwardly facing cutting surface intermediate the cannulations for cutting a passageway in a bone larger that the rest of the guide pin's body.

Another object of this invention is to provide a wire passing tool for performing a novel method of passing a flexible wire from one bone tunnel to another.

Another object of this invention is to provide a method of loading a soft-tissue graft onto a central loop of flexible wire and thereafter straightening the wire to draw the soft-tissue graft into a desired position in a bone tunnel.

Another object of this invention is to provide a modular and non-modular interference screw-ligament washer for fixing the free end of a graft in a bone tunnel at two sites, namely, at the tunnel inner wall and at the outer cortical surface of the tunnel.

Another object of this invention is to provide an insertion tensioner tool and its associated components.

Another object of this invention is to provide a method of performing ACL repair.

Another object of this invention is to provide a method of performing ACL reconstruction on a skeletally immature patient with open physes (growth plates).

Other objects and features of this invention will be apparent to orthopaedic surgeons and other persons who are skilled in the art of ACL repair and reconstruction and who design solutions thereto, particularly after reviewing the following description of the preferred embodiments of the present invention and the accompanying drawings.

BRIEF DESCRIPTION OF THE DRAWINGS

FIG. 1 is a perspective view of a novel femoral guide in accordance with the present invention.

FIG. 2 is a top plan view of the guide in FIG. 1.

FIG. 6 is an exploded view of the disposition of a guide pin in the femur of a knee utilizing the femoral guide of claim 1 in accordance with the present invention.

FIG. 7 is a perspective view of a cannulated scalpel in accordance with the present invention.

FIG. 12 is a perspective view of a surgical ring fixation tool with its ring engaged in its ring capture button in accordance with the present invention.

FIG. 13 is a perspective view of the ring of FIG. 12.

FIG. 14 is a perspective view of a ring capture button in the surgical ring fixation tool of FIG. 12.

FIG. 20D is a perspective view of a guide wire cutting tool for removing the wire ends of a surgical pin guide wire element in accordance with the present invention.

FIG. 21 is a perspective view of a surgical pin guide in accordance with the present invention.

FIG. 24D is a schematic view of an alternative manner of attaching a flexible wire of the suspension pin to the surgical guide pin traversing a bone tunnel in accordance with the present invention.

FIG. 24E is a schematic view of an alternative manner of exchanging the surgical guide pin of this invention with the flexible wire of the suspension pin of this invention.

FIG. 25A is a perspective view of a wire passing tool in accordance with the present invention.

FIG. 25B is an exploded view of the wire passing tool shown in FIG. 25A opening its functional tip.

FIG. 42 is a perspective view of an insertion-tensioner tool in accordance with the present invention.

FIG. 43 is a top plan view of the insertion-tensioner tool shown in FIG. 42.

DETAILED DESCRIPTION OF THE INVENTION

Figure 3:
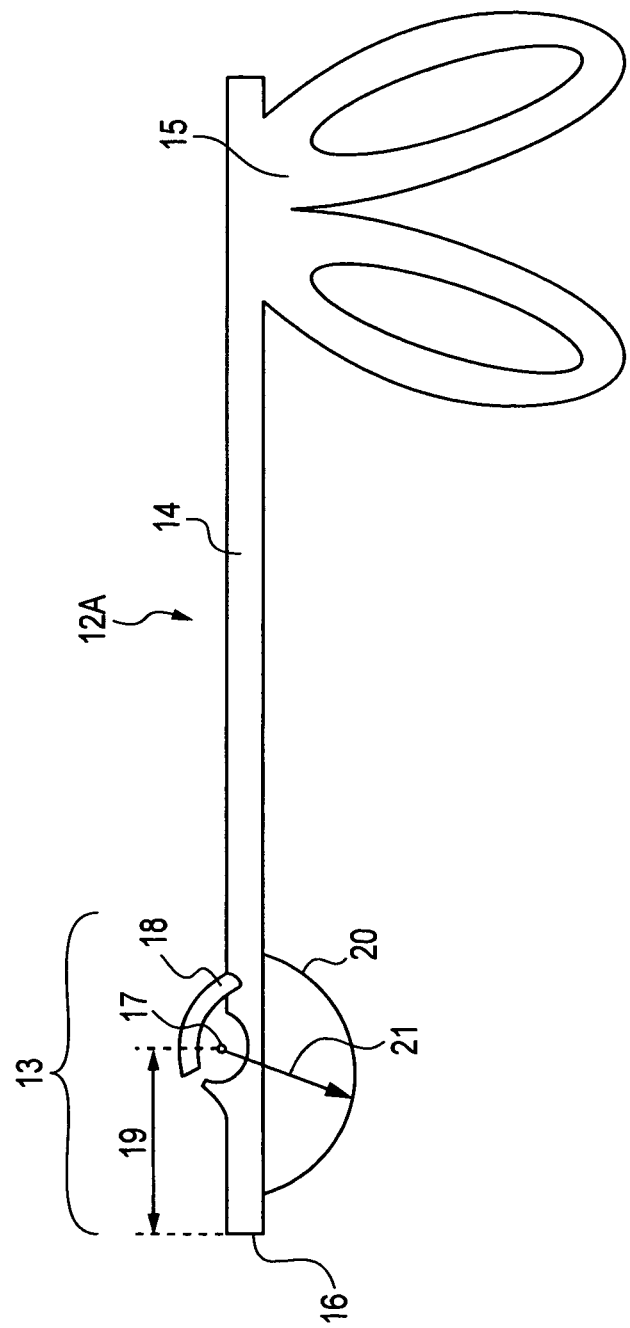
FIG. 3 is a perspective view of an alternative embodiment of the novel femoral guide of FIG. 1 with a semi-circular flexible guide loop.

The present invention relates to a family of methods, instruments and implants for performing ACL reparative and reconstructive surgery to the knee 1, including femur 2 and tibia 3. The present invention utilizes novel techniques and incorporates a novel femoral guide 12, a cannulated scalpel 40, novel graft fixation devices 60, 80, 81, 130, 140, a novel surgical pin guide 90 and associated instruments 82, 83, 110, 120, a novel insertional-tensioner tool 151 and associated instruments 165, 168, 180, 175, 190, a special protective sleeve 225, a bullet guide 235, and a cannulated drill bit 230.

Initially, conventional techniques of arthroscopic assisted ACL surgery are performed. After one or more tibial tunnels 6 are created, creation of a femoral tunnel is undertaken by either a traditional two-incision outside-in femoral guide or the novel femoral guide 12 of the present invention (see FIGS. 1 and 2).

Figure 4:
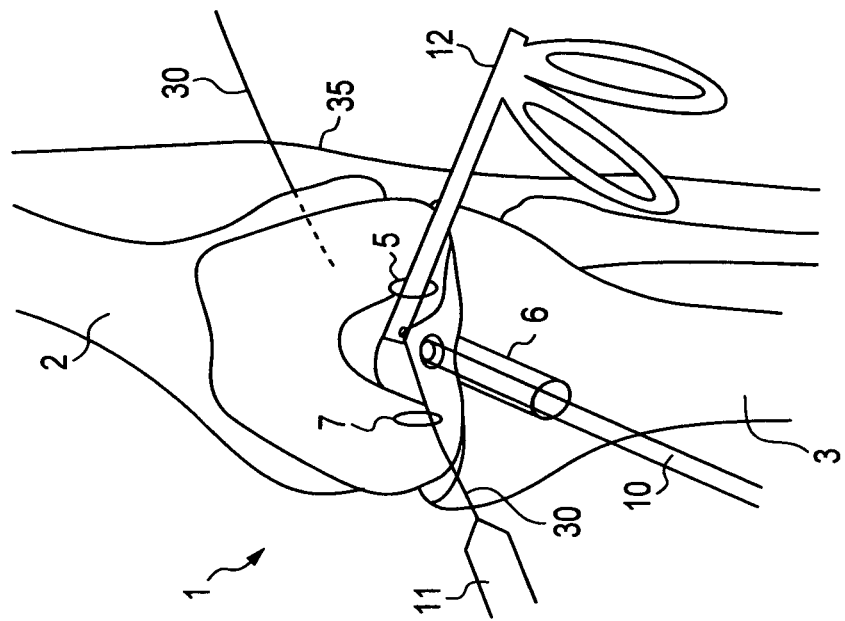
FIG. 4 is a schematic view of the disposition of a guide pin in the femur of a knee utilizing the femoral guide of claim 1 in accordance with the present invention.
Figure 5:
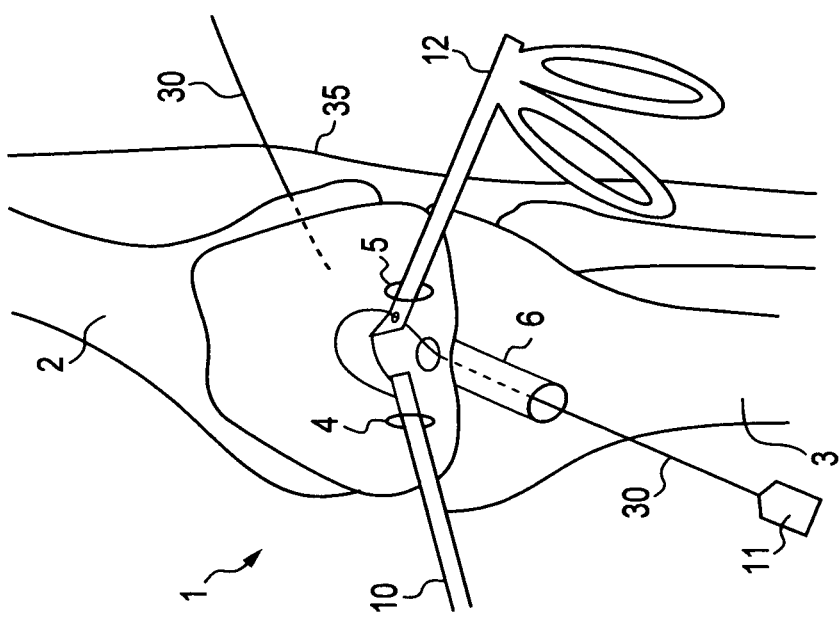
FIG. 5 is a schematic view of an alternative manner of disposing a guide pin in the femur of a knee utilizing the femoral guide of claim 1 in accordance with the present invention.

The femoral guide 12 can be used to create a single or multiple femoral tunnels 55 (see FIGS. 4, 5, and 6). The single femoral tunnel technique is performed as follows. With the arthroscope 10 viewing from either the traditional medial infrapatellar arthroscopic portal 4 or the tibial tunnel 6, a sharp-tipped guide pin 30 is inserted into the knee 1 from another portal, either the previously created tibial tunnel 6 or an accessory medial infrapatellar arthroscopic portal 7 (or similar separate medial percutaneous insertion). The femoral guide 12 is placed through the lateral infrapatellar arthroscopic portal 5 to grasp and direct the guide pin 30.

The femoral guide 12 is a handheld instrument with functional end 13, shaft 14 and scissor-action handle 15. In one version of this femoral guide 12, the functional end 13 has an adjustable calibrated reference tip 16 and a guide ring 17 with a mobile opening and closing arm 18. The adjustable calibrated reference tip 16 can shorten or lengthen to adjust the offset distance 19 between the tip 16 and the center of the guide ring 17. The offset distance 19 has a range from 2 to 20 mm, preferably 4 to 8 mm. The reference tip 16 may also swivel to allow it to point in different directions relative to the handle 15 and allow proper positioning of the guide 12 for left and right knees 1 with varying anatomy. The reference tip 16 may also extend and retract to allow variable offset distances 19. A single adjustable femoral guide 12 (as described), or several guides which are non-adjustable with respect to swivel directions or offset distances, can provide all of the necessary options.

A modified form 12A of the guide 12 is shown in FIG. 3. In the guide 12A, there is a semi-circular guide loop 20 attached to the functional end 13 on the opposite side from which the mobile arm 18 opens and closes. The radius distance 21 from the guide loop 20 to a point spaced apart from the center of the guide ring 17 is equal in all directions and has an adjustable range from 2 to 20 mm, preferably 4 to 8 mm. This version of the femoral guide may or may not have a reference tip 16. If there is no reference tip 16, the distal end of the guide loop 20 attaches to the end of the tool. If there is a reference tip, the distal end of the guide loop 20 attaches 1 to 2 mm short of the reference tip 16 such that the radius distance 21 is 1 to 2 mm smaller than the offset distance 19.

For both femoral guides 12 and 12A, the mobile arm 18 is controlled by the scissor-action handle 15. As the loops of the handle 15 are separated, the mobile arm 18 opens the guide ring 17. The handle 15 moves in the same plane as the mobile arm 18 and may lie on the opposite side, as shown in FIG. 3, or on the same side from the mobile arm 18. The shaft 14 of the femoral guide 12, or of the guide 12A, may range from 1 to 50 cm, preferably 10 to 20 cm. The guide ring 17 directs the spinning guide pin 30 into the femoral bone 2. The guide ring 17 and/or its bearing surfaces may consist of materials designed to resist surface wear, fatigue and fracture.

After femoral guide 12 is inserted into the knee 1 from the lateral infrapatellar portal 5, the handle 15 is opened manually to open the mobile arm 18. Once open, the femoral guide 12 is maneuvered to catch the sharp tip of the guide pin 30 in the guide ring 17. The handle 15 is then closed to close the mobile arm 18 and capture the guide pin 30 within the guide ring 17. With the captured guide pin 30, the femoral guide 12 is positioned with either the reference tip 16 over the back of the lateral femoral condyle 2 or the guide loop 20 overlying the anatomic position of the femoral attachment site of the ACL. The inner diameter of the guide ring 17 corresponds to the outer diameter of the guide pin 30 to allow it to direct the pin 30, yet allow it to spin freely. With the tip of guide pin 30 anatomically placed in the femoral attachment site of the ACL, the guide pin 30 is advanced with power drill 11 through the femoral guide 12 and femur 2 to exit the skin on the lateral thigh 35 of the patient. The handle 15 is opened manually to open the mobile arm 18 of the femoral guide 12 in order to release guide pin 30 and allow removal of femoral guide 12 from the knee 1. Alternatively, the guide pin 30 may be inserted just into the femoral bone 2 to create a blind-ended femoral tunnel 55.

Figure 8:
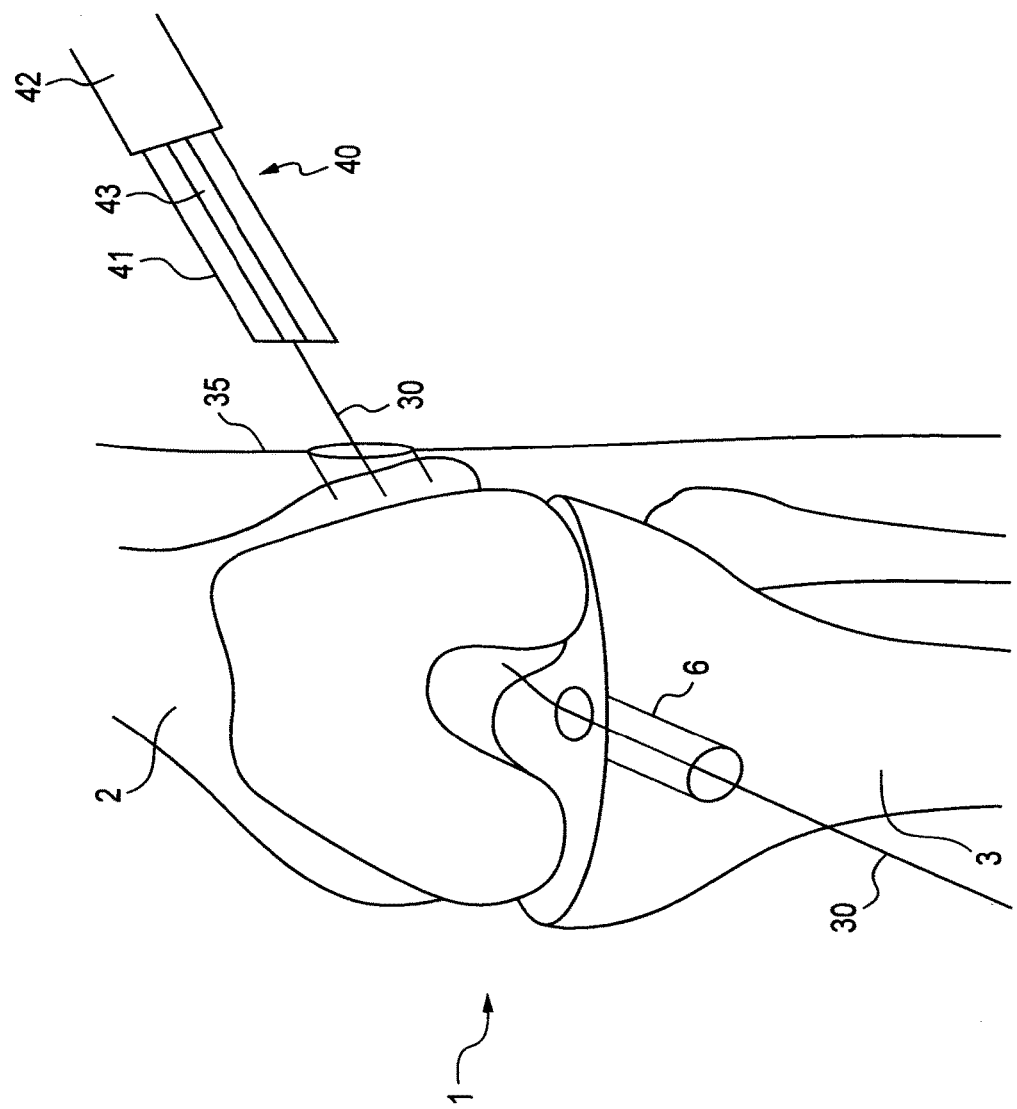
FIG. 8 is a schematic view of a manner of incising the skin and soft-tissue over a guide wire utilizing the cannulated scalpel of FIG. 7 in accordance with the present invention.

A cannulated disposable scalpel 40 is passed over the guide pin 30 exposed from the skin on the lateral thigh 35 to create a passage through the skin and soft-tissue to the lateral cortex of the femur 2 (see FIGS. 7, 8). The cannulated scalpel 40 consists of a leading sharp blade 41 and flat handle 42 with a central cannulation 43 to fit over the guide pin 30.

Figure 10:
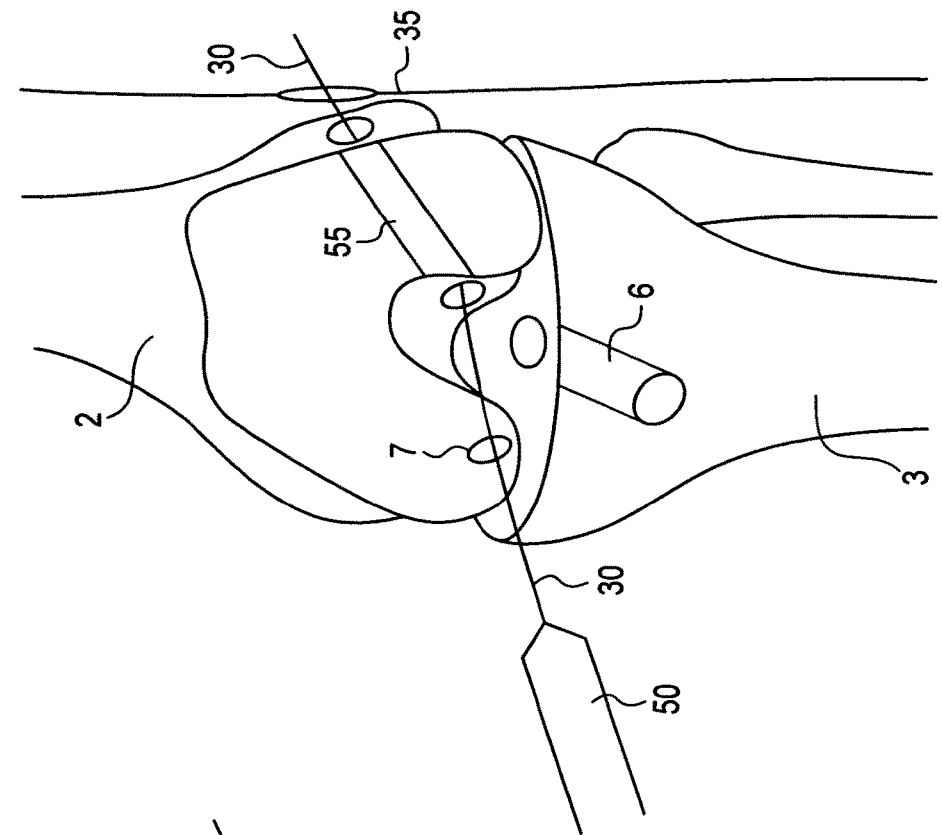
FIG. 10 is a schematic view of an alternative manner of creating a tunnel in a bone over a guide wire utilizing a cannulated reamer or drill in accordance with the present invention.
Figure 9:
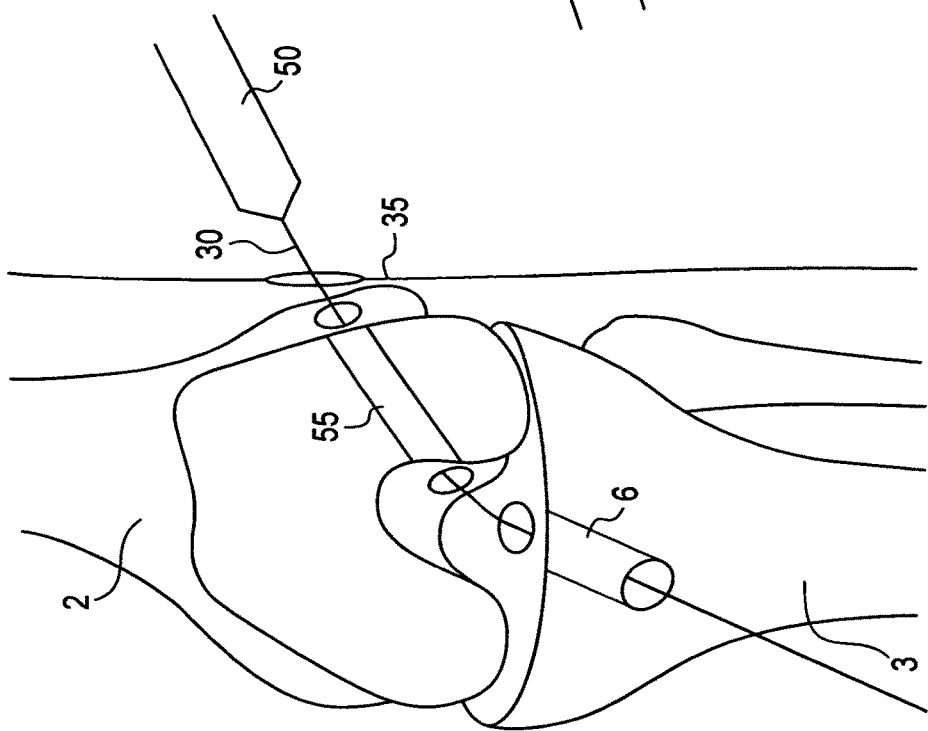
FIG. 9 is a schematic view of a manner of creating a tunnel in a bone over a guide wire utilizing a cannulated reamer or drill in accordance with the present invention.
Figure 11:
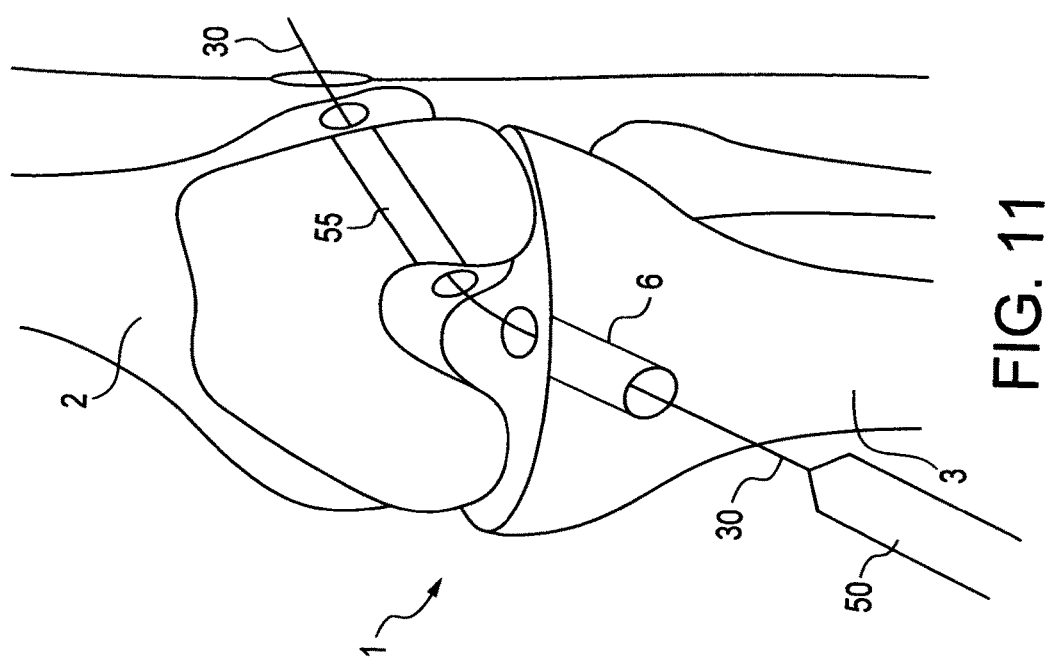
FIG. 11 is a schematic view of a second alternative manner of creating a tunnel in a bone over a guide wire utilizing a cannulated reamer or drill in accordance with the present invention.
Figure 15:
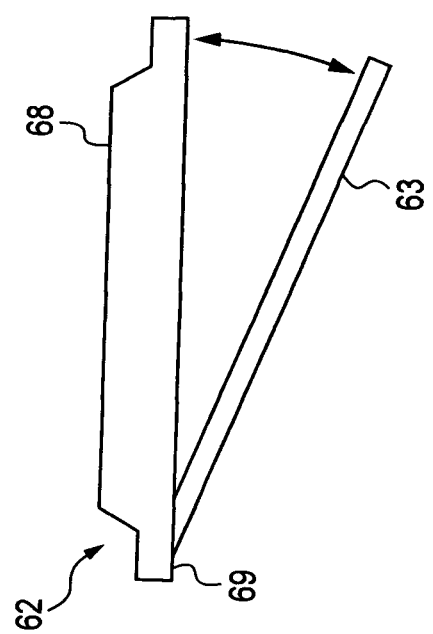
FIG. 15 is a side elevational view of the ring capture button of FIG. 14.
Figure 17:
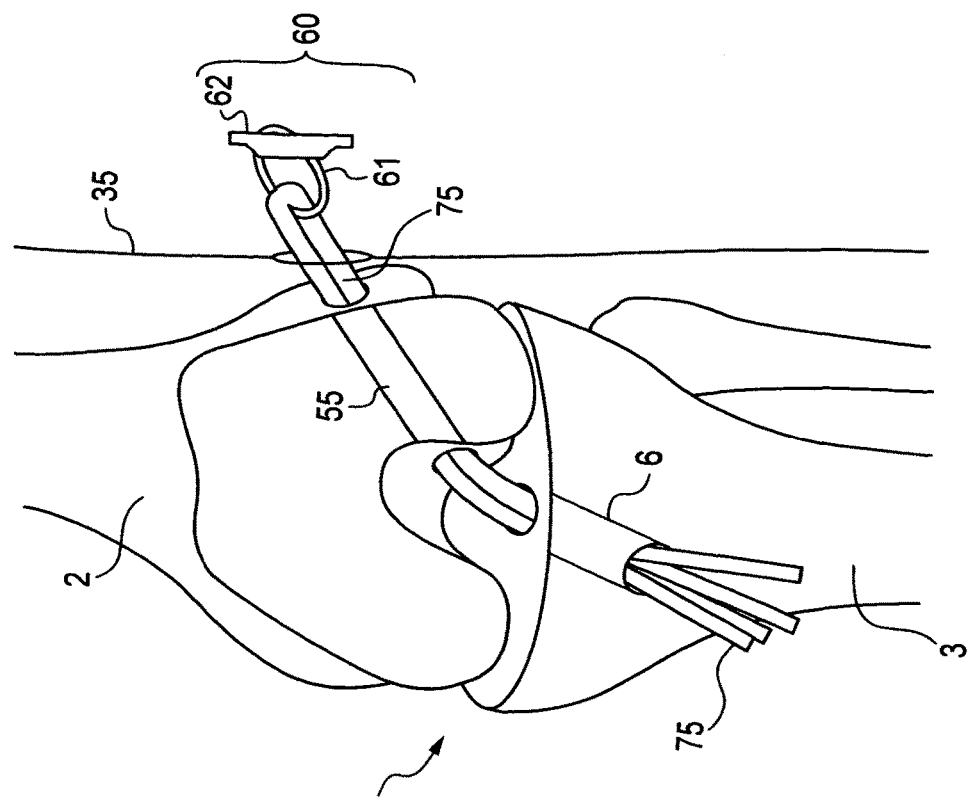
FIG. 17 is a schematic view of a manner of assembling the ring of FIG. 13 and the ring capture button of FIG. 14 in accordance with the present invention.
Figure 16:
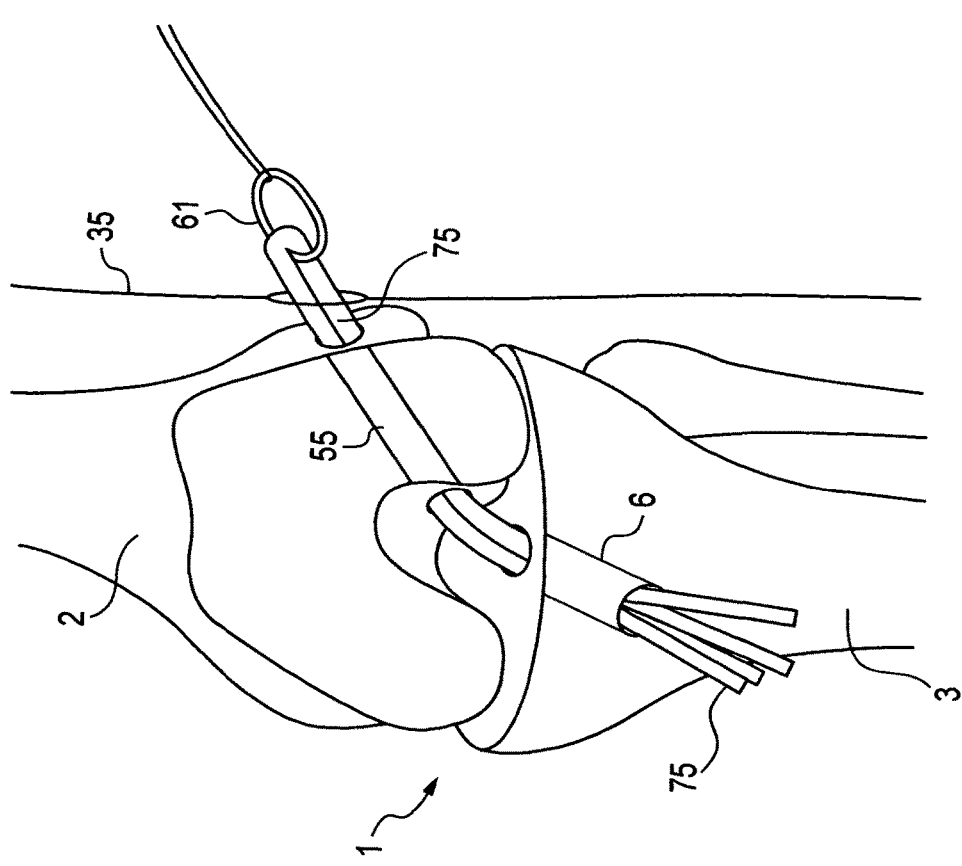
FIG. 16 is a schematic view of a manner of passing the ring of FIG. 13 along with a looped end of soft-tissue graft in accordance with the present invention.
Figure 19:
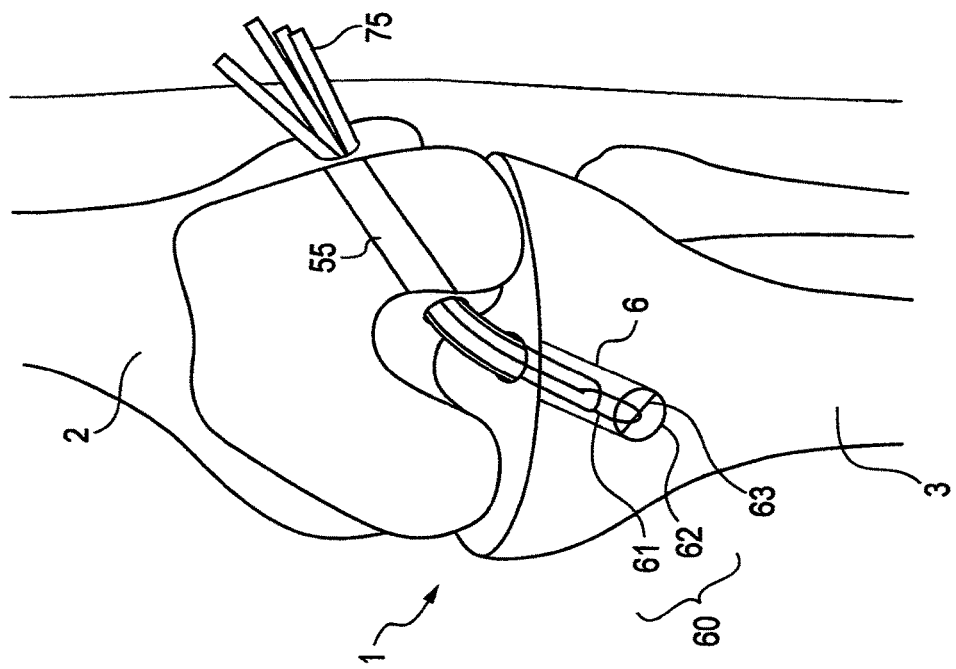
FIG. 19 is a schematic view of a manner of tibial placement of the surgical ring fixation tool of FIG. 12 in a knee in accordance with the present invention.
Figure 18:
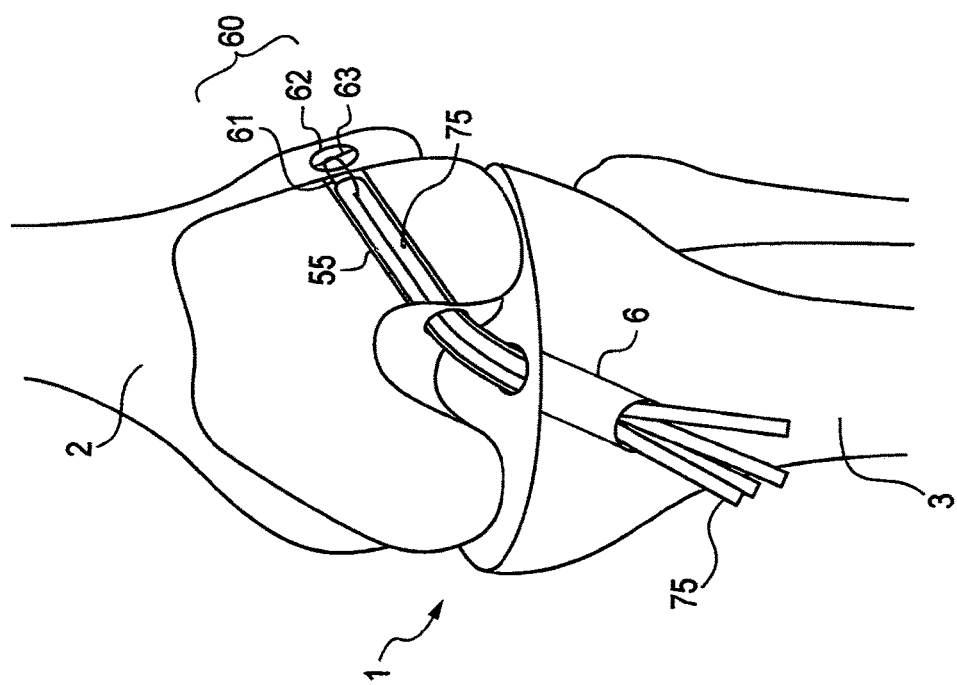
FIG. 18 is a schematic view of a manner of femoral placement of the surgical ring fixation tool of FIG. 12 in a knee in accordance with the present invention.

A flexible reamer 50 can be passed through the tibial tunnel 6 or accessory medial infrapatellar portal 7 in retrograde fashion over the guide pin 30 to create a femoral tunnel 55 through the bony lateral femoral condyle 2, or a rigid reamer 50 can be passed through the proximal lateral incision in antegrade fashion over the guide pin 30 to create the femoral tunnel 55, through the bony lateral femoral condyle 2 (see FIGS. 9, 10 and 11).

For the double or multiple femoral tunnel techniques, a conventional outside-in guide or femoral guide 12 can be used as described above to create two or more separate femoral tunnels 55. Guide pins 30 can be passed through either the accessory anteromedial arthroscopic portal 7 or the tibial bone tunnel 6 or both, and the remaining steps described above can be repeated, to create multiple separate tunnels 55. After the creation of the first femoral tunnel 55, the femoral guide 12 can be positioned to reference off previous tunnels to create additional femoral tunnels like tunnel 55.

For a bone-patellar tendon-bone graft or other bone-tendon composite grafts, the graft may be passed either retrograde or antegrade into the tunnels 6 and 55 using conventional techniques, and the bone end grafts may be fixed in their femoral tunnels 55 or tibial tunnels 6 with conventional cannulated interference screws.

For the hamstring graft or other soft-tissue grafts that can be folded to create a looped end, the novel surgical ring fixation tool 60 may be used to fix a graft in a bone tunnel (see FIGS. 12, 13, 14 and 15). The surgical ring fixation tool 60 consists of a ring 61 and a ring capture button 62. The ring 61 and the ring capture button 62 are made of durable materials which are either non-absorbable, bio-absorbable, or capable of bio-integration. The ring has width dimensions 65 ranging from 2 to 20 mm, preferable 4 to 12 mm, and length dimensions 66 ranging from 5 to 100 mm. The ring capture button 62 has a base member 72 which has an outer diameter 64 ranging from 5 to 25 mm, preferably 5 to 15 mm and an inner diameter 67 ranging from 2 to 20 mm, preferably 4 to 12 mm. The base member 72 of the ring capture button 62 has two separate surfaces, deep 68 and superficial 69. The ring capture button 62 also has a central capture bar 63 which allows capture of the ring 61. The deep surface 68 may possess bone adhesive properties or geometry. The deep surface 68 may also maintain a protruding shape to interface with either the tibial or femoral tunnel 6 or 55 openings. The superficial surface 69 is smooth to prevent overlying soft-tissue adhesion. The central capture bar 63 of the ring capture button 62 moves on a hinge and allows the capture bar 63 to freely swing open and closed on the superficial surface 69 side. The capture bar 63 stops at the base member 72 of the ring capture button 62 and cannot open towards the deep surface 68. The capture bar 63 stopping mechanism results from limitations on the hinge, mismatch between the capture bar length 70 and the member 72 inner diameter 67 or other stopping or locking mechanism. The geometry or other design features maintain the ring 61 centered in the opening of the base member 72 of the ring capture button 62.

For tibial 6 or femoral 55 tunnel graft fixation, the surgical ring fixation tool 60 can be used in accordance with the methods illustrated in FIGS. 16, 17, 18 and 19. The free ends of the soft-tissue grafts 75 are passed through the ring 61 so that equal lengths of soft-tissue grafts 75 protrude from each side of the ring 61. The ring 61, with the looped ends of the soft-tissue grafts 75, is passed either antegrade through the femur 2 and out the tibia 3, or retrograde through the tibia 3 and out through femur 2. After ring 61 and the looped ends of the soft-tissue grafts 75 are passed, the ring 61 is assembled with the ring capture button 62. Once assembled, the free ends of the soft-tissue grafts 75 are tensioned, thus drawing the surgical ring fixation tool 60 into position with its deep surface 68 up against either the tibial 3 or femoral 2 cortical bone surfaces. The outer diameter 64 of the base member 72 of the ring capture button 62 is larger than the tibial or femoral tunnels 6 and 55, respectively, restricting further advancement of the graft 75 and the surgical ring fixation tool 60 into knee 1.

Figure 20C:
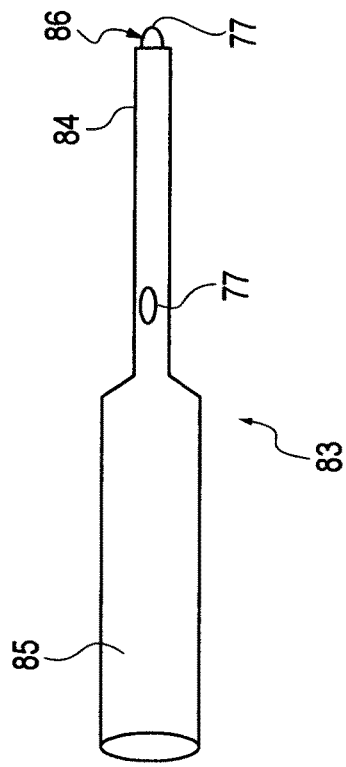
FIG. 20C is a perspective view of a suspension pin insertion tool in accordance with the present invention.
Figure 20A:
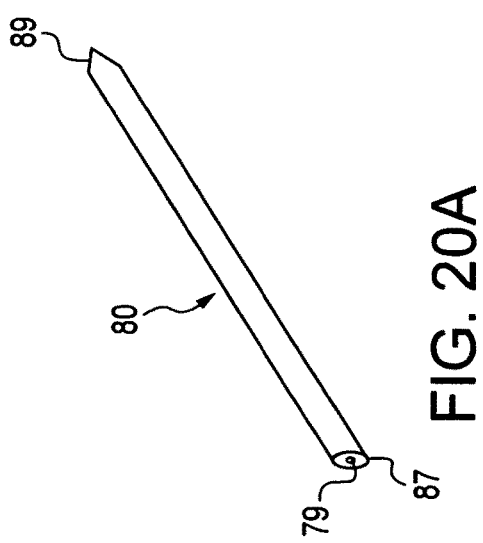
FIG. 20A is a perspective view of a suspension pin in accordance with the present invention.
Figure 20B:
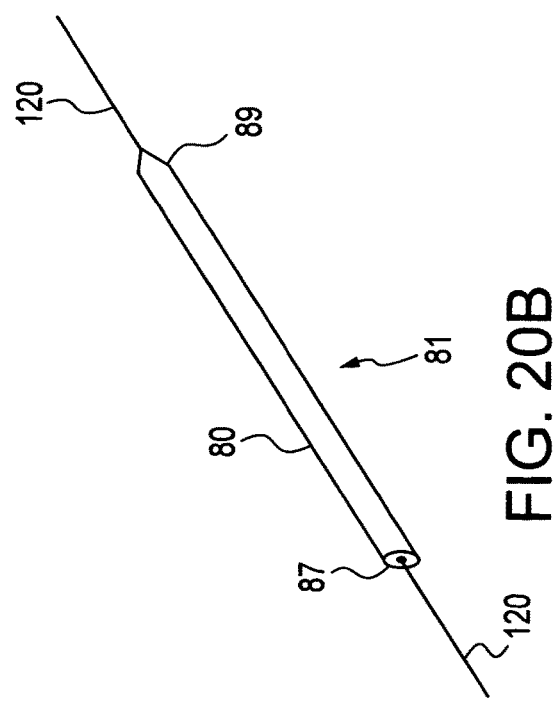
FIG. 20B is a perspective view of an alternative embodiment of a suspension pin in accordance with the present invention.
Figure 23A:
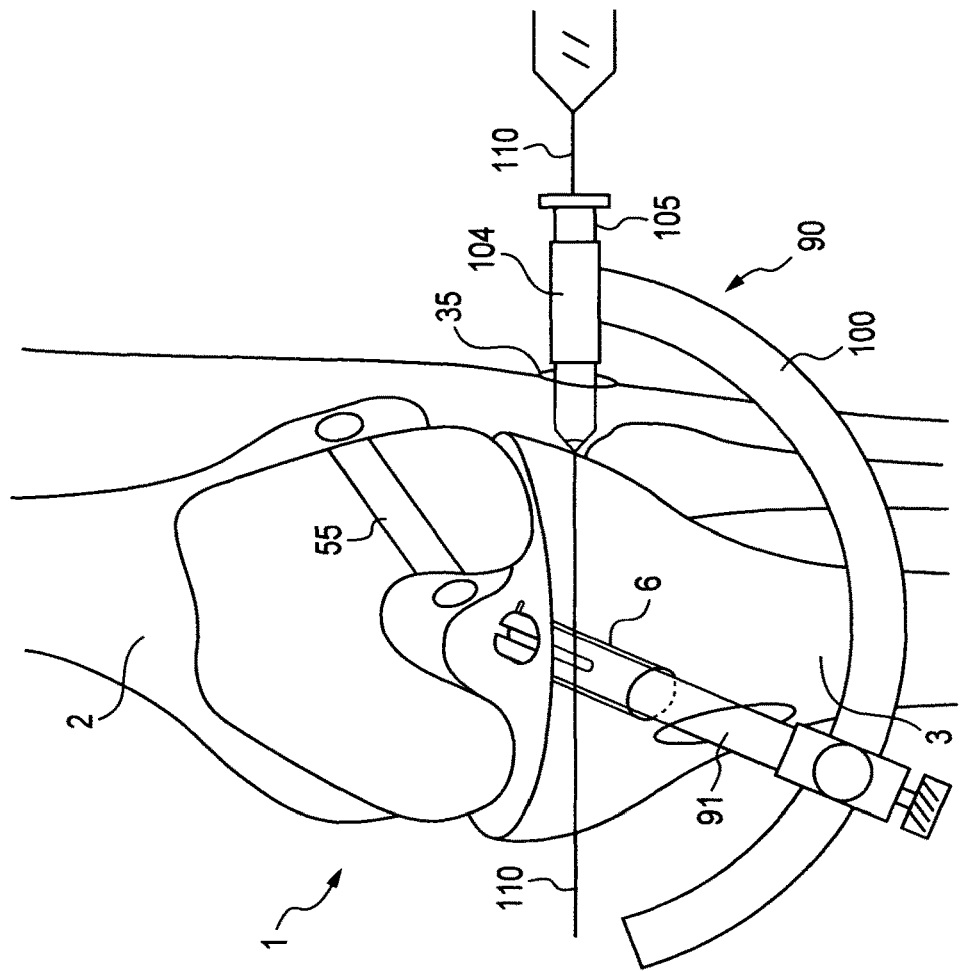
FIG. 23A is a schematic view of a manner of inserting the surgical guide pin shown in FIG. 22 across a bone tunnel in accordance with the present invention.

For a hamstring graft or other soft-tissue grafts which can be folded to create a looped end, the suspension pin 80 (or alternatively, the suspension pin 81) may be utilized to fix a graft in a bone tunnel (see FIGS. 20A and 20B). Such fixation is accomplished in the following manner. After creating the tibial tunnel 6 and the femoral tunnel 55, the surgical pin guide 90 is used to prepare for insertion of the suspension pin 80 (or, alternatively, of pin 81). The surgical pin guide 90 may be used on both the femur 2 and the tibia 3.

The guide 90 consists of three components, a target arm 91, a curved guide arm 100 and a bullet 105. The diameter of the target arm 91 may vary from 2 mm to 25 mm, preferably from 5 to 15 mm. Targeting tips 92 may be of various sizes. The tip 92 has an open target slot 94 at the target end ranging in depth from 0 to 100 mm, preferably 40 mm. Targeting tip 92 of the target arm 91 optionally has a small hook 93 protruding from its end. The small hook 93 protrudes up to 5 mm, but preferably about 2 mm. The small hook 93 may incorporate a mechanism to make the hook retractable.

The targeting tip 92 of target arm 91 may also include a groove 95 which allows for attachment of an elastic ring or open horseshoe-shaped ring 96 which can be attached at the site of the groove 95 to close the open end of target slot 94.

Target arm 91 may possess a mechanism to open or close the open end of the target slot 94, and it may also be calibrated to reference either direction along the target arm 91 from target point 97 in the target slot 94. Target point 97 is a consistent point in space along the target slot 94 to which a surgical guide pin 110 will be directed by the completely assembled surgical pin guide 90. Target point 97 is located a short distance from the end of the target tip 92 of the target arm 91 in the target slot 94. That distance may range from 0 to 100 mm, preferably 10 to 25 mm.

There is a target marker 98 on the surface of target tip 92, marking the level of the target point 97. The marker 98 may be radiographic, such as linear radio-opaque mark or a radiolucent hole, notch, or defect, which can be identified with conventional intraoperative radiographic techniques.

The surgical pin guide 90 also includes a curved guide arm 100 and aiming bullet 105. The curved guide arm 100 incorporates an aiming end 104 which allows for the attachment of an aiming bullet 105 and a separate mobile target arm attachment site 101. The mobile arm attachment site 101 moves freely along the curved arm guide 100 and its position can be secured by a locking mechanism 102. The curved arm guide 100 is calibrated with degrees to measure the angle between the aiming end 104 and the mobile target arm attachment site 101. With the target arm 91 attached to the mobile target arm attachment site 101 of the curved guide arm 100 and the aiming bullet 105 attached to the aiming end 104 of the curved guide arm 100, the surgical pin guide 90 is assembled. Thereafter, a surgical guide pin 110 may be passed through cannulation 106 in the aiming bullet 105, and the tip of the surgical guide pin 110 directed to the target point 97 located in the target slot 94 of the target guide 91.

After creating the tibial and femoral tunnels 6 and 55, the target arm 91 of the assembled surgical pin guide 90 is placed into a bone tunnel, preferably either the tibial tunnel 6 or the femoral tunnel 55. The target arm 91 can be placed in the bone tunnel in either an antegrade fashion (inside-out on the tibia 3, outside-in on the femur 2) or a retrograde fashion (outside-in on the tibia 3, inside-out on the femur 2). If the tunnels are co-linear, the target arm may traverse either the tibial tunnel 6 or the femoral tunnel 55 to be placed in the opposite tunnel, either 6 or 55. Conventional intraoperative radiographic techniques can assist with proper placement of the target arm 91 in the tunnels 6 and 55 by identifying the radiographic marker 98 overlying the target point 97. The mobile target arm attachment site 101 allows movement and proper positioning of the aiming end 104 of the curved guide arm 100 relative to either femur 2 or tibia 3 to provide a safe trajectory for the surgical guide pin 110. Once in proper position, a small incision is made in the skin and soft tissue in-line with the cannulation 106 of the aiming bullet 105. The aiming bullet 105 within its connection 104 to the curved guide arm 100 is advanced down the bony surface of either femur 2 or tibia 3.

Figure 22:
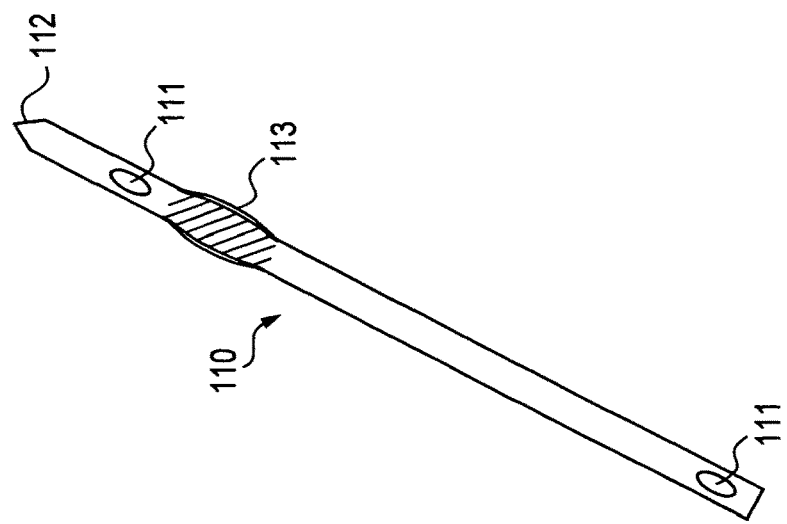
FIG. 22 is a perspective view of a surgical guide pin in accordance with the present invention.
Figure 23B:
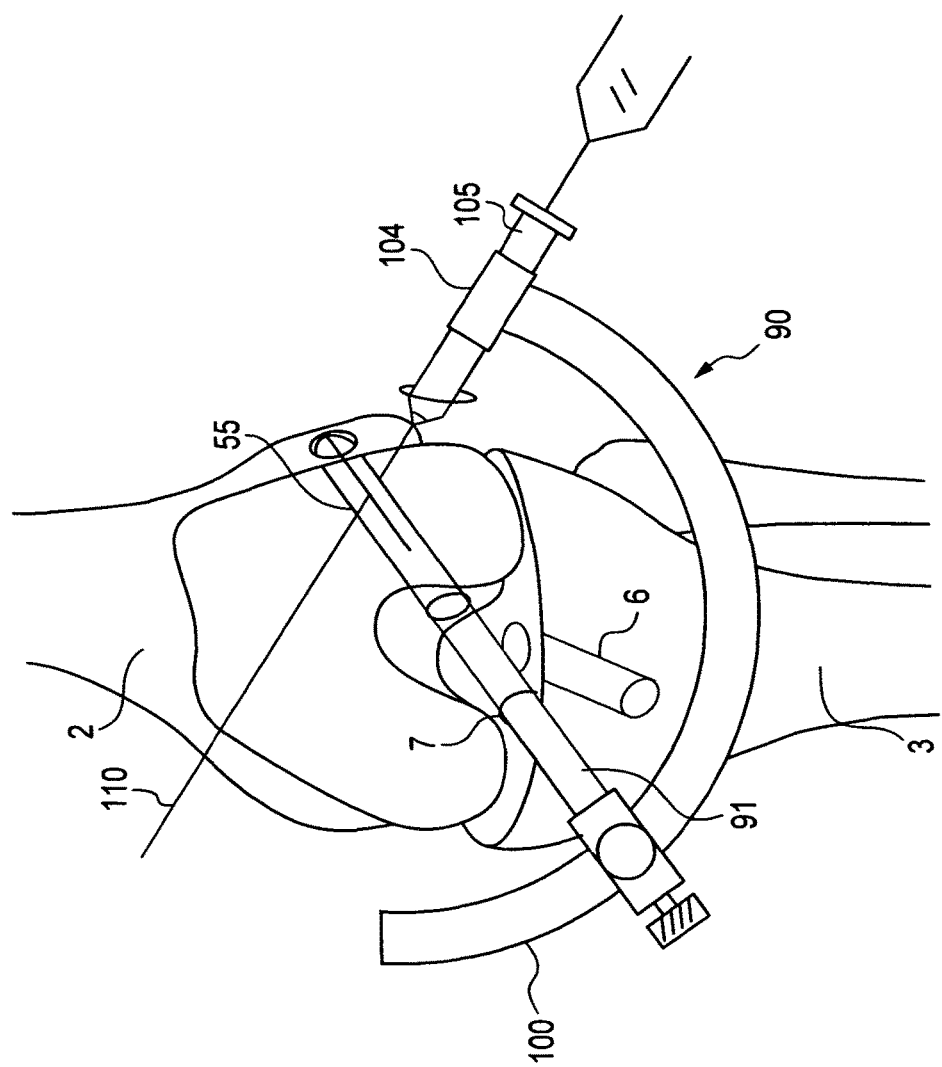
FIG. 23B is a schematic view of a manner of inserting the surgical guide pin shown in FIG. 22 across a bone tunnel in accordance with the present invention.
Figure 24A:
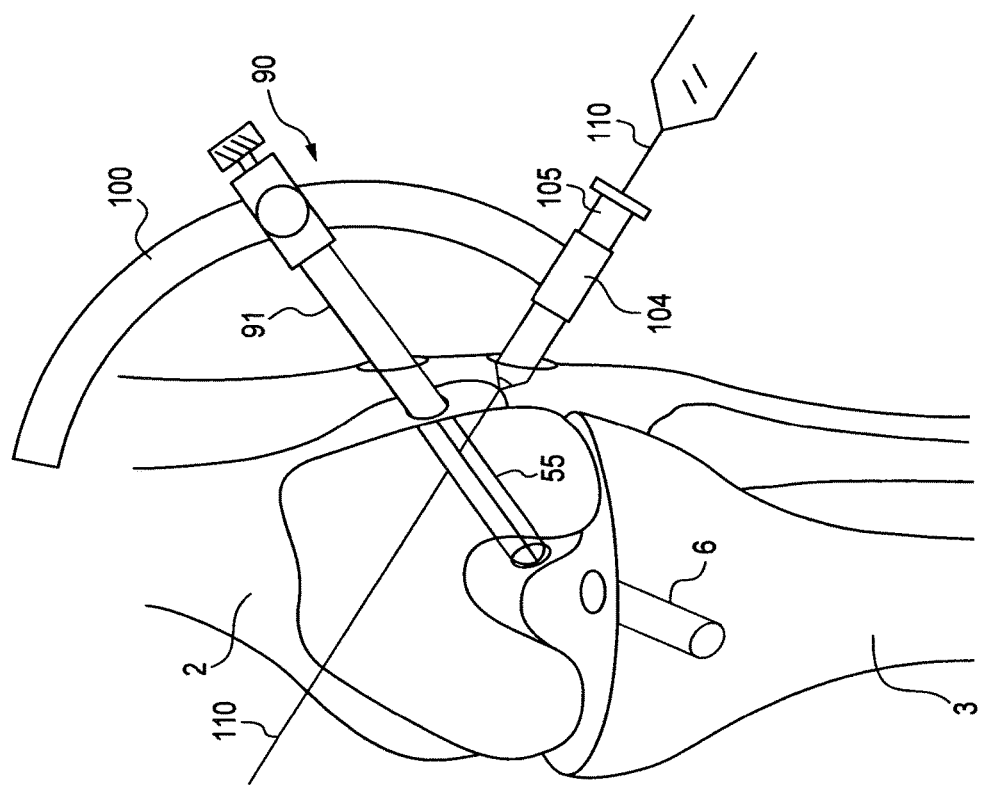
FIG. 24A is a schematic view of an alternative manner of inserting the surgical guide pin shown in FIG. 22 across a bone tunnel in accordance with the present invention.
Figures 24B, 24C:
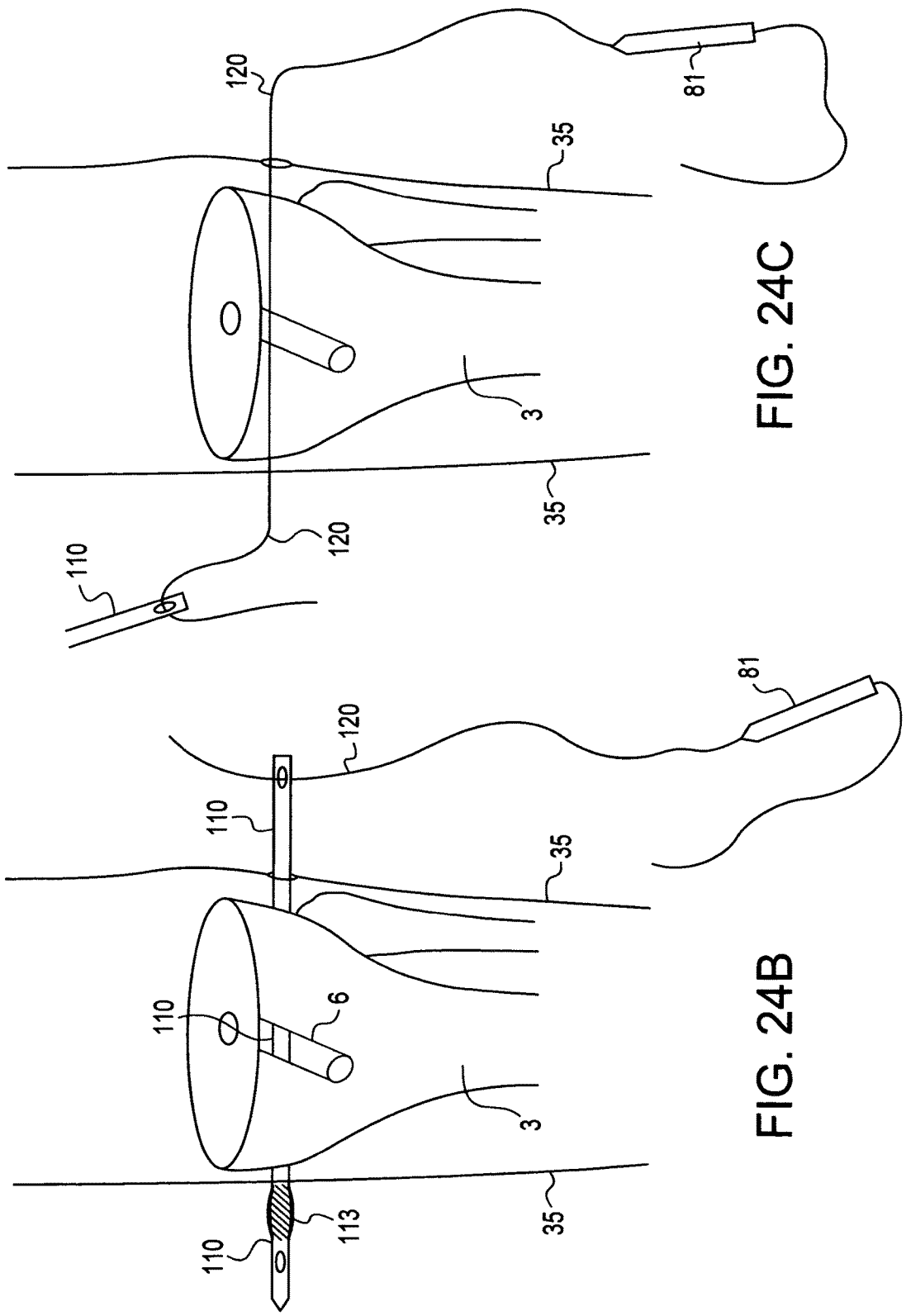
FIG. 24B is a schematic view of a flexible wire attached to the surgical guide pin of FIG. 22 traversing a bone tunnel in accordance with the present invention.
FIG. 24C is a schematic view of a manner of exchanging the surgical guide pin shown in FIG. 22 with the flexible wire of the suspension pin of the present invention.
Figure 26:
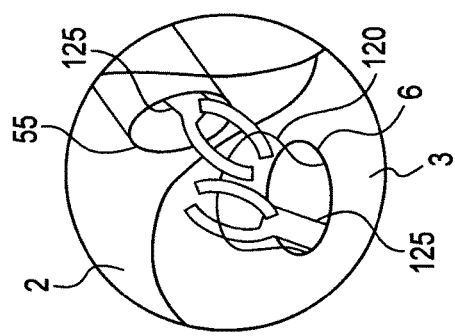
FIG. 26 is a sectional view of FIG. 25C showing the wire passing tool of FIG. 25A passing the central loop of flexible wire in the manner illustrated in FIG. 25C.
Figure 25C:
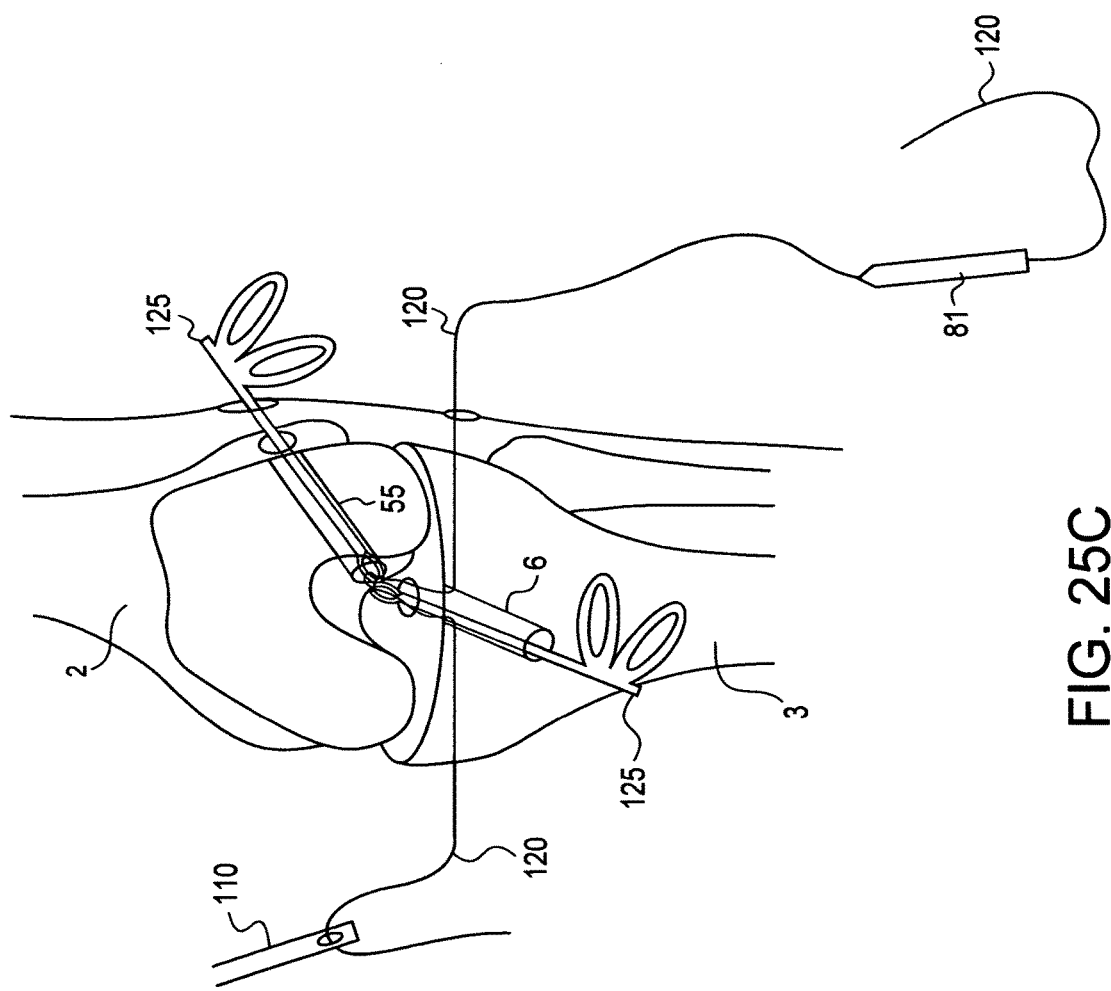
FIG. 25C is a schematic view of a manner of utilizing the wire passing tool shown in FIG. 25A to pass a central loop of flexible wire from a tunnel in a bone out through a tunnel in another bone in accordance with the present invention.
Figure 27:
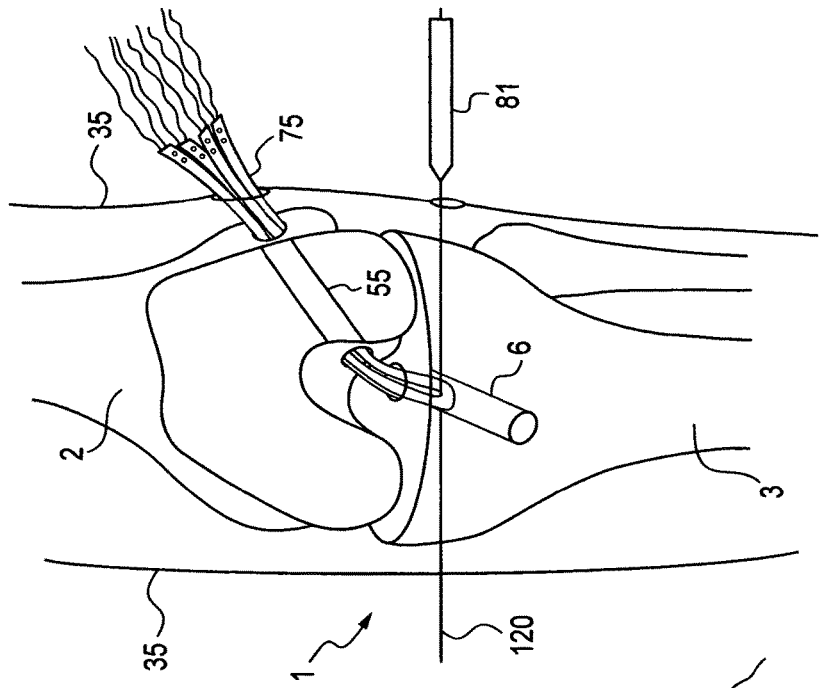
FIG. 27 is a schematic view of a manner of loading a free soft-tissue graft into a central loop of a flexible wire in accordance with the present invention.

Using power drill 11, the surgical guide pin 110 is advanced through the cannulation 106 in the aiming bullet 105 through the skin 35, soft tissue, and bone of the femur 2 or tibia 3 until both ends of the surgical guide pin 110 extend outside the knee 1 and its bone, soft-tissue, and skin (see FIGS. 23A, 23B, 24A, and 66). The surgical guide pin 110 possesses cannulations or slots 111, preferably two or more, and a sharp leading tip (see FIG. 22). The slots 111 preferably are positioned near the opposite ends of the surgical guide pin 110.

The surgical guide pin 110 may possess a region of slightly increased diameter with a cutting surface 113, preferably near its leading tip 112 but situated between the cannulations or slots, 111. As this region 113 is passed completely through the bone, it cuts a slightly larger diameter than the diameter of the other portions of the surgical guide pin 110 to assist with the passage of flexible wire 120 to be described later. Cannulated drills, reamers and/or taps may be passed over either end of the surgical guide pin 110 and used to prepare either the femoral 2 or tibial 3 bone for later passage of the novel suspension pin 80 or 81. These drills, reamers, and/or taps may be calibrated to assist in determining the size of the suspension pin 80 or 81 to be used. The surgical guide pin 110 may also be calibrated to assist in determining the size of the suspension pin, referencing from the aiming bullet 105 against the femoral or tibial bones 2 and 3. Surgical pin guide 90 can be removed from knee 1.

Flexible guide wire 120 is exchanged, using surgical guide pin 110, by connecting an end of the wire to one of the exposed ends of the guide pin 110 and withdrawing guide pin 110 by its other exposed end to pull flexible wire 120 into position (see FIGS. 24B, 24C, 24D and 24E). The guide pin 110 has cannulations or slots 111 running perpendicular to the long axis of the pin near either of both of its ends. One method of making the flexible wire exchange using the guide pin 110 is to pass the guide pin 110 as previously described and advance a few centimeters of the flexible wire 120 through either of the exposed slots 111. The guide pin 110 is then withdrawn by its opposite end, pulling flexible wire 120 into its previous position.

Figure 28:
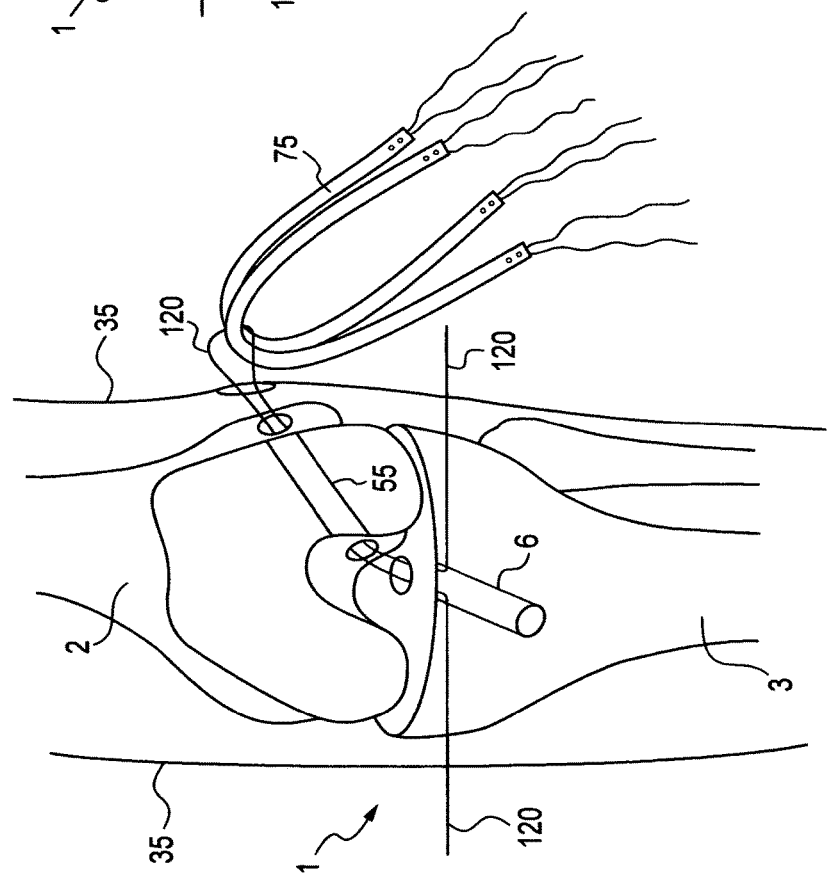
FIG. 28 is a schematic view of a manner of straightening and advancing a flexible wire to draw the loop end of a free soft-tissue graft through a tunnel in a bone into a tunnel of another bone in accordance with the present invention.
Figure 36:
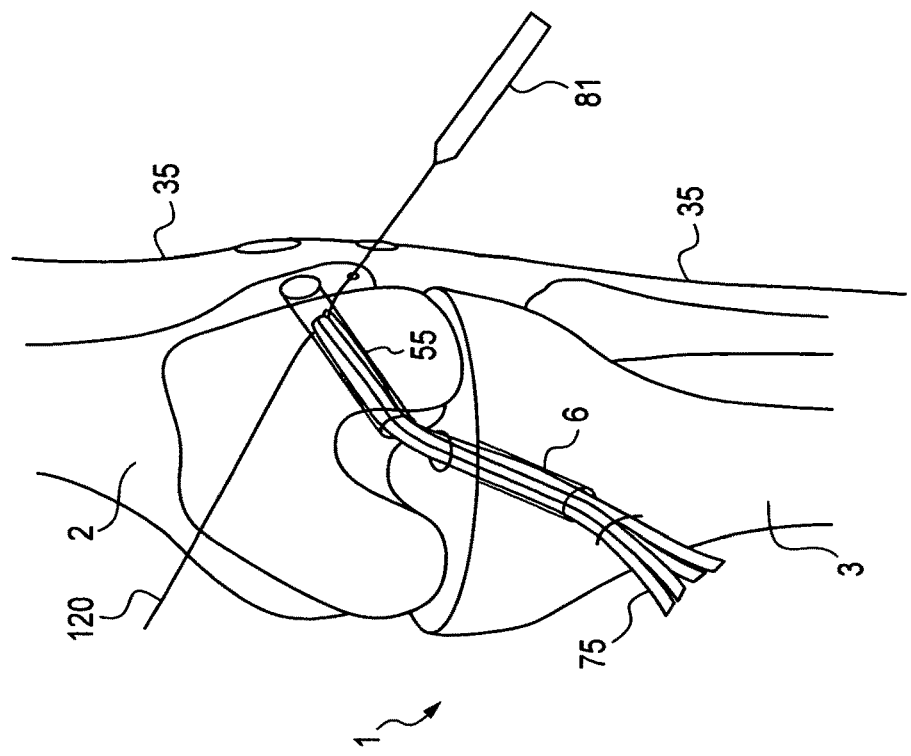
FIG. 36 is a schematic view of a manner of straightening and advancing a flexible wire to draw the loop end of a free soft-tissue graft through a tunnel in a bone into a tunnel of another bone in accordance with the present invention.
Figure 35:
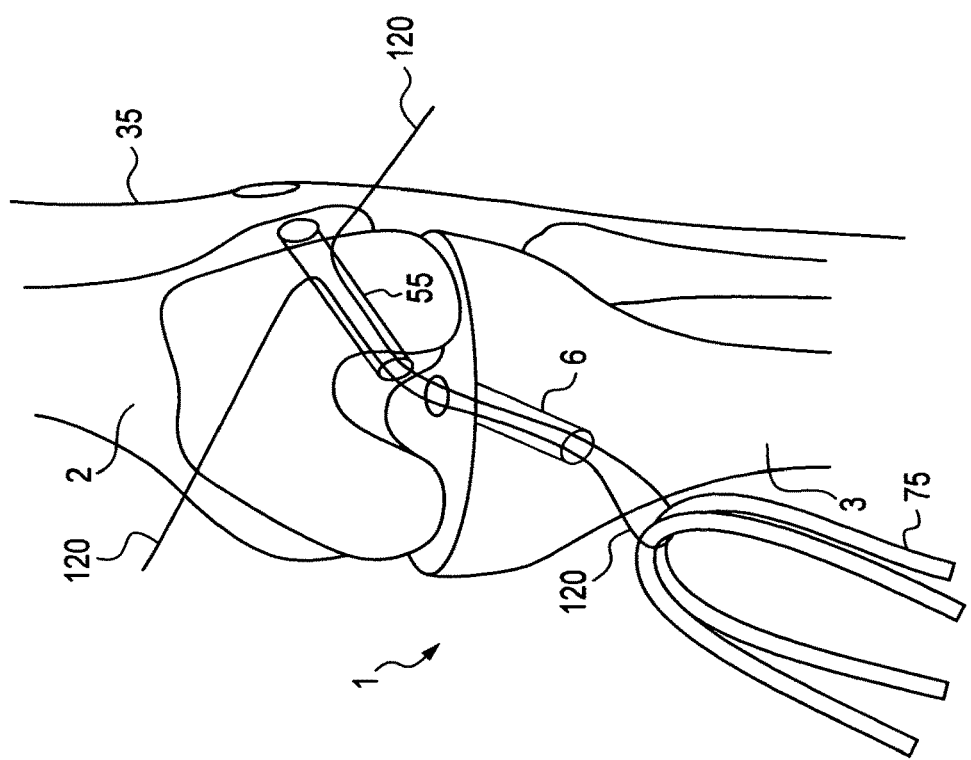
FIG. 35 is a schematic view of a manner of loading a free soft-tissue graft into a central loop of flexible wire in accordance with the present invention.
Figure 37B:
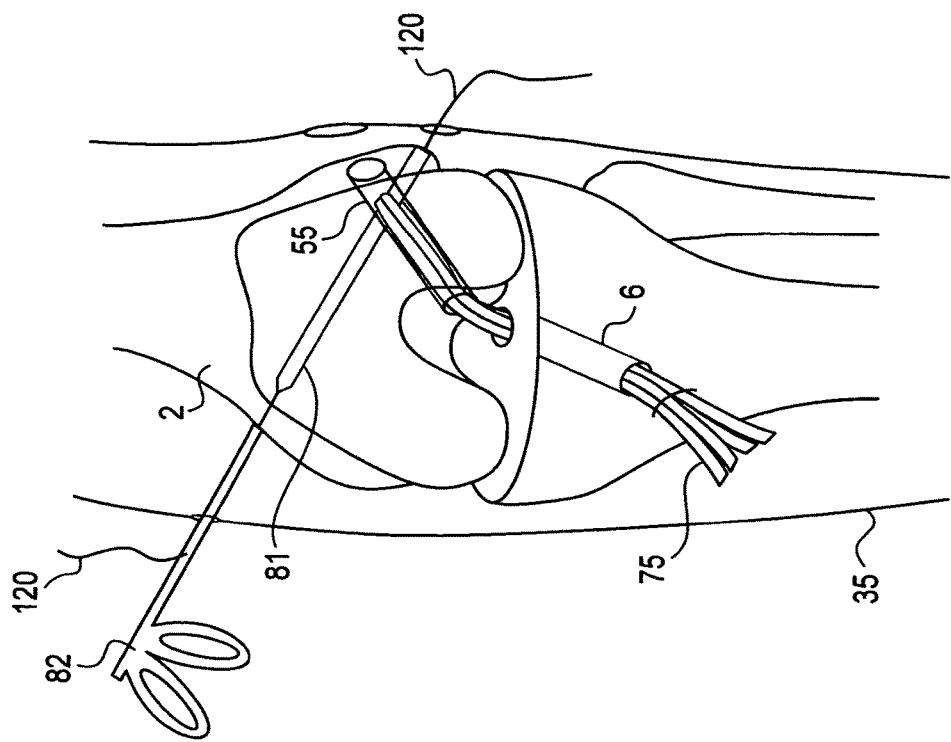
FIG. 37B is a schematic view of a manner of cutting a flexible wire from a suspension pin of this invention utilizing the wire cutting tool shown in FIG. 20D in accordance with the present invention.
Figure 37A:
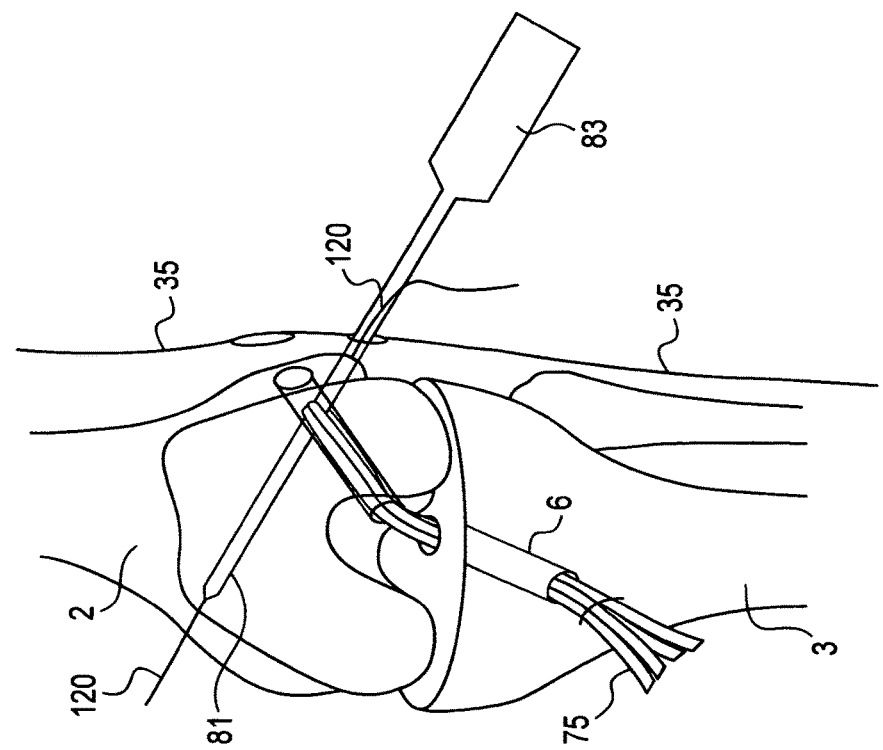
FIG. 37A is a schematic view of a manner of inserting the suspension pin shown in FIGS. 20A and 20B utilizing the suspension pin insertion tool shown in FIG. 20C to secure a loop end of a free soft-tissue graft in a bone tunnel in accordance with the present invention.

Using wire passing tool 125, a central loop of the flexible guide wire 120 can be drawn outside of knee 1 through either of the femoral or tibial tunnels 55 or 6 which is opposite to the tunnel which wire 120 initially traversed as shown in FIGS. 25A, 25B, 25C, 26, 29, 33, 34 and 67. The wire passing tool 125 consists of a long thin shaft 128 and a handle with a scissor-like mechanism 127 which controls the opening and closing of the claw-like wire-grasping tip 126. Alternatively, an elastic ring or open horseshoe-shaped ring 96 can be attached to close the open end of the target slot 94 of surgical pin guide 90. Using the closed end, the exchanged flexible wire 120 is drawn out of the tunnel with the target arm 91 of the surgical pin guide 90 to help facilitate the passage of the flexible wire 120. Free ends of soft-tissue grafts 75 are passed through the exposed central loop of flexible wire 120 so that equal lengths of soft tissue grafts 75 protrude from each side of the loop, as illustrated in FIGS. 27, 30, 35 and 68. Then, the free ends of flexible wire 120 outside of knee 1 are pulled to straighten flexible wire 120 and reduce the central loop of the soft-tissue grafts 75 through one of the tunnels 6 or 55 and into the opposite tunnel 6 or 55, as illustrated in FIGS. 28, 31 and 36.

Figure 30:
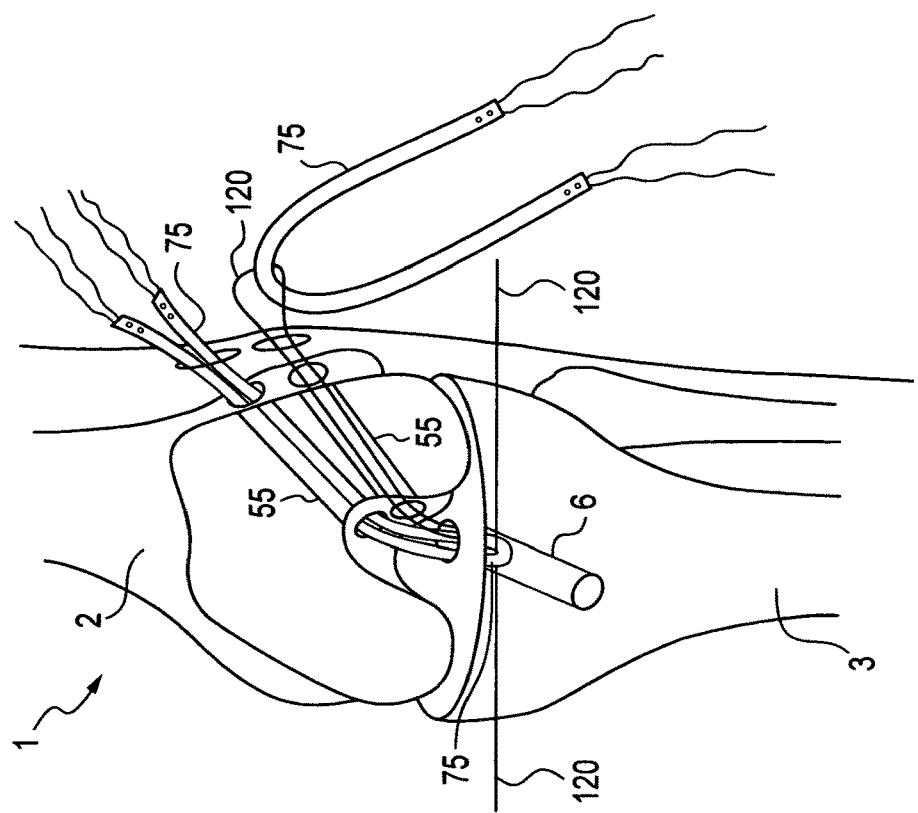
FIG. 30 is a schematic view of a manner of loading a free soft-tissue graft into a central loop in a flexible wire in accordance with the present invention.
Figure 29:
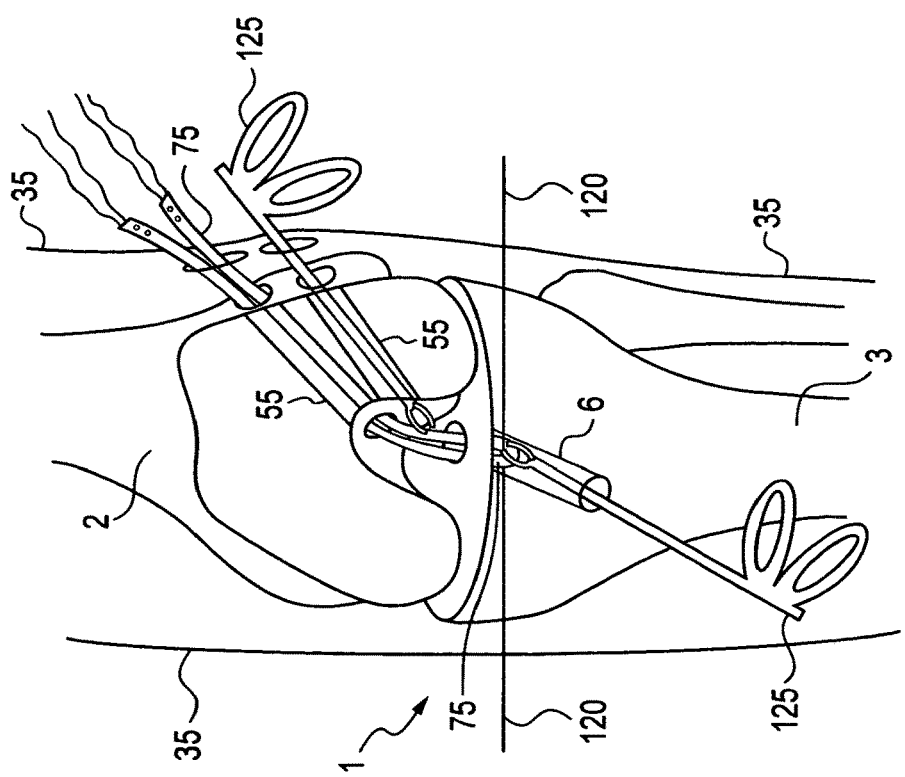
FIG. 29 is a schematic view of a manner of making an additional pass of a central loop of flexible wire from a tunnel in a bone out through an additional tunnel in another bone in accordance with the present invention.
Figure 32A:
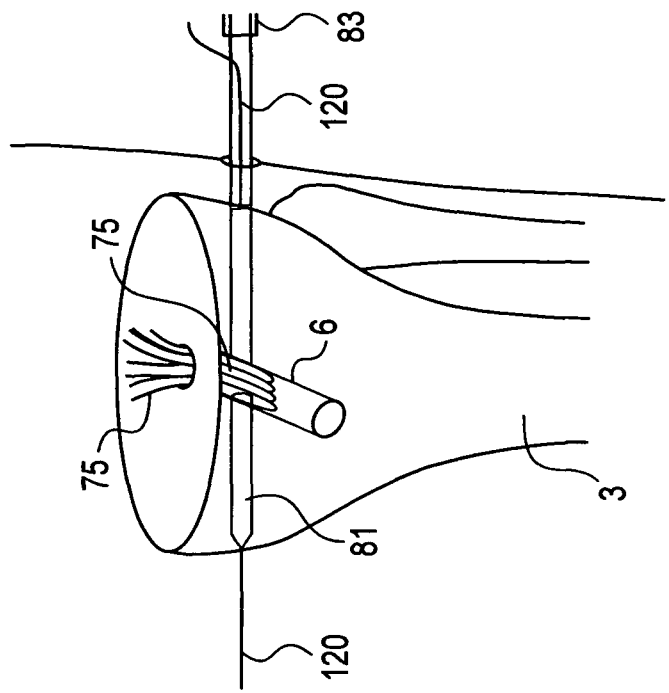
FIG. 32A is a schematic view of a manner of inserting the suspension pin shown in FIGS. 20A and 20B using the suspension pin insertion tool shown in FIG. 20C in accordance with the present invention.
Figure 31:
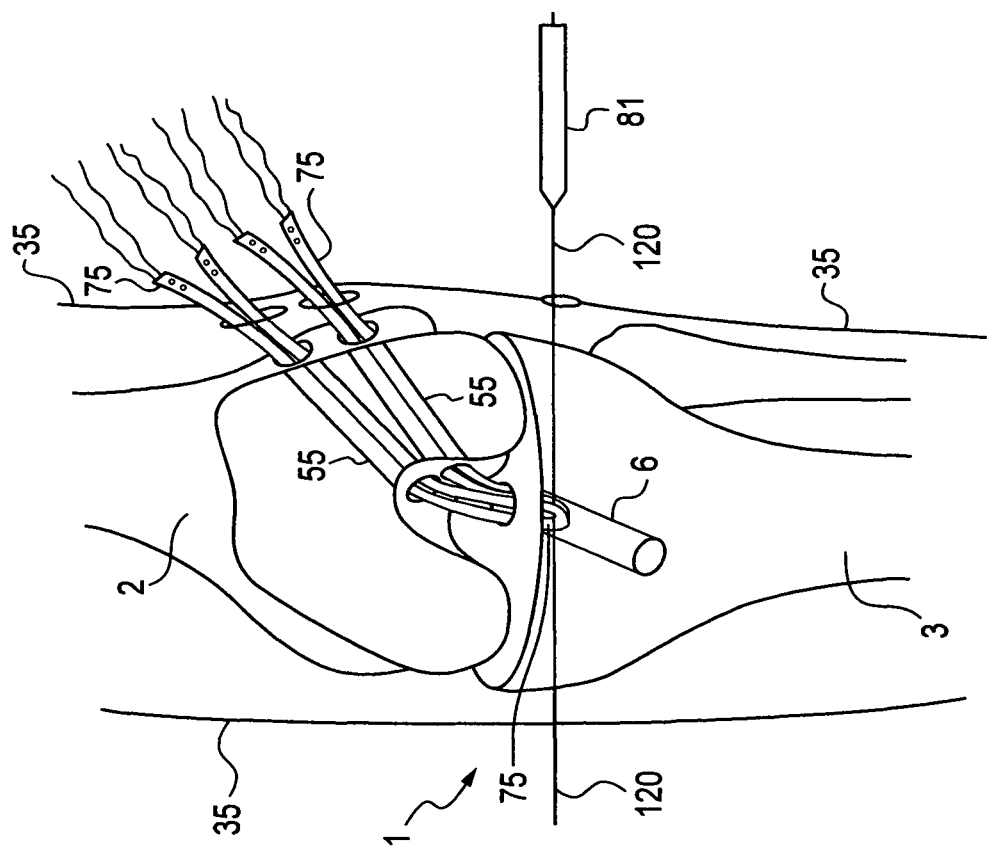
FIG. 31 is a schematic view of a manner of straightening and advancing a flexible wire to draw a loop end of a second free soft-tissue graft through a second tunnel in a bone into a tunnel of another bone in accordance with the present invention.
Figure 32C:
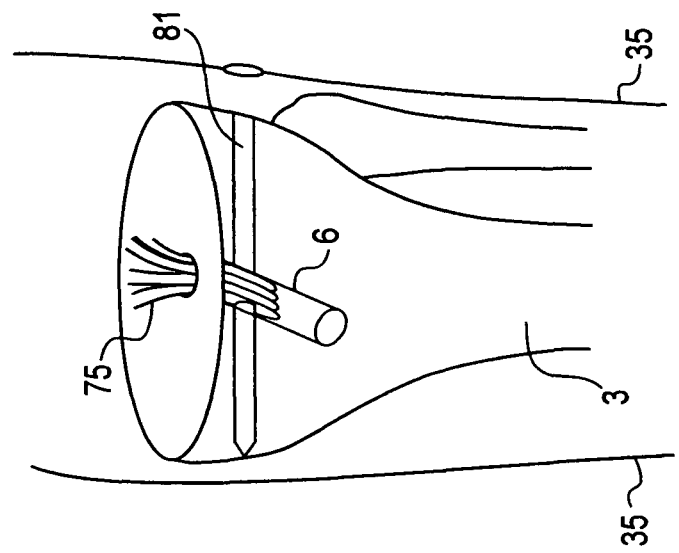
FIG. 32C is a schematic view of a manner of inserting the suspension pin shown in FIGS. 20A and 20B to secure a loop end of a free soft-tissue graft in a bone tunnel in accordance with the present invention.
Figure 32B:
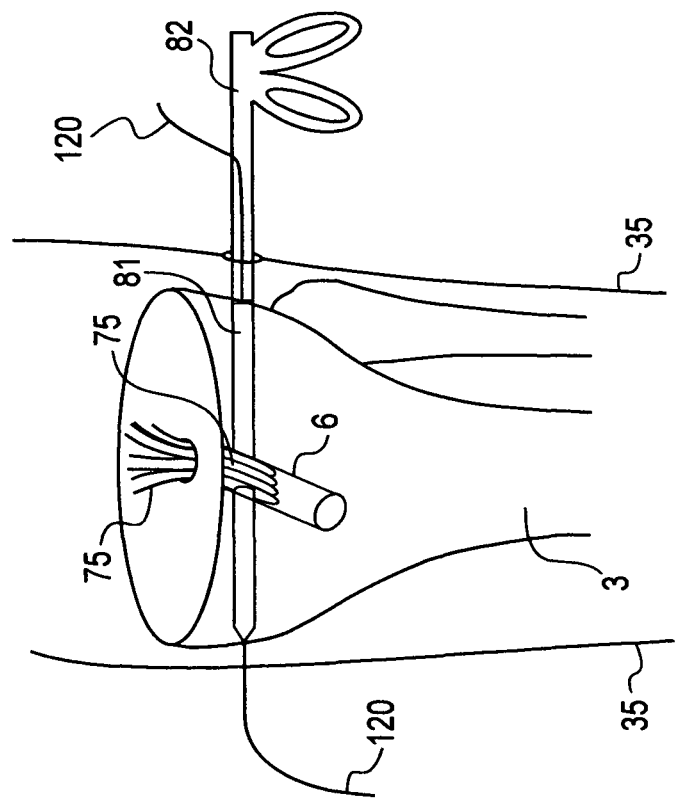
FIG. 32B is a schematic view of a manner of cutting a flexible wire from the end of a suspension pin of this invention utilizing the wire cutting tool shown in FIG. 20D in accordance with the present invention.
Figure 34:
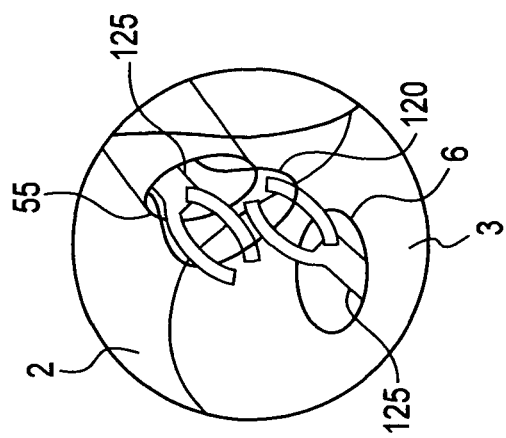
FIG. 34 is a sectional view of FIG. 33 showing the passage of the central loop of flexible wire illustrated in FIG. 33.
Figure 33:
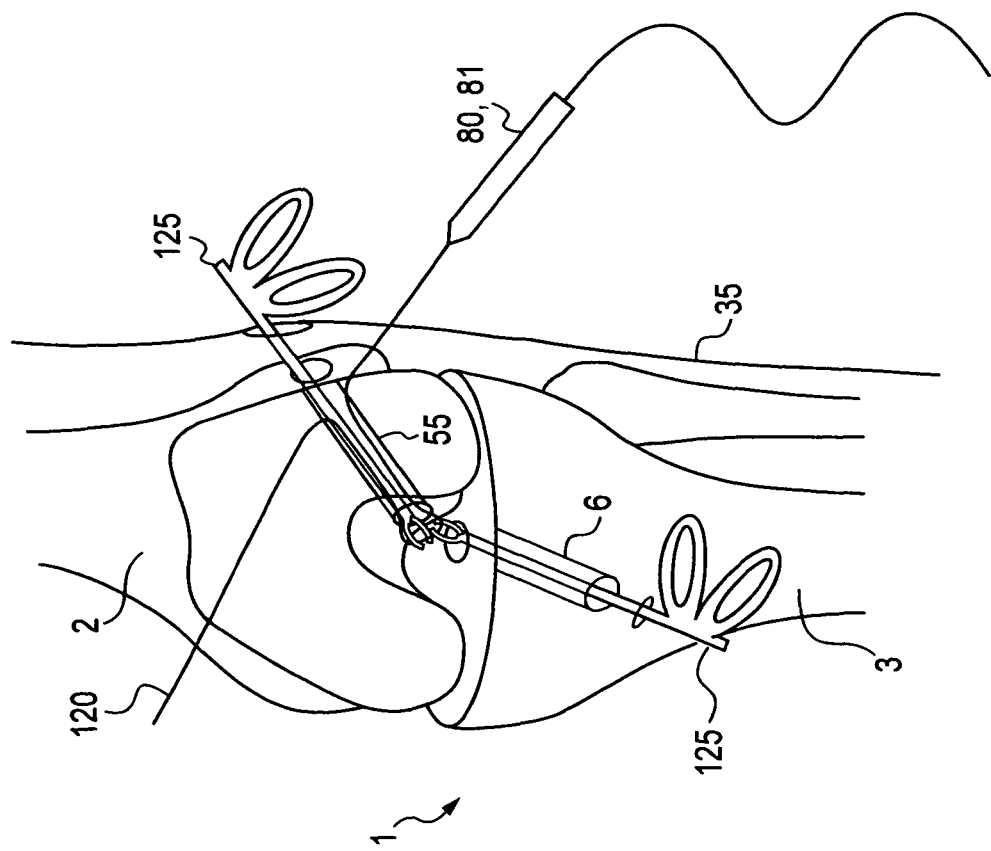
FIG. 33 is a schematic view of an alternative manner of passing a central loop of flexible wire from a tunnel in a bone out through a tunnel in another bone in accordance with the present invention.

If there are two or more tunnels on the opposite side of the knee from the tunnel traversed by the flexible wire 120, the steps described above can be repeated by individually passing the same central loop of wire 120 out of the remaining empty tunnel, loading another graft 75A, and re-straightening wire 120 to reduce the additional loop of soft-tissue graft through the additional tunnel into the initial tunnel traversed by the flexible wire 120, as illustrated in FIGS. 29, 30 and 31.

With flexible wire 120 straight and the soft-tissue graft 75 in position within both the femoral tunnel 55 and the tibial tunnel 6, novel suspension pin 80, or alternatively, novel suspension pin 81, is inserted, using the suspension pin insertion tool 83, into either femur 2 or tibia 3, replacing the position of the flexible wire 120, traversing either the femoral tunnel 55 or the tibial tunnel 6, and securing the loop end of soft-tissue graft 75, as illustrated in FIGS. 20A, 20B, 31, 32A, 36, 37A, 69.

There are two versions, 80 and 81, of the novel suspension pin which are shown in FIGS. 20A and 20B, respectively. The pin 80 is a cannulated pin not yet assembled on the flexible guide wire 120, and the pin 81 is already assembled as a unit on wire 120. The cannulated suspension pin 80 has a central longitudinal cannulation 79 which allows the pin to be engaged on the wire, and, thus mounted, inserted within either the femur 2 or the tibia 3 and across either the femoral tunnel 55 or the tibial tunnel 6 to secure the looped end of the soft-tissue graft 75 in position. Pin 81 is already assembled with the flexible wire 120 component, either freely moving over it by a cannulation 79 or fixed in place upon the wire 120 at a site or assembled with two separate flexible wire 120 components, one attached each end of the pin's body component.

Pin 80 and pin 81's body component are longitudinal pins of mostly uniform diameter corresponding to that of the widest diameter of the surgical guide pin 110. Alternatively, the diameter of the pins may vary and the outer surfaces may possess different geometry and bone adhesive properties (such as threads of a screw) to assist with fixation in the bone. The length of pin 80, and of the body component of pin 81, may vary, ranging up to 200 mm, but preferably from 40 mm to 100 mm. The pins are made of durable materials which are either non-absorbable, bio-absorbable, or capable of bio-integration. Pin 80 and pin 81's body component each possess a pointed end 89 and a rear end 87. The rear end 87 has specialized geometry which interfaces with inverse geometry on tip 86 of the suspension pin insertion tool 83.

Insertion tool 83 includes a handle 85, a shaft 84; and an insertion tip 86 which incorporate a cannulation 77, as shown in FIG. 20C. The cannulation 77 allows the tool 83 to be placed on the flexible wire 120 to guide the insertion of a suspension pin such as pin 80 or its alternate, pin 81. The handle 85 allows a surgeon to provide manual insertion forces with his hands or with an instrument such as a mallet. The tip 86 includes specialized geometry which interfaces with an inversely geometrical surface on the rear end 87 of suspension pin 80 or its alternate, pin 81 to prevent tip 86 from disengaging from rear end 87 during the pin insertion process.

Flexible wire 120 and the flexible wire 120 components of pin 81 preferably are made of durable materials which are non-absorbable, bio-absorbable, or capable of bio-integration, but they may also be made of materials which are similar to other commercially available surgical wires or sutures.

After the suspension pin 80 (or its alternate, pin 81) is secured in either femur 2 or tibia 3, the flexible wire 120 is removed from the cannulation 79. When a wire 120 component is fixed to a suspension pin 81, a wire cutter 82 with cannulation 78 is placed on the flexible wire 120 and inserted through skin 35 and soft-tissue to the bone surface of either femur 2 or tibia 3, as illustrated in FIGS. 20D, 32B, 32C and 37B. Handle 15 of the cutter 82 is closed, causing the sharp jaw 88 of the cutter to close completely and sever the wire 120 flush with the bone surface.

Figure 38:
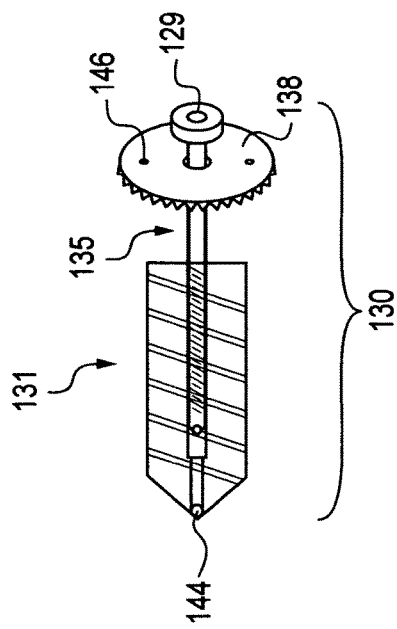
FIG. 38 is a perspective view of a modular interference screw-ligament washer in accordance with the present invention.
Figure 40:
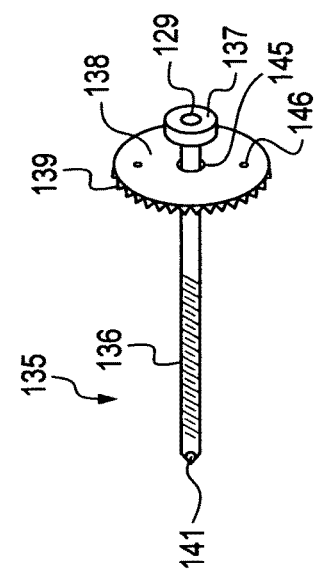
FIG. 40 is a perspective view of a separate cannulated screw component and mobile ligament washer component of the interference screw-ligament washer shown in FIG. 38.
Figure 39:
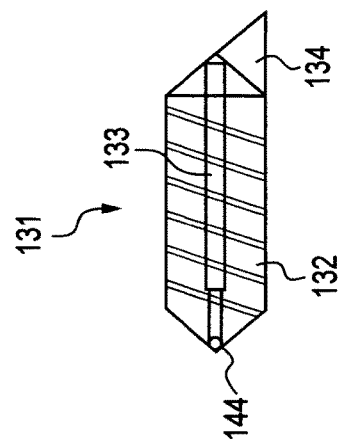
FIG. 39 is a perspective view of a cannulated interference screw component of the modular interference screw-ligament washer shown in FIG. 38.
Figure 41:
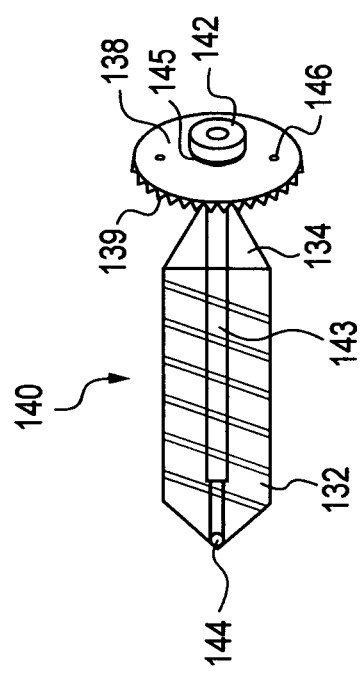
FIG. 41 is a perspective view of a non-modular interference screw-ligament washer in accordance with the present invention.

The free ends of soft-tissue grafts 75 and 75A are fixed in a bone tunnel using a novel interference screw-ligament washer which may be a modular form 130 or a non-modular form 140. The modular form is shown in FIGS. 38, 39 and 40, while the non-modular form is shown in FIG. 41. The interference screw-ligament washer is made of durable materials which are non-absorbable, bio-absorbable, or capable of bio-integration.

Figure 46:
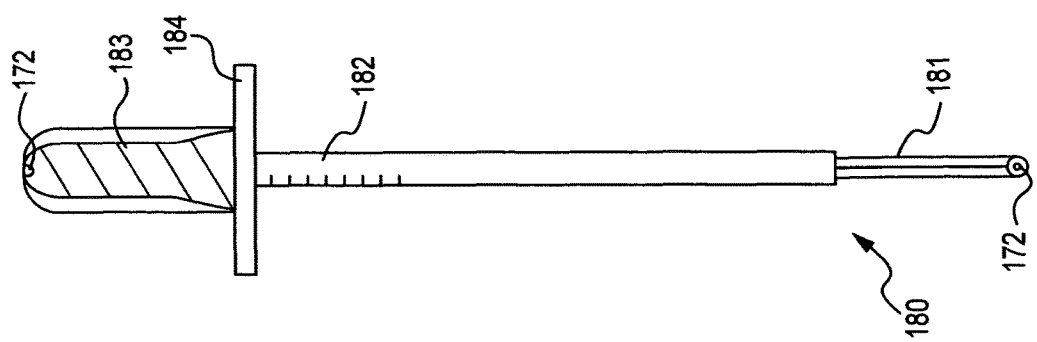
FIG. 46 is a perspective view of a cannulated screw driver component of the insertion-tensioner tool shown in FIG. 42.

The modular interference screw-ligament washer 130 includes a cannulated interference screw component 131, a separate cannulated screw component 135, and a mobile ligament washer component 138, shown in FIGS. 38, 39 and 40. The sizes of the cannulated interference screw component 131 may vary, with length ranging up to 100 mm, but preferably 20 mm to 30 mm, and having an outer diameter up to 25 mm, preferably 4 mm to 15 mm. The component 131 also incorporates a central longitudinal cannulation 144 to allow it to be inserted over a guide wire 190. The outer surface 132 of the cannulated interference screw component 131 is threaded for purchase in both the walls of the bone tunnel and in the adjacent soft-tissue graft. The rear end 134 of the cannulated interference screw component 131 may be flat, tapered or oblique. In addition to its cannulation 144 for guide wire 190, the cannulated interference screw component 131 additionally includes a longitudinal female socket 133 having a hexagonal, star, diamond or other complementary cross sectional geometry to accept a male connector on the tip 181 of a cannulated screw driver 180 (FIG. 46).

The separate cannulated screw component 135 includes a partially threaded end 136 and a head 137, as shown in FIGS. 38 and 40. The screw component 135 has a central longitudinal cannulation 141 to allow it to be inserted over guide wire 190. The partially threaded end 136 has a diameter and length which corresponds to that of the female socket 133 of the interference screw component 131 in order to allow the separate cannulated screw component 135 to seat all the way to the depth of its head 137 and gain purchase. The head 137 is low-profile with the female socket 129, and the size and geometry of head 137 is sufficiently different from cannulation 145 in mobile ligament washer component 138 to allow head 137 to capture washer component 138.

The mobile ligament washer component 138 can be of variable geometry but is relatively flat in one dimension in order to allow it to be low profile when seated, as shown in FIGS. 38, 40 and 41. This washer's width, or diameter, ranges up to 25 mm, and is preferably between 5 mm and 15 mm. Other cannulations 146 may be formed in mobile ligament washer 138 which provide additional means for fixing an ACL graft with sutures passed through these cannulations and secured or tied.

The central cannulation 145 in the mobile ligament washer component 138 possesses sufficient size and geometry to allow it to tilt up to 90 degrees relative to the long axis of the cannulated screw component 136, preferably between zero and 60 degrees. The undersurface 139 of the ligament washer component 138 is an irregular surface, formed with spikes or other soft-tissue adhesive features, and it may possess other protruding surface geometry to assist in centering the washer 138 over the entrance to either of the femoral tunnels 55 or the tibial tunnels 6. The central cannulation 75 in the washer component 138 may be surrounded by a recessed portion in the washer 138 which accepts the head 137 of the separate cannulated screw component 135.

Figure 50:
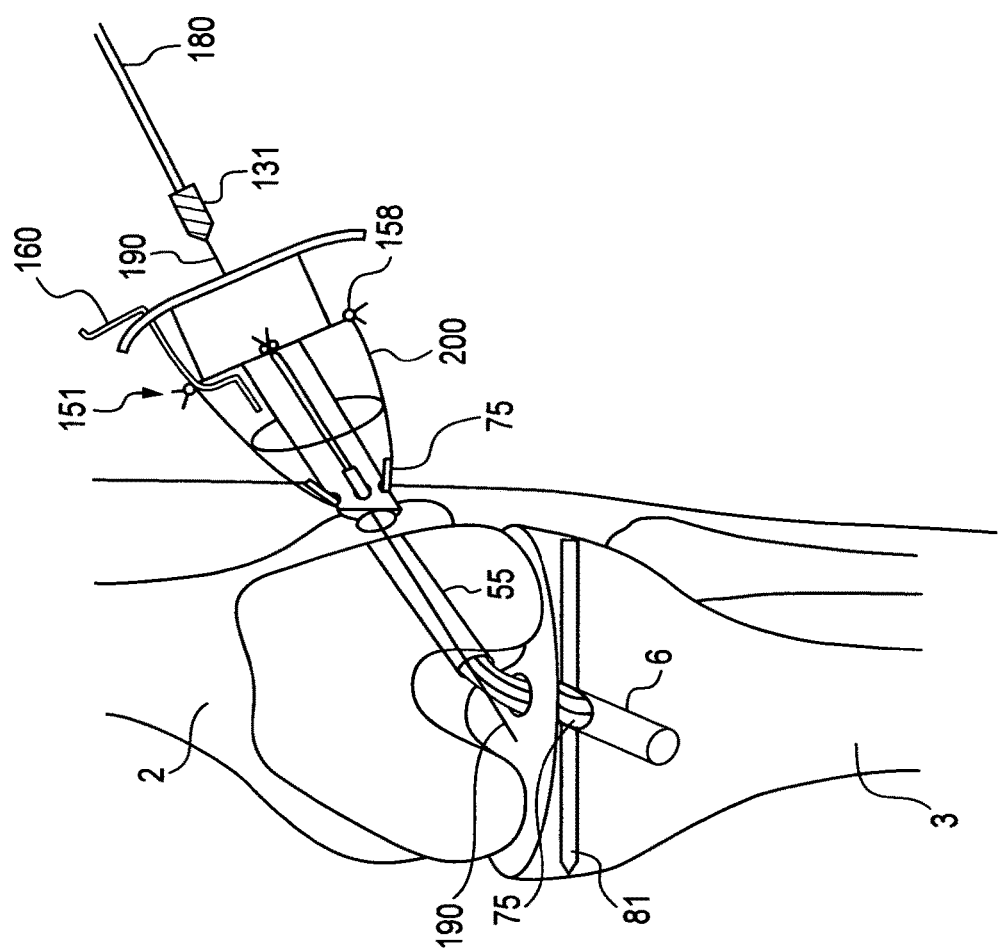
FIG. 50 is a schematic view of a manner of inserting the interference screw component of the modular interference screw-ligament washer shown in FIG. 38 utilizing the insertion-tensioner shown in FIG. 42 and the cannulated screwdriver component shown in FIG. 46 in accordance with the present invention.
Figure 51:
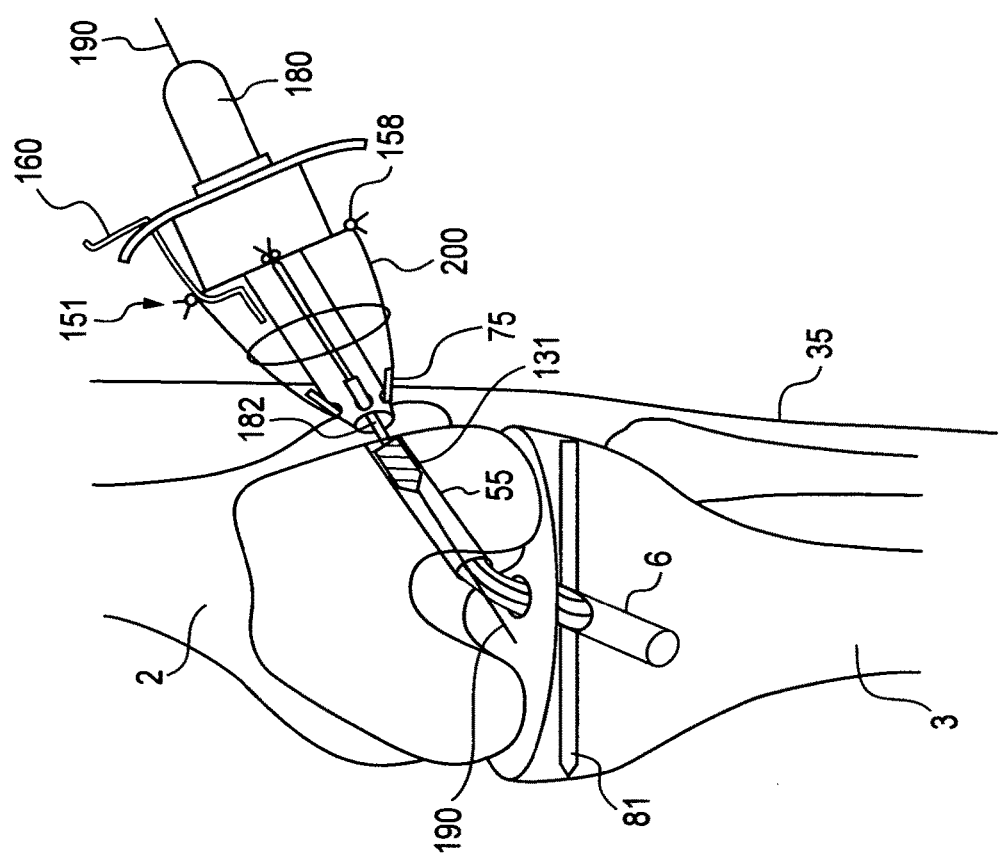
FIG. 51 is a schematic view of a manner of inserting the interference screw component of the modular interference screw-ligament washer shown in FIG. 38 utilizing the insertion-tensioner shown in FIG. 42 and the cannulated screwdriver component shown in FIG. 46 in accordance with the present invention.
Figure 52:
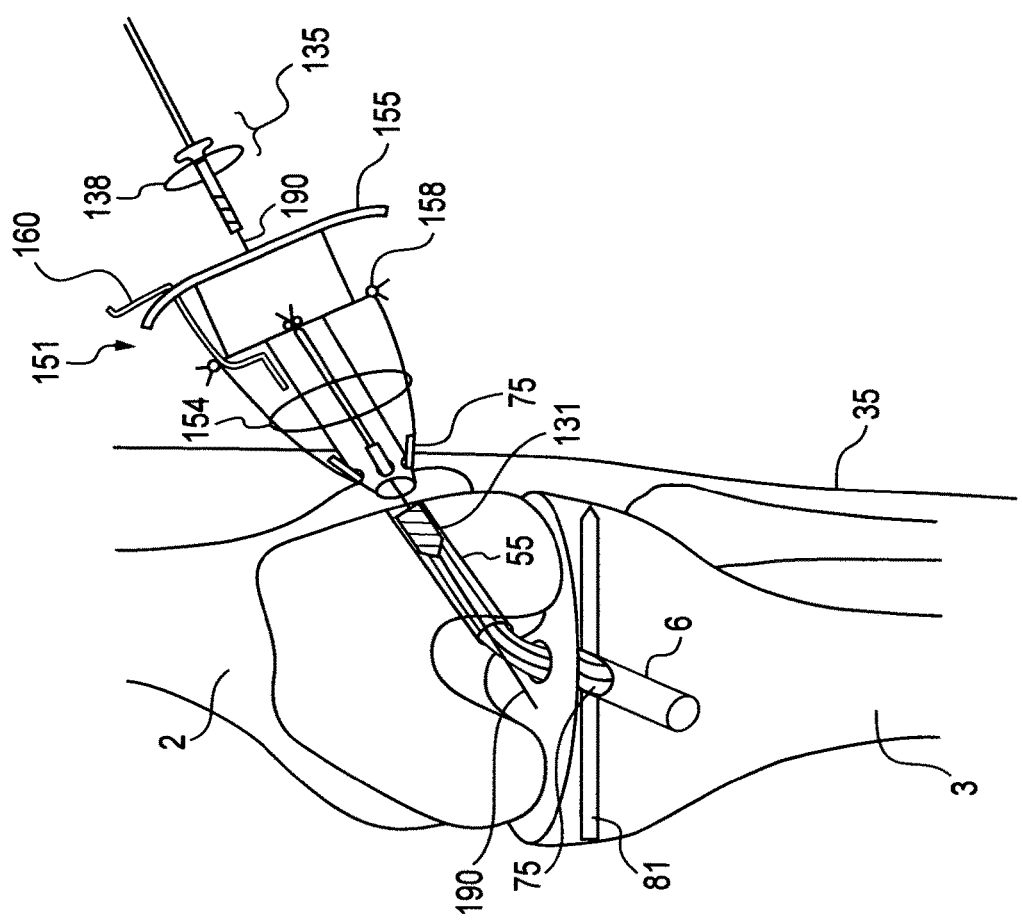
FIG. 52 is a schematic view of a manner of inserting the separate cannulated screw and mobile ligament washer components of the modular interference screw-ligament washer shown in FIG. 40 utilizing the insertion-tensioner tool shown in FIG. 42 and the cannulated screw driver shown in FIG. 46 in accordance with the present invention.

After a soft-tissue graft 75 is positioned in a bone tunnel, preferably with its free ends extending beyond the outside end of the tunnel, the modular form 130 of the interference screw-ligament washer is inserted. First, the cannulated interference screw component 131 is advanced over a guide wire 190 to a position adjacent to the soft-tissue graft 75 in the bone tunnel using a proper screw driver 180, as in FIGS. 50 and 51. Once the rear end 134 of the interference screw component 131 is advanced to the level of the opening of the bone tunnel or just below it, another cannulated screw driver is used to advance the separate cannulated screw component 135 with the mobile ligament washer component 138 into female socket 133 of the interference screw component 131 until the irregular undersurface 139 of the ligament washer component 138 firmly compresses the protruding ends of the soft-tissue graft 75 up against the cortical surface of the bone surrounding the tunnel opening (see FIGS. 52, 53, 59 and 69). Sutures 200 are placed in the protruding ends of the soft-tissue grafts 75 to provide manual tension while the interference screw-ligament washer device 130 is inserted.

Figure 54:
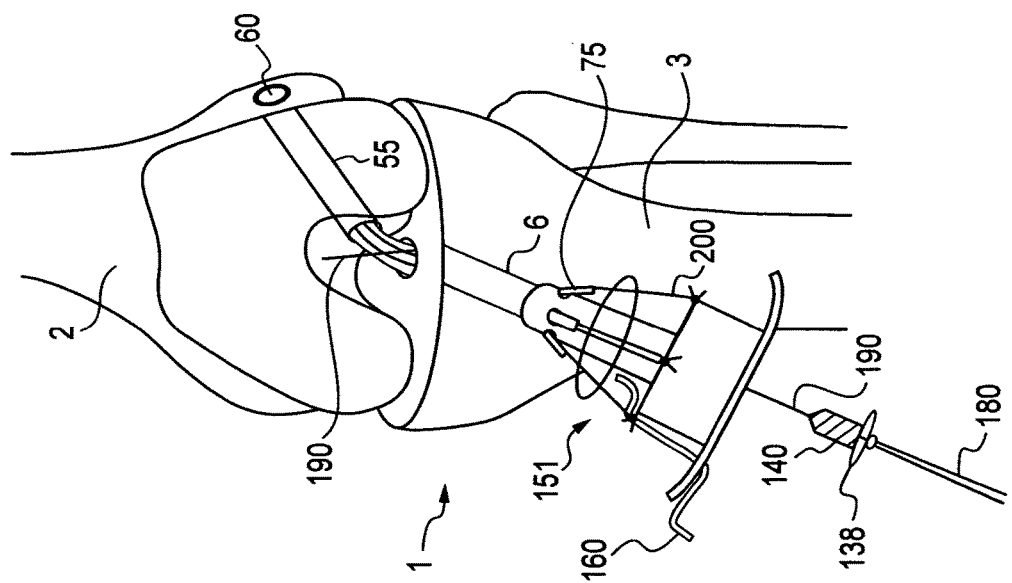
FIG. 54 is a schematic view of a manner of inserting the non-modular interference screw-ligament washer shown in FIG. 41 utilizing the insertion-tensioner tool shown in FIG. 42 and the cannulated screw driver shown in FIG. 46 in accordance with the present invention.
Figure 55:
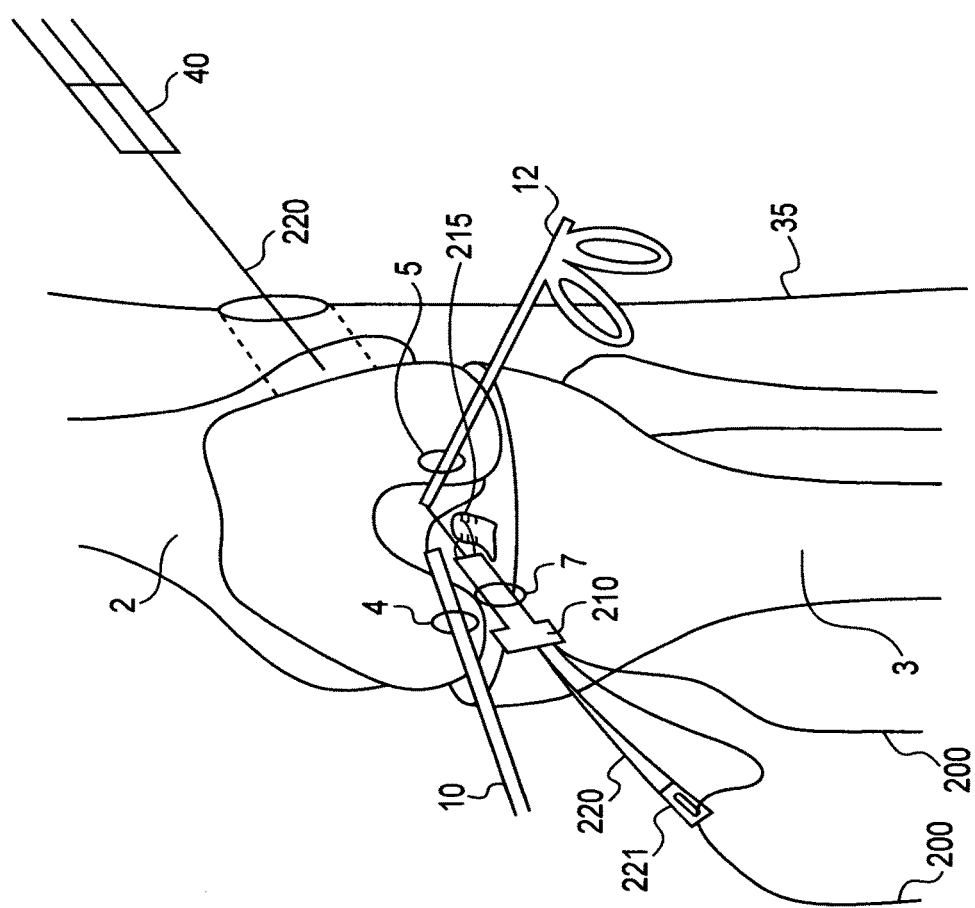
FIG. 55 is a schematic view of a manner of repairing an ACL tear utilizing the femoral guide tool shown in FIG. 1, the surgical guide pin shown in FIG. 22, and the cannulated scalpel shown in FIG. 7 in accordance with the present invention.
Figure 57:
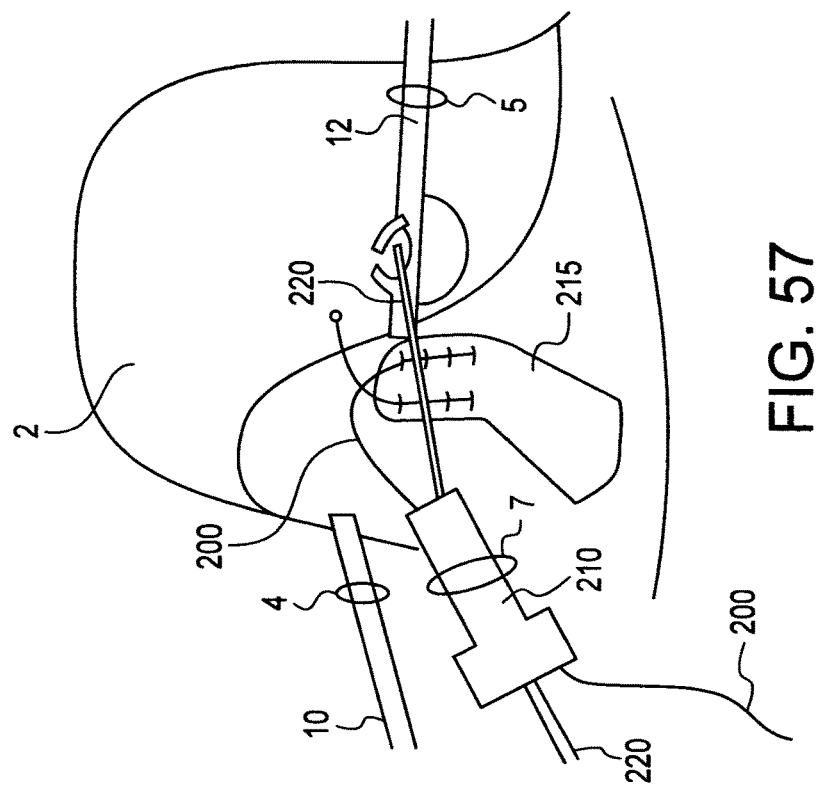
FIG. 57 is an enlarged schematic view of a portion of FIG. 55 illustrating a manner of positioning the surgical guide pin shown in FIG. 22 to pass an additional suture placed in the torn end of the ACL in accordance with the present invention.
Figure 56:
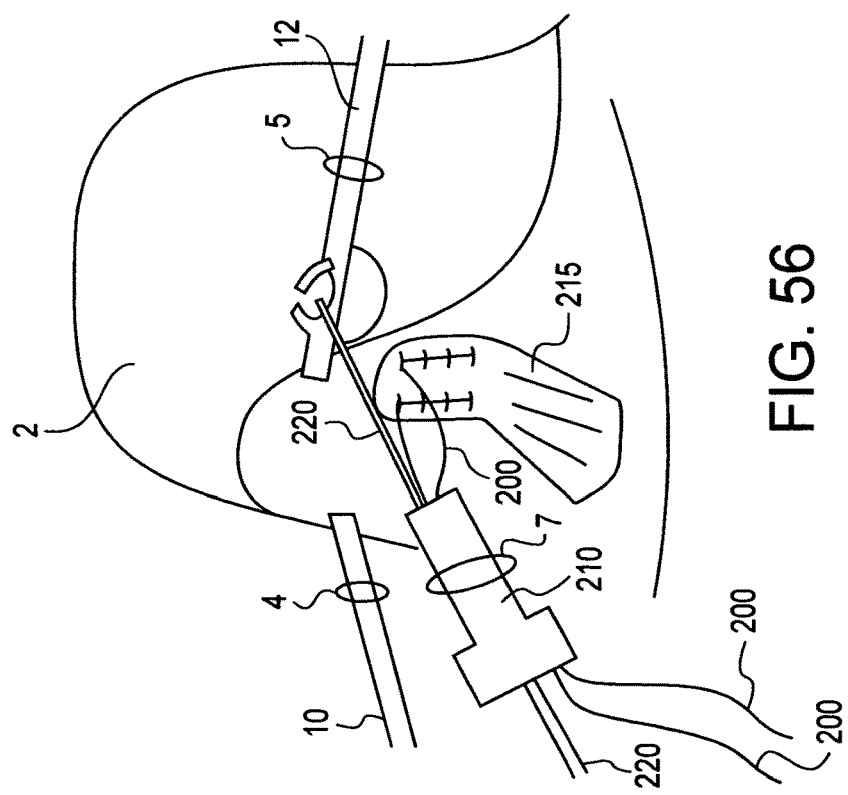
FIG. 56 is an enlarged schematic view of a portion of FIG. 55 illustrating a manner of positioning the surgical guide pin shown in FIG. 22 to pass a suture placed in the torn end of the ACL in accordance with the present invention.
Figure 59:
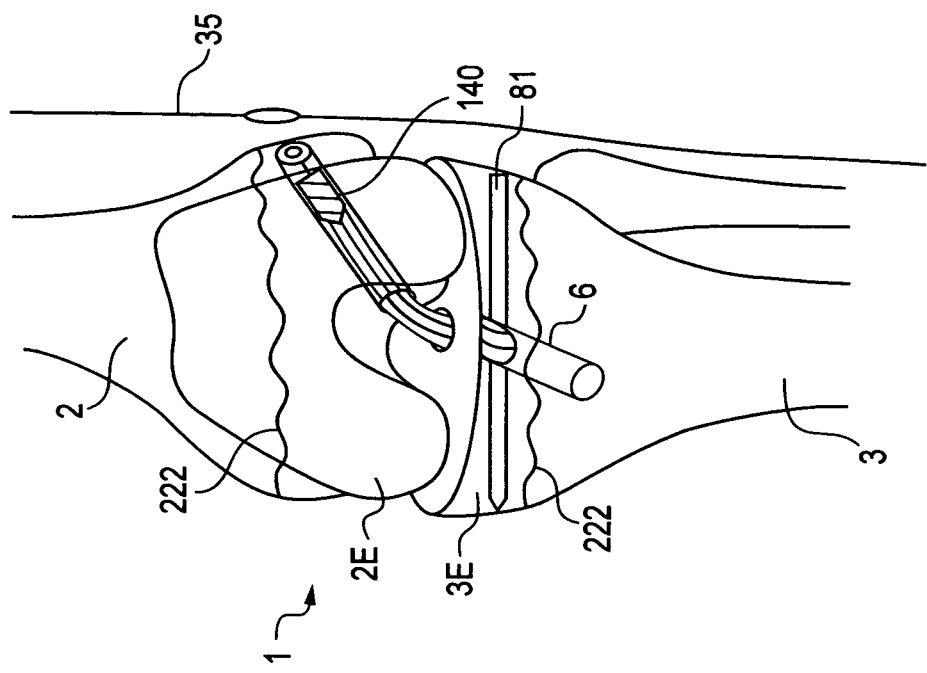
FIG. 59 is a schematic view of a manner of securing an ACL graft in a femoral and tibial epiphysis of a skeletally immature knee without crossing either the femoral or tibial physis utilizing the femoral interference screw-ligament washer shown in FIGS. 38 and 41 and the suspension pin shown in FIGS. 20A and 20B in accordance with the present invention.
Figure 61:
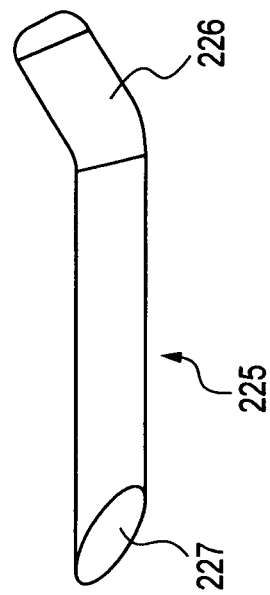
FIG. 61 is a top plan view of the protective sleeve shown in FIG. 60.
Figure 60:
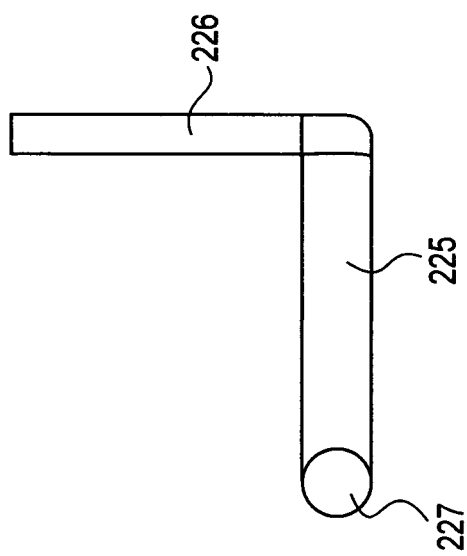
FIG. 60 is a perspective view of a protective sleeve in accordance with the present invention.
Figure 63:
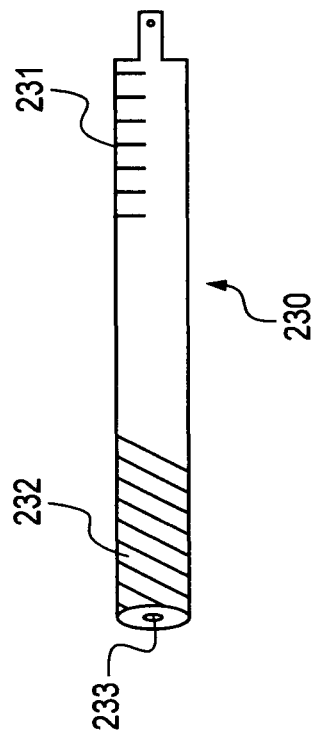
FIG. 63 is a perspective view of a cannulated drill bit in accordance with the present invention.
Figure 62:
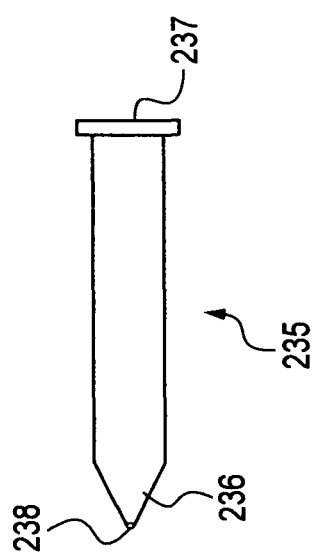
FIG. 62 is a perspective view of a bullet guide in accordance with the present invention.
Figure 69:
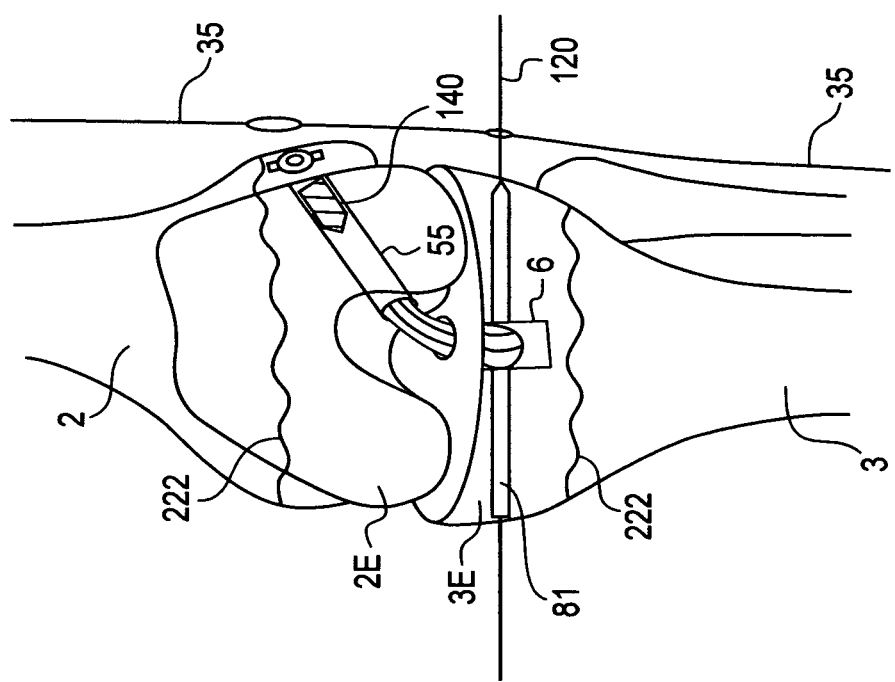
FIG. 69 is a schematic view of a manner of securing an ACL graft in the femoral and tibial epiphysis of a skeletally immature knee without crossing either the femoral or tibial physis utilizing a femoral interference screw-ligament washer of FIGS. 38 and 41 and a tibial suspension pin of FIGS. 20A and 20B in accordance with the present invention.

The non-modular form of the interference screw-ligament washer is a single unit made of a single or composite material (see FIG. 41). The features of the non-modular form are identical to the modular form 130, including a threaded outer surface on the interference screw portion 132, a flat, tapered or oblique rear-end 134, a mobile ligament washer component 138, and a head 142 with sufficient size and geometry to capture the ligament washer component 138. The non-modular form of the interference screw-ligament washer 140 is a single preassembled or manufactured unit which can be inserted into a bone tunnel in a single step until the irregular undersurface 139 of the ligament washer component 138 firmly compresses the protruding ends of the soft-tissue graft 75 up against the cortical surface of the bone surrounding the tunnel opening, as illustrated in FIGS. 54, 59 and 69. Non-modular form 140 also maintains a longitudinal female socket 143 of specified cross-sectional geometry (hexagonal, star, diamond, or the like) to accept a male connection on the tip 181 of cannulated screw driver 180.

The female socket 143 extends just into head 142, although it may extend all of the way through the head into the interference screw portion 132 of the non-modular form 140 of interference screw-ligament washer. Also, there is a longitudinal cannulation 144 in the non-modular form 140 which allows the non-modular form to be inserted over guide wire 190.

If the free ends of soft-tissue graft 75 are not long enough to exit the bone tunnel, sutures 200 placed in the ends of graft 75 may be passed through small cannulations 146 in the ligament washer component 138 before insertion and then tied after either the modular form 130 or the non-modular form 140 of the interference screw-ligament washer is inserted into the tunnel adjacent to graft 75.

The modular and non-modular forms 130 and 140 of the interference screw-ligament washer may also be used on a bony free end of a graft 75. The sutures 200 attached to the bone plug may be passed through small cannulations 146 in the ligament washer component 138 before insertion and tied after either the modular form 130 or the non-modular form 140 of the interference screw-ligament washer is inserted in the bone tunnel adjacent to the bone end of the graft.

The interference screw component 131 of modular interference screw-ligament washer 130 may also be used alone to fix either a bony or a soft-tissue end of graft 75.

Either of the modular or non-modular forms of the interference screw-ligament washer, 130 or 140, may be inserted using an insertion-tensioner tool 151 and the components 165, 168, 175, 180 shown in FIGS. 48, 49, 50, 51, 52, 53 and 54. The insertion-tensioner 151 assists with graft tensioning and with the insertion of fixation devices to secure free ends of graft 75 in a bone tunnel (see FIGS. 42 and 43). These devices include a trocar component 168, a graft loader component 165, a cutter component 175 and a cannulated screw driver 180 (see FIGS. 44, 45, 46 and 47).

The insertion-tensioner 151 includes two hollow tubes 157 and 159 which have coordinating inner and outer diameters to allow tube 159 to telescope into tube 157, as shown in FIGS. 42 and 43. The inner diameter of tube 159 may be up to 50 mm, but preferably 15 mm to 25 mm. There is a unidirectional stopping mechanism which prevents tube 159 from exiting tube 157 whenever tube 159 is moved through tube 157 toward tube 159's end 152. There is a separate locking mechanism 156 which may be engaged or released by a lever 160 attached to tube 157, including teeth or other surface-engaging geometry 161 on the lever which interface with opposing surface 162 on tube 159. The tubes 157 and 159 move freely when lever 160 is not engaged, but when it is engaged, the tubes may be moved freely in one direction and prevented from moving in the opposite direction. Preferably, that restriction prevents tube 157 from moving along tube 159 towards the end 152 of tube 159. A spring (not shown) may be used to keep lever 160 in place when it is not manipulated by a surgeon.

Handles 154 and 155 may be used by a surgeon to grasp and manipulate tubes 157 and 159 relative to each other. Tube 159 may include indicia to help calibrate movement between the tubes. Tube end 152 may be beveled or flat. There are multiple cannulations 153 in tube 159, preferably four, through which the ends of soft-tissue graft 75 may pass. At the end of tube 157, an arrangement of cleats 158, or similar graft engaging elements, allow the temporary fixation of sutures 200 attached to grafts 75. Handle 155 may be attached firmly to tube 157, or it may be spring-biased by attaching it in series to tube 157 and the cleat arrangement 158 by means of a calibrated spring mechanism 163 in order to measure the tension of the tube engagement.

The trocar 168 (see FIG. 44) preferably is a long rod with an outer diameter sufficiently corresponding to the inner diameter of tube 159 to allow trocar 168 to just fit within the tube. However, the trocar may be formed as a tube, or have a central longitudinal cannulation 171. The length of trocar 168, excluding its stop end 170 and its leading tapered end 169 is equal to the combined length of tubes 157 and 159 when they are telescoped at their shortest starting position. The stop end 170 of the trocar 168 has a diameter greater than the diameter of tube 157, thus limiting the depth to which trocar 168 may be inserted into the insertion-tensioner 151. When trocar 168 is inserted to its full depth, its tapered end 169 protrudes from end 152 of tube 159 to facilitate penetration of the insertion-tensioner down through the skin and soft-tissue of knee 1 to femur 2 or tibia 3. Slots 173 are formed in the tapered end 169 of trocar 168 which extend beyond the inclination of the taper, allowing free ends of the soft-tissue graft 75 to run freely along the slots 173 and into the end 152 of tube 159 and on out through cannulations 153 in tube 159.

The cutter 175 (see FIG. 47) is a hollow tube with a stop end 177 and a sharp cutting end 176. Cutter 175 has an outer diameter corresponding to the inner diameter of tube 159. The length of cutter 175, excluding its stop end 177, is such that when the cutter 175 is inserted into the insertion-tensioner 151 to the full depth with the telescoping tubes 157 and 159 extended to their longest finishing tensioned position, the sharp cutting end 176 extends just beyond cannulations 153 in the end 152 of tube 159. Sharp cutting end 176 is inwardly beveled. The outer edge of the cutting end 176 is straight in order to maintain a constant outer diameter. The inner edge is beveled inwardly from the outer edge to the inner surface of the tube to create a sharp-ended cutting tube.

Figure 45:
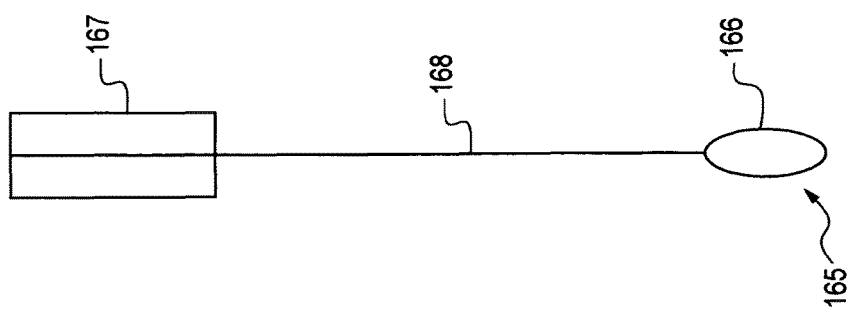
FIG. 45 is a perspective view of a graft loader component of the insertion-tensioner shown in FIG. 42.
Figure 44:
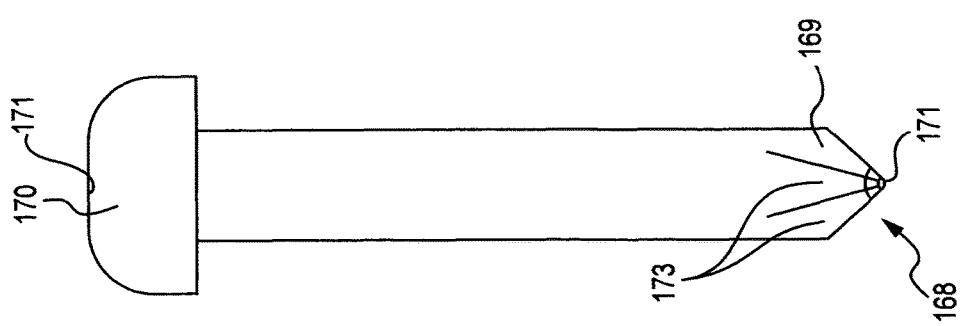
FIG. 44 is a perspective view of a trocar component of the insertion-tensioner tool shown in FIG. 42.
Figure 47:
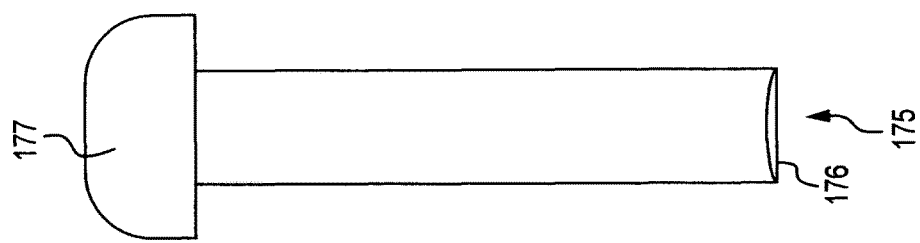
FIG. 47 is a perspective view of a cutter component of the insertion-tensioner shown in FIG. 42.

The graft loader 165, a long stiff but flexible wire 168 with a loop end 166 and an optional handle 167, is shown in FIG. 45. The loop end is flexible and has a loop with sufficient diameter to carry a suture or the free ends of graft 75.

The cannulated screw driver 180 includes a tip 181, a calibrated shaft 182, and a handle 183 which has an optional stop 184 (see FIG. 46). The tip 181 is formed with a specific geometrical cross section, such as a hexagon, star, diamond or the like, to fit with like connections in the interference screw-ligament washers 130 or 140 or other fixation devices. Calibrated shaft 182, excluding its handle 183, the stop 184 and the tip 181, is at least as long as the combined length of telescopically connected tubes 157 and 159 extended to their longest finishing tensioned position.

The above-described components are used with the insertion-tensioner 151 in the following manner.

Figure 48:
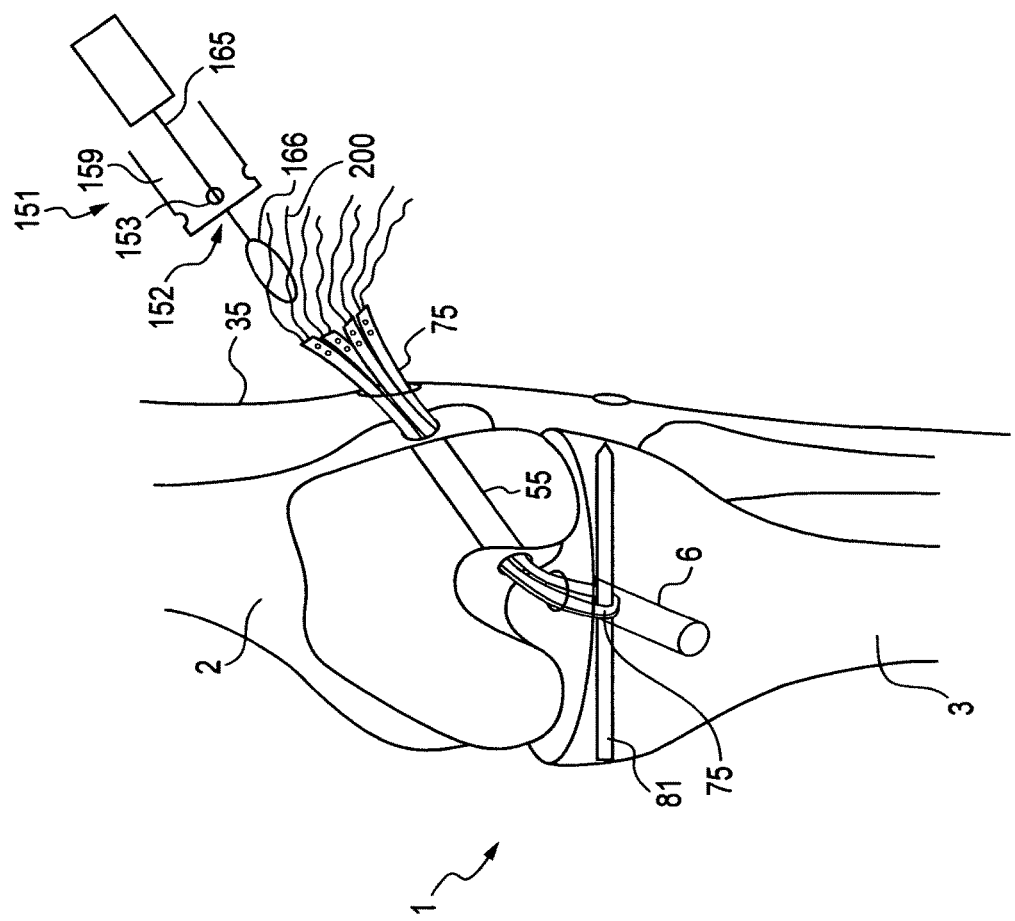
FIG. 48 is a schematic view of a manner of loading the free end of a soft-tissue graft into the insertion-tensioner shown in FIG. 42 utilizing the graft loader component shown in FIG. 45 in accordance with the present invention.

With the free ends of a soft-tissue graft 75 fixed at their opposite ends and protruding from a bony tunnel, each free end is individually placed through the loop end 166 of the graft loader 165 where it was previously positioned, i.e., extending through one of the cannulations 153 and exiting out of end 152 of tube 159 of the insertion-tensioner 151 (see FIG. 48). It is preferable that the graft ends have been prepared with sutures 200 prior to loading to help facilitate graft passing and tensioning later.

Figure 49:
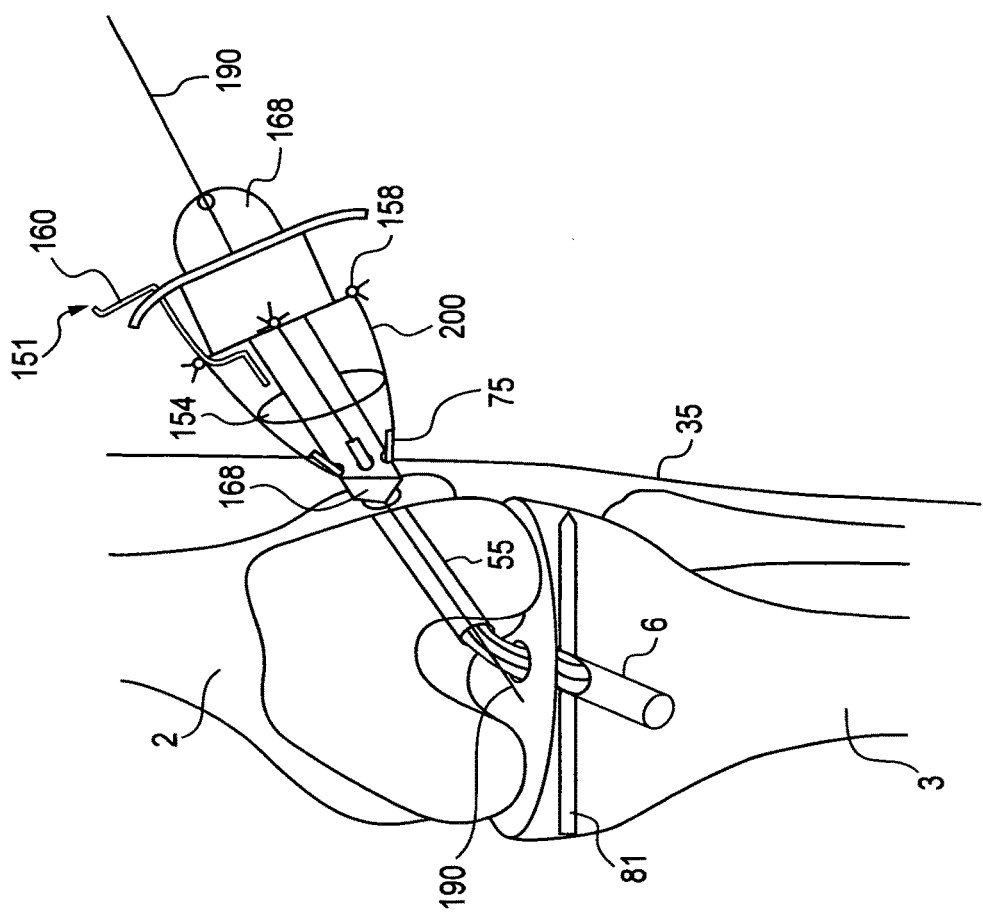
FIG. 49 is a schematic view of a manner of positioning the insertion-tensioner shown in FIG. 42 loaded with a soft-tissue graft over an opening of a bone tunnel utilizing the trocar component shown in FIG. 44 and a guide wire in accordance with the present invention.

With all of the free ends of the soft-tissue graft 75 or their sutures 200 passed into the end 152 and out of their own cannulation 153 of tube 159, trocar 168 is inserted into the insertion-tensioner 151 while its tubes 157 and 159 are telescoped to their shortest length, as shown in FIG. 49. While holding the free ends of the graft 75 or their attached sutures 200 under tension in one hand, the surgeon inserts the insertion-tensioner 151 with trocar 168 through the skin and soft-tissues down to the bone at the opening of a bone tunnel, preferably that of femur 2 or tibia 3. The insertion-tensioner 151 with the cannulated trocar 168 may also be inserted over a guide wire 190 previously placed in bone tunnels 6 or 55. The longitudinal cannulation 171 in trocar 168 accepts the guide wire 190 to properly direct the insertion-tensioner 151 through the skin and soft-tissue down to the opening of a bone tunnel. Once down to bone, trocar 168 is removed. The free graft ends of graft 75 or their attached sutures 200 are tensioned and secured to the cleats 158 on the insertion-tensioner 151. With one hand on handle 154 to stabilize tube 159 and hold the tube end 152 on the bone tunnel opening, the surgeon distracts on handle 155 of tube 157 with the other hand to the desired tension and activates lever 160 to engage the locking mechanism 156, thus holding the graft ends of graft 75 at a desired tension.

Maintaining the position of the insertion-tensioner 151 with a hand on handle 154 and tube 159, the surgeon inserts either the modular form 130 or the non-modular form 140 interference screw-ligament washer, as described above, over the guide wire 190, fixing the graft ends of graft 75 in a bone tunnel, preferably that of femur 2 or of tibia 3 (see FIGS. 50, 51, 52, 53, 54, 59 and 69).

The surgeon may also elect to insert another ACL fixation device by another method utilizing the insertion-tensioner 151.

Figure 53:
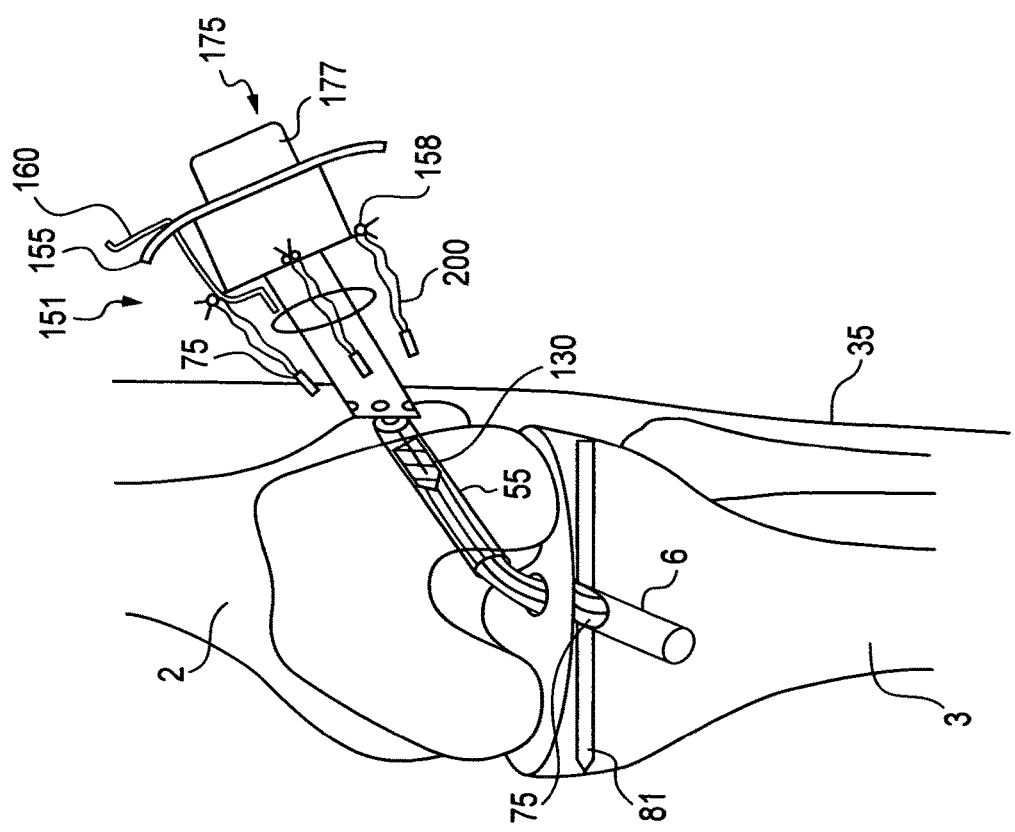
FIG. 53 is a schematic view of a manner of cutting free ends of soft-tissue graft utilizing the cutter component shown in FIG. 47 of the insertion-tensioner tool shown in FIG. 42 after the graft has been secured by the modular or non-modular interference screw-ligament washer shown in FIGS. 38 and 41 in accordance with the present invention.

After the ACL fixation device is placed and the free graft ends of graft 75 are secured, cutter 175 is inserted into the exposed end of the insertion-tensioner 151 and advanced until the free ends of graft 75 or their attached sutures are cut, as in FIG. 53.

Different combinations of fixation devices may be utilized when multiple bone tunnels are formed in either or both of femur 2 and tibia 3 as long as a cross pin device such as a suspension pin 80 or 81 or a surgical ring fixation tool 60 is used on the looped ends of the graft 75 and either the modular form 130 or non-modular form 140 of the interference screw-ligament washer are used on the free soft-tissue or bony ends of graft 75.

Figure 58:
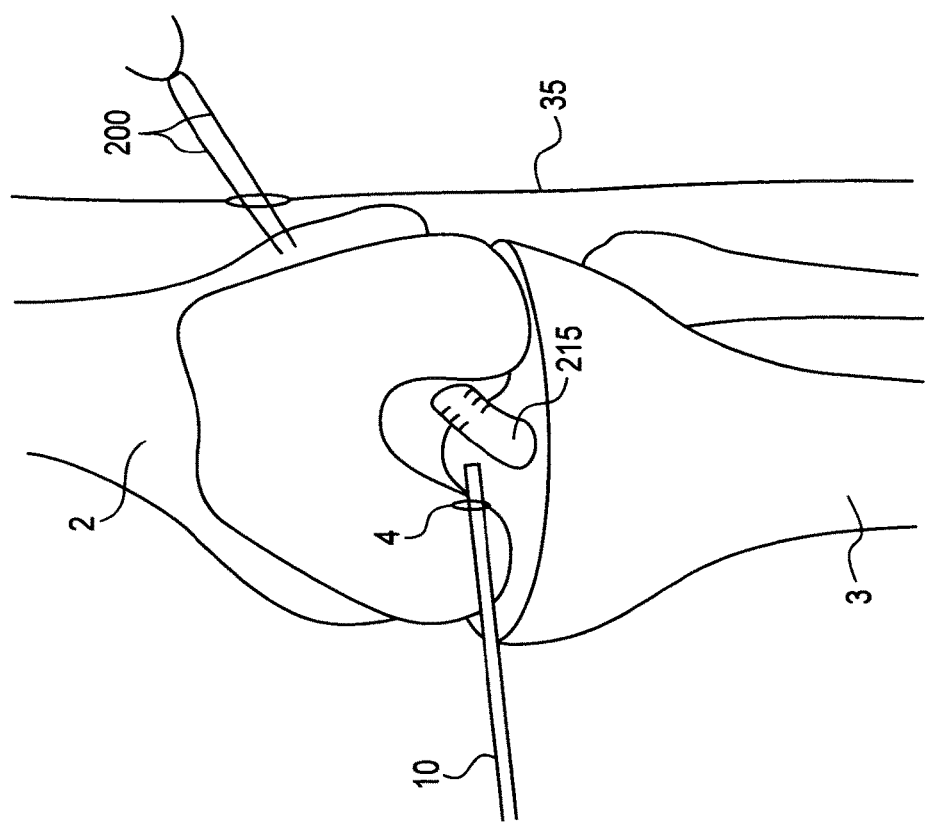
FIG. 58 is a schematic view of a manner of securing the sutures used to repair the ACL tear after using the femoral guide tool shown in FIG. 1, the surgical guide pin shown in FIG. 22 and the cannulated scalpel shown in FIG. 7 in accordance with the present invention.

Primary repair of an ACL stump 215 torn off the femur 2 may also be performed using femoral guide 12, as seen in FIGS. 55, 56, 57 and 58. After sutures 200 are passed through stump 215, arthroscope 10 is positioned in a conventional medial infrapatellar arthroscopic portal 4, and a conventional arthroscopic cannula 210 is positioned in an accessory medial infrapatellar arthroscopic portal 7. The sutures 200 attached to ACL stump 215 are retrieved out of knee 1 through cannula 210. Then a surgical guide pin 220 is introduced into knee 1 through the same arthroscopic cannula 210, and femoral guide 12 is placed through the lateral infrapatellar arthroscopic portal 5 to grasp and direct the leading end of surgical guide pin 220 as it is drilled through femur, skin and soft-tissue with a power drill such as drill 11. With both ends of the surgical guide pin 220 exposed from knee 1, one limb of sutures 200 attached to ACL stump 215 is loaded through slot 221 at the back end of a surgical guide pin 220. A cannulated scalpel, such as scalpel 40, is then passed over the exposed leading end of guide pin 220 to create a passage through the skin and soft-tissue to the lateral bony cortex of a femur 2. The guide pin 220 is then advanced out of knee 1 to shuttle a suture limb through the femur and out through the passageway created by the cannulated scalpel 40. The steps just described are repeated until all of the limbs of suture 200 attached to the ACL stump are passed. The passed sutures 200 are tensioned and secured over either a conventional cannulated button or the natural cortical bony bridges remaining between each of the sutures 200 on the lateral aspect of the femur 2, as shown in FIG. 58.

For skeletally immature patients with open femoral and tibial growth plates such as plate 222, nominally referred to as physes, the epiphyseal tunnel and graft fixation procedure holds substantial benefit by avoiding injury to the growth plate 222. Using intraoperative radiographic assistance, all-epiphyseal femoral tunnels, like tunnel 55, can be created using a conventional outside-in femoral guide or the novel femoral guide 12, as described above, and transphyseal tibial tunnels, like tibial tunnel 6, can be created with conventional tibial guides (see FIG. 59). For epiphyseal femoral 2 graft fixation, modular form 130 and non-modular form 140 interference screw-ligament washers may be inserted into the femoral epiphysis 2E using the methods and instruments described above (see FIG. 59). For tibial epiphyseal graft fixation in a transphyseal tunnel, the suspension pin 80 or its alternative 81 may be inserted into the tibial epiphysis 3E using the methods and instruments described above (see FIG. 59).

However, an alternative and novel method of antegrade epiphyseal tunnel creation and graft fixation will now be described. To perform this procedure, the surgeon needs a specially designed protective sleeve 225, a cannulated bullet guide 235, and a specially designed cannulated drill bit 230, as shown in FIGS. 60, 61, 62 and 63.

The protective sleeve 225 is a hollow tube with a beveled tip 227 and a handle 226. Preferably, the handle points 90 degrees counterclockwise from the longest side of the beveled tip 227 as viewed looking down the longitudinal axis of the sleeve from the handle side. The inner diameter of the sleeve ranges up to 20 mm, preferably between 4 mm and 12 mm.

Cannulated bullet guide 235 and cannulated drill bit 230 have outer diameters that correspond to the inner diameter of protective sleeve 225 which permits bullet guide 235 and cannulated drill bit 230 to just fit but move freely within sleeve 225. Bullet guide 235 has a central longitudinal cannulation 238, a tapered end 236 and an end with a stop 237 which abuts the handle end of the protective sleeve 225 when inserted. The length of the bullet guide, excluding the tapered end 236 and stop 237 equals the length of the protective sleeve 225. Cannulated drill bit 230 is partially threaded at its cutting end 232 and smooth, with depth marks 231 which reference off the handle end of sleeve 225. The cannulated drill bit possesses a longitudinal cannulation 233 which allows the drill bit 230 to be run over a guide pin.

Figure 64:
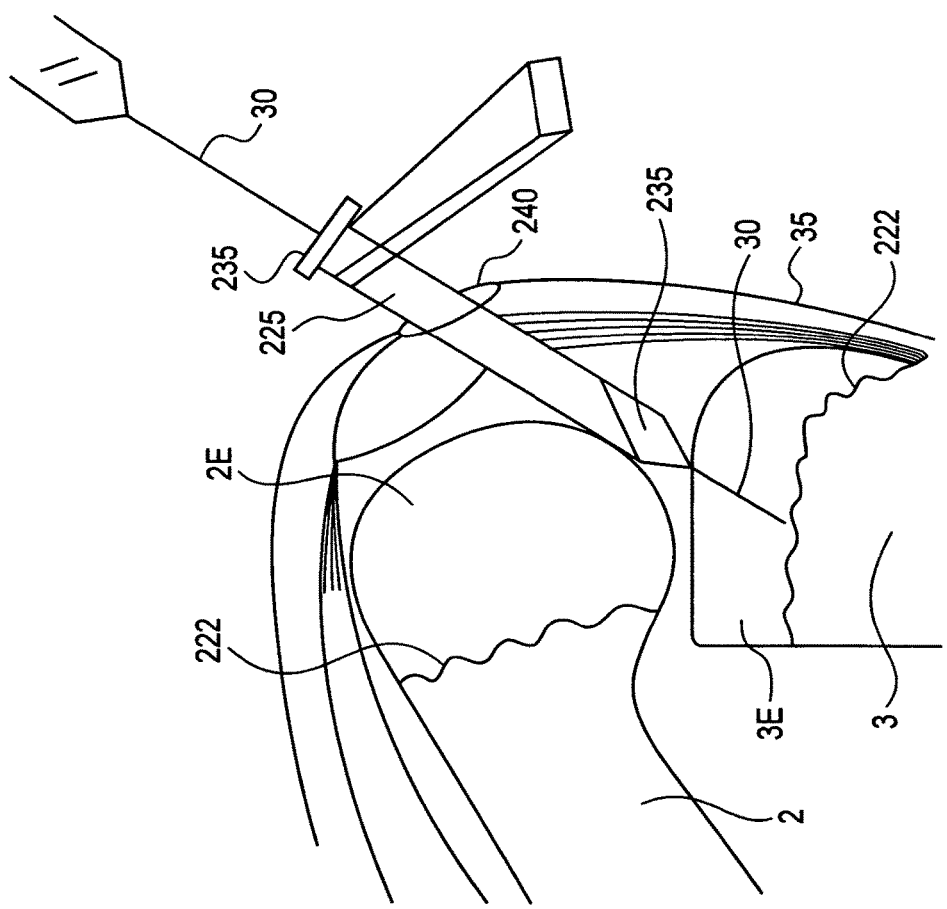
FIG. 64 is a schematic view of a manner of placing a guide pin into the ACL footprint of the tibial epiphysis of a skeletally immature knee without crossing the tibial physis utilizing the protective sleeve of FIG. 60, the bullet guide of FIG. 62 and a guide pin in accordance with the present invention.
Figure 65:
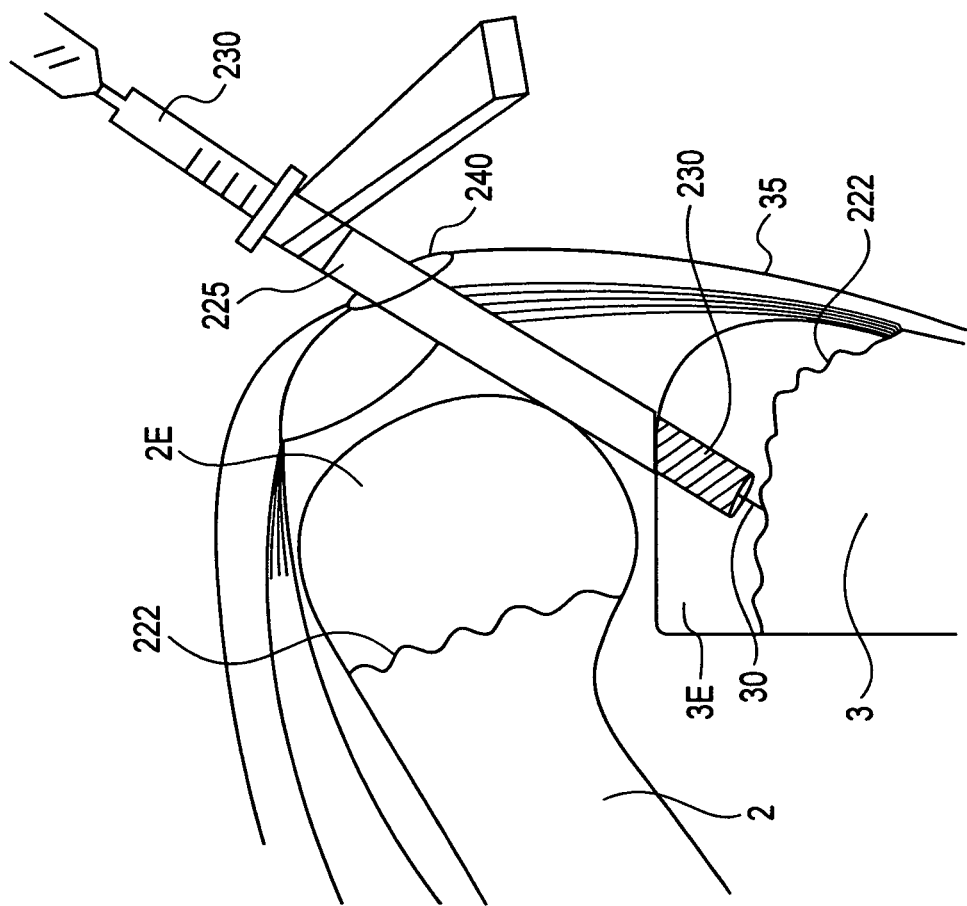
FIG. 65 is a schematic view of a manner of drilling a bone tunnel into the ACL footprint of the tibial epiphysis of a skeletally immature knee without crossing the tibial physis utilizing the protective sleeve of FIG. 60, a guide pin, and the cannulated drill bit of FIG. 63 in accordance with the present invention.
Figure 66:
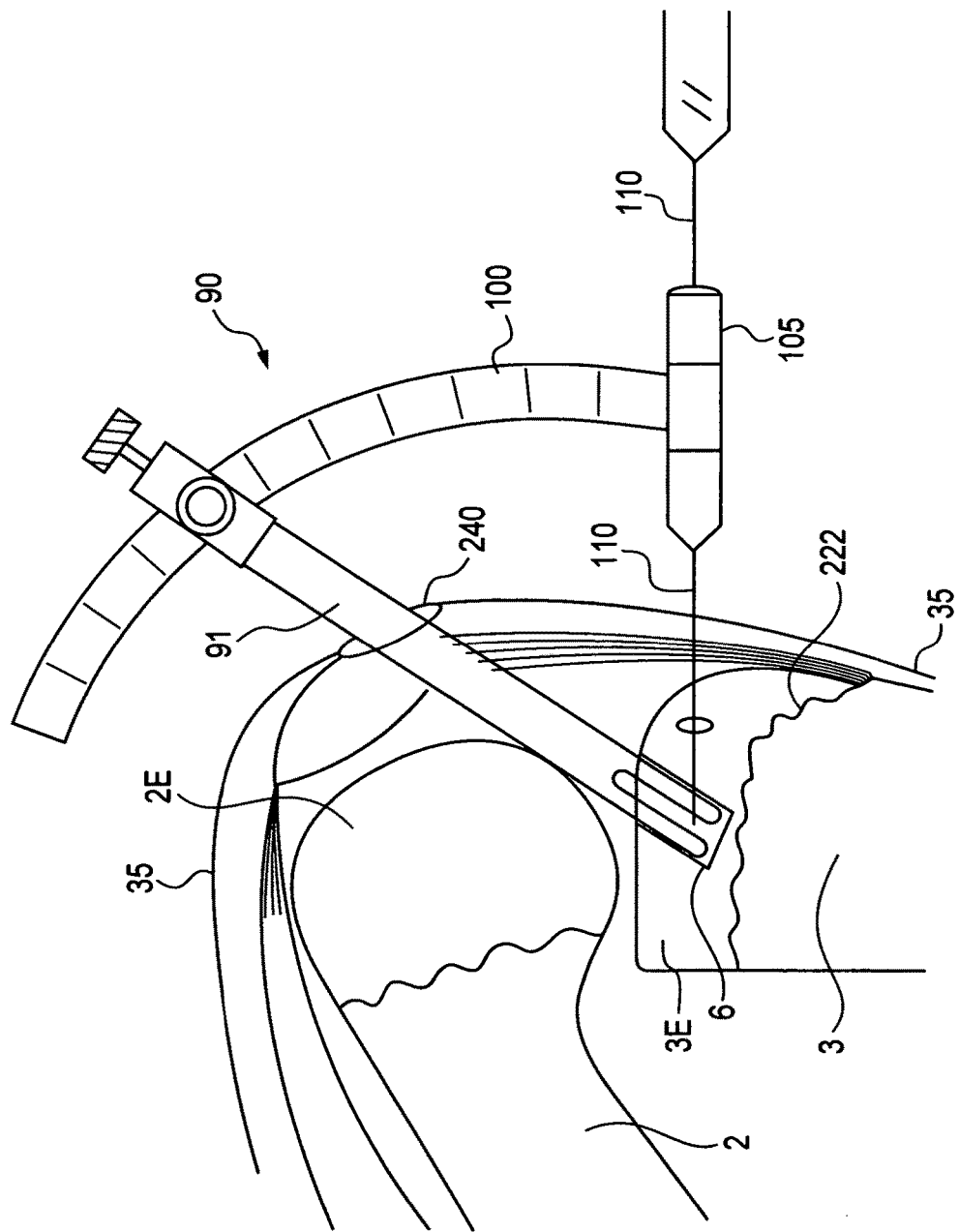
FIG. 66 is a schematic view of a manner of inserting a surgical guide pin of FIG. 22 across a bone tunnel in the tibial epiphysis of a skeletally immature knee without crossing the tibial physis utilizing the surgical pin guide of FIG. 21 in accordance with the present invention.

With the arthroscope in the conventional lateral infrapatellar arthroscopic portal 5, the alternative method of tunnel creation and graft fixation referred to above is performed by inserting the protective sleeve 225 with the cannulated bullet guide 235 into a high medial infrapatellar portal 240 down onto the ACL footprint on tibial bone 3 (see FIG. 64). Using intraoperative fluoroscopic techniques, a guide pin 30 is inserted through the cannulation 238 in the bullet guide 235 and advanced into the tibia 3 to a depth just short of the level of the tibial physis 222. The depth of the guide pin 30 is measured from the calibrations on pin 30 referenced from the stop end of bullet guide 235. The bullet guide 235 is removed from the protective sleeve 225 and cannulated drill bit 230 is advanced over the guide pin 30 to a depth just short of the depth of guide pin 30 as shown in FIG. 65. Cannulated drill bit 230 is calibrated and references off the handle end of protective sleeve 225. Target arm 91 of surgical pin guide 90 is inserted through the high medial infrapatellar portal 240 to the depth of the blind-ended tibial tunnel 6 (see FIG.

66). The radiographic marker 98 on the surface of target tip 92 marking the level of the target point 97 can be identified using intraoperative radiographic assistance in order to confirm proper positioning of the guide 90. The remaining steps are performed as described above to place a suspension pin, such as pin 80 or pin 81, in the tibial epiphysis 3E of tibia 3 and an interference screw-ligament washer, such as washer 130 or washer 140, in femoral epiphysis 2E of femur 2 (see FIGS. 67, 68 and 69).

Figure 67:
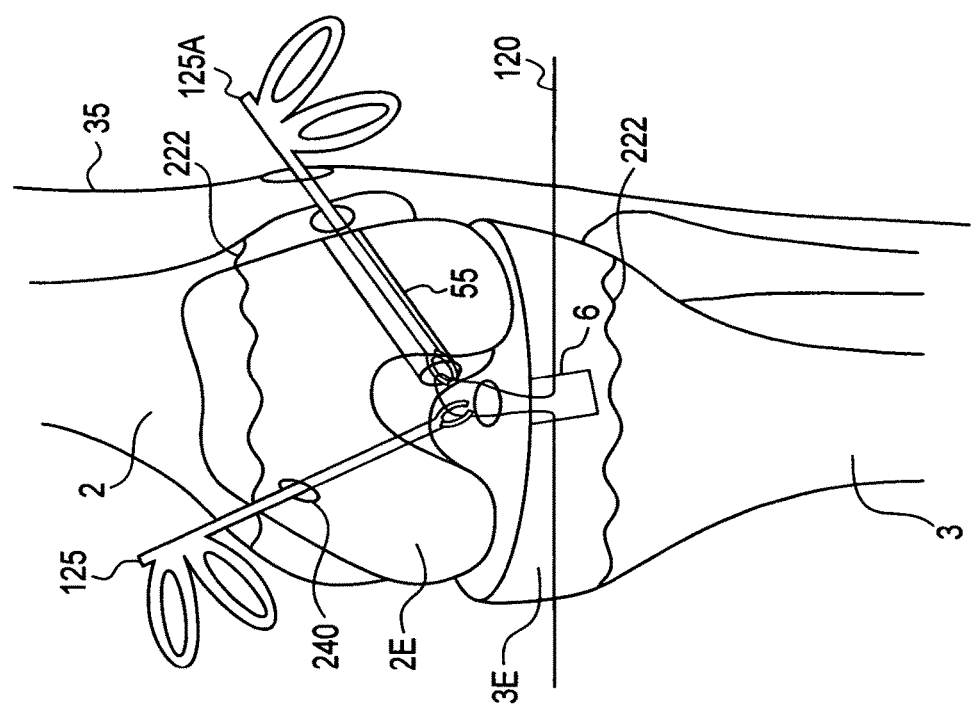
FIG. 67 is a schematic view of a manner of passing a central loop of flexible wire from an epiphyseal tibial bone tunnel out through a femoral tunnel in accordance with the present invention.
Figure 68:
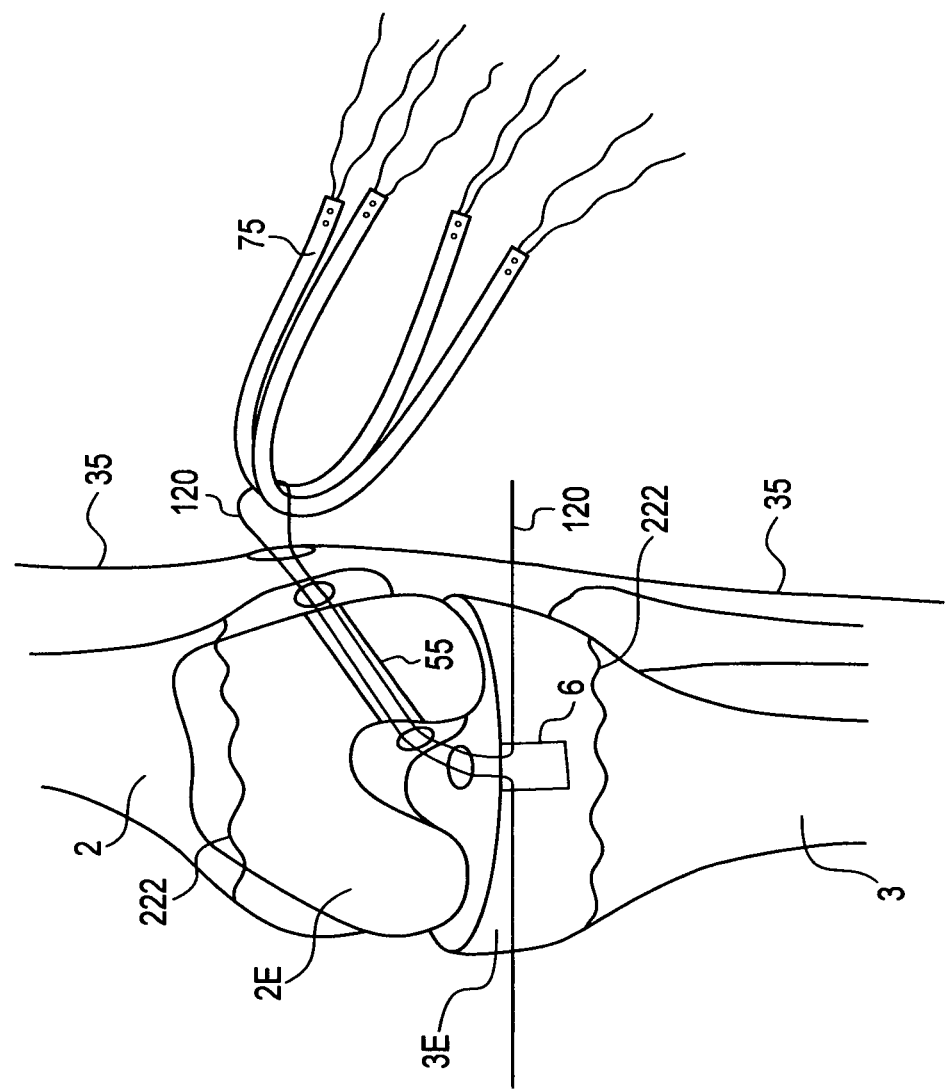
FIG. 68 is a schematic view of a manner of loading a free soft-tissue graft into a central loop of flexible wire in accordance with the present invention.

However, passage of the flexible wire 120 with wire passing tool 125 is done with a slight variation because of the blind-ended tibial tunnel 6 (see FIG. 67). First, the wire passing tool 125 is inserted through the high medial infrapatellar portal 240 to grasp the central loop of the flexible wire 120 in the tibial tunnel 6 and pass it to a second wire passing tool 125A which was inserted through femoral tunnel 55. The second wire passing tool 125A withdraws the central loop of flexible wire 120 outside the knee through femoral tunnel 55.

From all of the foregoing it will be evident that, although particular forms have been illustrated and described, nevertheless various modifications can be made without departing from the true spirit and scope of the invention. Accordingly, no limitations are intended by the foregoing description and the accompanying drawings, and the true spirit and scope of the invention are intended to be covered by the following claims.

I claim:

1. A cannulated scalpel comprising
   a blade having a blade end configured for creating a passageway through skin and soft-tissue to a target site on a bone,
   a flat handle adjacent the blade arranged in the same plane as the blade end, and
   a longitudinal cannulation in the handle and the blade forming a passageway adapted to accept a guide pin through the handle and blade.

* * * * *

UNITED STATES PATENT AND TRADEMARK OFFICE
CERTIFICATE OF CORRECTION

| | |
|---|---|
| PATENT NO. | : 10,034,674 B2 |
| APPLICATION NO. | : 11/701902 |
| DATED | : July 31, 2018 |
| INVENTOR(S) | : Steven C. Chudik |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 2649 days.

Signed and Sealed this
Twenty-first Day of May, 2019

Andrei Iancu
*Director of the United States Patent and Trademark Office*

UNITED STATES PATENT AND TRADEMARK OFFICE
CERTIFICATE OF CORRECTION

PATENT NO. : 10,034,674 B2
APPLICATION NO. : 11/701902
DATED : July 31, 2018
INVENTOR(S) : Steven C. Chudik Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 2677 days.

This certificate supersedes the Certificate of Correction issued May 21, 2019.

Signed and Sealed this
Seventeenth Day of June, 2025

Coke Morgan Stewart
*Acting Director of the United States Patent and Trademark Office*